US005436229A

United States Patent [19]

Ruterbories et al.

[11] Patent Number: 5,436,229

[45] Date of Patent: Jul. 25, 1995

[54] BISULFITE ADDUCTS OF ARGININE ALDEHYDES

[75] Inventors: Kenneth J. Ruterbories, Indianapolis; Robert T. Shuman, Greenwood, both of Ind.

[73] Assignee: Eli Lilly and Company, Indianapolis, Ind.

[21] Appl. No.: 206,579

[22] Filed: Mar. 4, 1994

[51] Int. Cl.[6] .................................... A61K 38/00

[52] U.S. Cl. .................................... 514/18; 514/19; 530/331; 540/476; 544/372; 544/111; 544/141; 544/58.5; 548/146; 548/214; 548/215; 548/240; 548/468

[58] Field of Search ................ 540/476; 544/372, 111, 544/141, 58.5; 548/146, 214–215, 240, 468; 530/351; 514/18–19

[56] References Cited

U.S. PATENT DOCUMENTS

| | | | |
|---|---|---|---|
| 4,316,889 | 2/1982 | Bajusz et al. | 424/177 |
| 4,346,078 | 8/1982 | Bajusz et al. | 424/177 |
| 4,399,065 | 8/1983 | Bajusz et al. | 260/112.5 R |
| 4,478,745 | 10/1984 | Bajusz et al. | 260/112.5 R |
| 4,596,789 | 6/1986 | Dutta et al. | 514/18 |
| 4,703,036 | 10/1987 | Bajusz et al. | 514/18 |
| 5,053,392 | 10/1991 | Klein et al. | 574/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |

FOREIGN PATENT DOCUMENTS

| | | |
|---|---|---|
| 293881 | 12/1988 | European Pat. Off. . |
| 410411 | 1/1991 | European Pat. Off. . |
| 479489 | 4/1992 | European Pat. Off. . |
| 526877 | 8/1992 | European Pat. Off. . |
| 503203 | 9/1992 | European Pat. Off. . |
| 529568 | 3/1993 | European Pat. Off. . |
| 530167 | 3/1993 | European Pat. Off. . |
| 542525 | 5/1993 | European Pat. Off. . |
| WO93/08211 | 4/1993 | WIPO . |

OTHER PUBLICATIONS

Bajusz, S., et al., *J. Med. Chem.*, 1990, 33, 1729–1735.

Fareed, J., et al., *Annals N.Y. Academy of Sciences*, 1981, 765–784.

Shuman, et al., Proceedings of the Twelfth American Peptide Symposium, Jun. 16–21, 1991 Abst.

Wilson, et al., American Heart Association, Nov. 11–14, 1991, Anaheim Convention Center, Anaheim, Calif. Abst.

Bajusz, et al., *Int. J. Peptide Res.*, 12, 1978, 217–221.

Gesellchen, et al., Tenth American Peptide Symposium, May 23–28, 1987, St. Louis, Mo. Abst.

Claeson, et al., Proceedings of the Twelfth American Peptide symposium, Jun. 16–21, 1991, Cambridge, Mass. pp. 824–825.

Smith, G. F., Shuman, R. T. Gesellchen, P. D., Craft, T. J., Gifford, P., Kurz, K. D., Jackson, C. V., Sandusky, G. E., and P. D. Williams, A New Family of Thrombin Inhibitors with Improved Specificity and Therapeutic Index. (Submitted to the American Heart Association, Oct., 1991, Circulation Oct., 1991, vol. 84, II–579, 1991).

Jackson, V., Wilson, H., Frank, J., Crowe, V., Craft, T., and G. Smith. The Thrombin Inhibitor, Methyl-D--Phe-Pro-Arginal—An Effective Adjunct to Coronary Artery Thrombolysis in the Anesthetized Dog. Faseb J. 5(4)A521 (1991) #865.

Crowe, V., Frank, J., Wilson, H., Coffman, B., Smith, G., and V. Jackson. Anticoagulant and Antithrombotic Efficacy of the Novel Thrombin Inhibitor Methyl-D-Phg-Pro-Arginal in a Canine Model of Coronary Thrombosis. Faseb J. 5(4)A521 (1991) Abst. #864.

(List continued on next page.)

*Primary Examiner*—Jill Warden
*Assistant Examiner*—Sheela J. Huff
*Attorney, Agent, or Firm*—Thomas E. Jackson; John C. Demeter; David E. Boone

[57] ABSTRACT

This invention relates to bisulfite adducts of L-Arginine aldehyde derivatives, pharmaceutical formulations containing those adducts and methods of their use as thrombin inhibitors, coagulation inhibitors and thromboembolic disorder agents.

49 Claims, No Drawings

OTHER PUBLICATIONS

Wilson, H., Frank J., Crowe, V., Coffman, B., Smith, G., Shuman, R., and V. Jackson. Anticoagulant and Antithrombotic Efficacy of the Novel Thrombin Inhibitor, Methyl-D-Phg-Pro-Arginal, in a Canine Model of Coronary Thrombosis (Arteriosclerosis and Thrombosis, 11(5), Oct., 1991).

Jackson, V., Wilson, H., Moore A., Craft J., Shuman, R., and G. Smith. The Novel Thrombin Inhibitor Methyl-D-Phg-Pro-Arginal: An Effective Conjunctive Agent to Coronary Artery Thrombolysis in the Anesthetized Dog. (Arteriosclerosis and Thrombosis, 11(5), Oct., 1991).

Shuman, R. T., Rothenberger, R. B., Campbell, C. S., Smith, G. F., Jackson C. V., Kurz, K. D., and P. D. Gesellchen. Prevention of Reocclusion by a Thrombin Inhibitor. (American Peptide Symposium, Jun., 1991, pp. 799–800).

Shuman, R. T., Rothenberger, R. B., Campbell, C. S., Smith, G. F., Jackson C. V., Kurz, K. D., and P. D. Gesellchen. A Series of Highly Active Serine Proteinase Inhibitors. (American Peptide Symposium, Jun. 1991, pp. 801–802).

Jackson, C. V., Frank, J. D., Crowe, V. G., Craft, T. J., and G. F. Smith. Assessment of the Anticoagulant and Antithrombotic Efficancy of the Thrombin Inhibitor, BOC-Phe-Pro-Arginal, in a Canine Model of Coronary Thrombosis. *Arteriosclerosis,* 10 922A (1990) Abst.

Jackson, C. V., Frank, J. D., Crowe, V. G., Craft, T. J., and G. F. Smith. The Thrombin Inhibitor, BOC-D-Phe-Pro-Arginal. An Effective Adjunct to Coronary Artery Thrombolysis in the Anesthetized Dog. *Arteriosclerosis,* 10 923a (1990).

Shackelford, K. A., Tanzer, R. L., Shuman, R., Gesellchen, P. D., Grindey, G. B., Sundboom, J. L., Smith, G. F., and R. L. Merriman. Inhibition of Spontaneous Metastasis by Boc-D-Phe-Pro-Arginal. American Association for Cancer Research, San Francisco, 1989. *Proc. Am. Assn. Cancer Res.,* 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund-Wistar (LW) Rats to Anti-Fibrin Agents. American Association for Cancer Research. New Orleans, May 1988, *Proc. Am. Assn. Cancer Res.,* 29 240 (1988).

Neubauer, B. L., Best, K. L., Gesellchen, P. D., Goode, R. L., Merriman, R. L., Tanzer, L. R., Shaar, C. J., Shuman, R., Sundboom, Pro-Arginal on the Metastasis of the PAIII Prostatic Adenocarcinoma in Male Lobund Wistar (LW) Rats. American Urological Association. Boston, May 1988, *J. Urol.,* 139 175A (1988).

Gesellchen, P. D., Smith, G. F., et al., Anticoagulant, Antithrombotic, and Antimetastic Effects of a Serine Proteinase Inhibitor. 10th American Peptide Symposium, Washington University, St. Louis, Mo. (1987).

Smith, G. F., Sundboom, J. L., Best, K., Gesellchen, P. D., Merriman, R. L., Shuman, R., and Neubauer, B. L. Heparin, Boc-D-Phe-Pro-Arginal, and Warfarin (Fibrin Antagonists) Inhibit Metastasis in an *In Vivo* Model. American Chemical Society National Meeting. Abstract Biol 70 Biochemistry (1987).

K. D. Kurz, T. Smith, R. A. Moore, and B. W. Main. Comparison of Thrombin Inhibitors in Rat Models of Thrombosis and Thrombolysis. Faseb Journal, vol. 5 (No. 4), 1991.

Tomori, et al., *Chromatographia,* vol. 19, 437–442 (1984).

Dayhoff, *Atlas of Protein Sequence and Structure,* 5, pp. 85–89 (1972).

Shuman, et al., *J. Med. Chem.,* 36(3), 314–319 (1993).

Jackson, et al., *J. Cardiovasc. Pharmacol.,* 21(4), 587–594 (1993).

Cheng, et al., *Tetrahedron Lett.,* 32(49), 7333–7336 (1991).

Bagdy, et al., *Thrombosis and Haemostasis,* 68(2), 125–129 (1992).

*Thrombosis and Haemostasis,* 65, 1289, Nos. 2150–2151 and 2152 (1991).

Bagdy, et al., *Thrombosis and Haemostasis,* 67(3), 325–330 (1992).

Bagdy, et al., *Thrombosis and Haemostasis,* 67(3), 357–365 (1992).

Balasubramanian, et al., *J. Med. Chem.,* 36, 300–303 (1993).

Shuman, et al., Oral Activity of Tripeptide Aldehyde Thrombin Inhibitors, Thirteenth American Peptide Symposium, Jun. 20–25, 1993 Abst.

Kurz et al., Antithrombotic Efficacy in the Rat After (List continued on next page.)

OTHER PUBLICATIONS

Intravenous and Oral Administration of a Direct Inhibitor of Thrombin Faseb, Mar. 28–Apr. 1, 1993.

Iwanowicz, et al., *Bioorg. Med. Chem. Lett.*, 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmacologist*, 35(3), 207 (1993).

Pozagay, et al., Study of the Specificity of Thrombin with Tripeptidyl–p–Nitroanilide Substrates, *Eur. J. Biochem.*, 115, 491–495 (1981).

BISULFITE ADDUCTS OF ARGININE ALDEHYDES

BACKGROUND OF THE INVENTION

This invention relates to bisulfite adducts of arginine aldehydes which are thrombin inhibitors and anticoagulants in mammals. In particular it relates to bisulfite adducts of L-Arginine aldehyde derivatives having high anticoagulant activity, antithrombotic activity, and oral bioavailability.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins.

Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al., *J. Med. Chem.*, 36, 314–319 (1993). These small synthetic peptide derivatives contain an aldehyde group bonded to the arginine residue.

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, preferably by an oral route, and do not interfere with lysis of blood clots, as required to maintain hemostasis.

Epimerization at the amino acid alpha-carbon is a known problem that plagues polypeptide synthesis and stability. This configurational inversion (loss of chiral integrity at one chiral center in a peptide having two or more chiral centers) may limit the prophylactic and therapeutic use of arginine aldehyde thrombin inhibitors. The aldehyde group on the arginine residue epimerizes from the preferred L configuration to the D diastereomer. Such configurational inversion occurs through a simple enolization reaction, cyclization (lactam) formation, or a combination of those reactions. These two reactions are influenced at least by the nature of substituents associated with the amino, carbonyl and alpha-carbon atom, temperature and basicity of the preparation, purification and reconstitution media.

Protection of the arginine aldehyde group from configurational inversion would greatly enhance the prophylatic and therapeutic efficacy of small synthetic peptides containing said group as thrombin inhibitors as epimerization to the D diastereomer is believed to inactivate the molecule as a thrombin inhibitor.

The present invention is directed to the discovery that the compounds of the present invention, as defined below, are potent thrombin inhibitors that have high bioavailability following oral administration; and importantly are substantially stabilized to configurational inversion.

Accordingly, it is a primary object of the present invention to provide configurational inversion stabilized bisulfite adducts of L-arginine aldehyde derivatives that are potent thrombin inhibitors useful as anticoagulants.

Other objects, features and advantages will be apparent to those skilled in the art from the following description and claims.

SUMMARY OF THE INVENTION

The present invention provides thrombin inhibiting bisulfite adducts of arginine aldehyde compounds having the formula

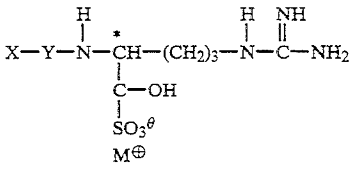

I wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

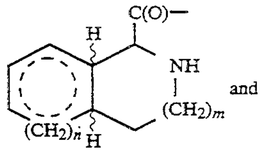

and

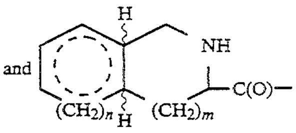

where n is 1–3, m is 0–3, and the broken lines mean the presence or absence of unsaturation; and in a sulfur containing group the sulfur may be oxidized with one or two oxygen atoms;

2) a group

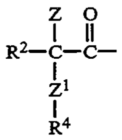

where Z is hydrogen, hydroxy, $C_1$-$C_4$ alkoxy or —$NHR^2$;

$R^2$ is hydrogen, $C_1$-$C_6$ alkyl, cyclopentyl, cyclohexyl, a group

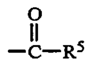

or —$S(O)_p$—$R^5$ where $R^5$ is $C_1$-$C_4$ alkyl $C_1$-$C_2$ perfluoroalkyl $C_1$-$C_4$ alkoxy, ($C_1$-$C_4$ alkoxy)$C_1$-$C_4$ alkyl, cyclopentyl, cyclohexyl, cyclopentyl-$CH_2$—, cyclohexyl-$CH_2$—, amino, mono ($C_1$-$C_4$) alkylamino, di($C_1$-$C_4$) alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or2;

$R^3$ is hydrogen, $C_1$-$C_4$ alkyl, unsubstituted or substituted phenyl or unsubstituted or substituted benzyl;

$Z^1$ is a bond or —$CH_2$—;

$R^4$ is $C_1$-$C_6$ alkyl, $C_1$-$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

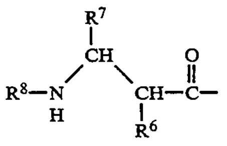

wherein $R^6$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl, or cyclohexyl($C_1$-$C_4$)alkyl;

$R^7$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl or cyclohexyl($C_1$-$C_4$)alkyl;

$R^8$ is hydrogen, $C_1$-$C_4$ alkyl or ($C_1$-$C_4$ alkyl)$S(O)_q$ where q is 0, 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

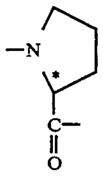 or 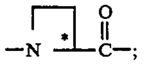

M is a pharmaceutically acceptable alkali metal or alkaline earth metal cation;

and pharmaceutically acceptable salts and solvates thereof.

In addition to the bisulfite adducts of formula I, the present invention provides pharmaceutical formulations comprising a bisulfite adduct of formula I in association with a pharmaceutically acceptable carrier, diluent or excipient.

The present invention also provides a method of inhibiting coagulation in mammals comprising administering to a mammal in need of treatment, a coagulation inhibiting dose of a bisulfite adduct of formula I.

The present invention further provides a method of inhibiting thrombin comprising administering to a mammal in need of treatment, a thrombin inhibiting dose of a bisulfite adduct of formula I.

Further, the present invention provides a method of treating a thromboembolic disorder comprising administering to a mammal in need of treatment, an effective dose of a bisulfite adduct of formula I.

DETAILED DESCRIPTION OF THE INVENTION

This invention relates to new bisulfite adduct inhibitors of thrombin, pharmaceutical compositions containing the adducts as active ingredients, and the use of the adducts as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl.

The term "alkoxy" means a straight or branched chain alkyl radical having the stated number of carbon atoms bonded to the parent moiety by an oxygen atom. The term "halo" means chloro, fluoro, bromo or iodo. The term "di($C_1$–$C_4$ alkyl)amino" means a group —N($C_1$–$C_4$ alkyl)$_2$ where each alky group, independently, has the stated number of carbon atoms.

The group

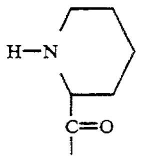

is referred to at times herein as homoprolinyl and abbreviated hPro.

The term "azetidine" refers to an azetidine-2-carbonyl group and is abbreviated Azt. The terms "thiazolidinoyl, isothiazolidinoyl, thiomorpholinoyl, piperazinoyl, morpholinoyl, oxazolidinoyl, and isoxazolidinoyl" refer to the stated ring group having a carbonyl functionality bonded thereto so as to afford a stable structure.

The term "2-azanorbornoyl" means a group

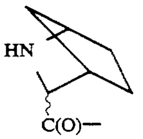

When X is a substituted homoprolinyl, prolinyl, thiazolidinoyl, isothiazolidinoyl, thiomorpholinoyl, 2-azanorbornoyl, or fused bicyclic ring groups, there can be one to three of the same or different substituents that will afford a stable structure selected from halo, hydroxyl, $C_1$–$C_4$ alkyl, $C_1$–$C_4$ alkoxy, amino (—$NH_2$), mono($C_1$–$C_4$ alkyl)amino, di($C_1$–$C_4$ alkyl)amino, mercapto, $C_1$–$C_4$alkylthio (—S(O)$_r$($C_1$–$C_4$ alkyl)), —NHS(O)$_r$ ($C_1$–$C_4$ alkyl), —NHC(O)$C_1$–$C_4$ alkyl, —S(O)$_r$NH2, —S(O)$_r$NH($C_1$–$C_4$ alkyl), —S(O)$_r$N($C_1$–$C_4$ alkyl)$_2$, substituted or unsubstituted phenoxy, substituted or unsubstituted naphthyloxy, substituted or unsubstituted pyridyloxy, substituted or unsubstituted phenylthio; r is 0, 1 or 2; and the substituents on the phenoxy, naphthyloxy, pyridyloxy and phenyl thio groups are one or two of the same or different substituents selected from halo, hydroxyl, $C_1$–$C_4$ alkyl, $C_1$–$C_4$ alkoxy, amino (—$NH_2$), mono($C_1$–$C_4$ alkyl) amino, di($C_1$–$C_4$ alkyl) amino, mercapto, $C_1$–$C_4$alkylthio (—S(O)$_r$($C_1$–$C_4$ alkyl)), —NHS(O)$_r$($C_1$–$C_4$ alkyl), —NHC(O) $C_1$–$C_4$ alkyl, —S(O)$_r$NH2, —S(O)$_r$NH($C_1$–$C_4$ alkyl), —S(O)$_r$N($C_1$–$C_4$ alkyl)$_2$, and r is 0, 1 or 2.

The term "perfluoroalkyl" means a straight or branched chain alkyl radical having the stated number of carbon atoms with all available valences substituted with fluoro atoms such as trifluoromethyl and pentafluoroethyl.

The term "5 or 6 membered heterocyclic ring" means any 5 or 6 membered ring that will afford a stable structure containing one or two nitrogen atoms; one sulfur atom; one oxygen atom; one nitrogen and one sulfur atom; or one nitrogen and one oxygen atom. The 5-membered ring has one or two double bonds and the 6-membered ring has two or three double blonds. Heterocyclics include furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl and thiazinyl.

The term "9 or 10 membered heterocyclic ring" means any fused bicyclic heterocyclic group in which any off the above 5 or 6 membered rings is fused to a benzene ring a cyclohexane ring, or another 6 membered heterocyclic ring, as defined above, that will afford a stable structure. These heterocyclics include indolyl, benzothienyl, benzofuryl, benzoxazolyl, benzoisoxazolyl, benzopyrazolyl, quinolinyl, isoquinolinyl, benzimidazolyl and benzothiazolyl.

The term "9 or 10 membered bicyclic hydrocarbyl group" means a fused bicyclic group

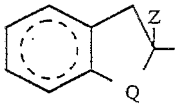

where Q is —$CH_2$—, —CH=CH— or —$CH_2$—$CH_2$—;

Z is as shown and defined above for Formula I; and the broken lines mean the presence or absence of unsaturation in the ring.

Representative examples of these fused bicyclic groups include indanyl, dihydronaphthyl and tetrahydronaphthyl.

It will be appreciated that many of the above heterocycles may exist in tautomeric forms. All such forms are included within the scope of this invention.

Where X is a group

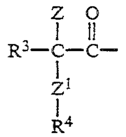

each of the defined aryl, heterocycles and bicyclic hydrocarbyls are unsubstituted or substituted with one or two substituents that will afford a stable structure independently selected from halo, hydroxyl, $C_1$–$C_4$ alkyl, $C_1$–$C_4$ alkoxy, amino (—$NH_2$), (mono($C_1$–$C_4$ alkyl) amino, mercapto, and ($C_1$–$C_4$ alkyl)thio (—S(O)$_r$$C_1$–$C_4$ alkyl), —NHS(O)$_r$($C_1$–$C_4$ alkyl), NHC(O)$C_1$–$C_4$ alkyl, —S(O)$_r$$NH_2$, —S(O)$_r$NH($C_1$–$C_4$ alkyl), and —S(O)$_r$N($C_1$–$C_4$) alkyl)$_2$, where r is 0, 1 or 2.

In addition, diastereomers exist at the X substituent and, depending on substitutions on said X substituent, further diastereomers may exist. The compounds of the present invention include mixtures of two or more diastereomers as well as each individual isomer.

The term "phen($C_1$–$C_4$)alkyl" means a straight chain alkyl radical having the stated number of carbon atoms with a phenyl ring bond to the terminal carbon atom of the alkyl radical.

The term "cyclopentyl($C_1$-$C_4$)alkyl" means a straight chain alkyl radical having the stated number of carbon atoms with a cyclopentyl ring bonded to the terminal carbon atom of the alkyl radical.

The term "cyclohexyl($C_1$-$C_4$)alkyl" means a straight chain alkyl radical having the stated number of carbon atoms with a cyclohexyl ring bonded to the terminal carbon atom of the alkyl radical.

The term "norbornanyl" means a group having the structure

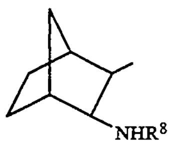

where —$NHR^8$ are the same amino group defined for Formula I.

A substituted phenyl and substituted phen ($C_1$-$C_4$) alkyl where X is a group

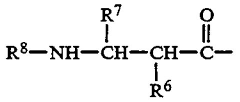

can have one or two of the same or different substitutents on the phenyl ring selected from halo, hydroxy, $C_1$-$C_4$ alkyl, $C_1$-$C_4$ alkoxy, amino (—$NH_2$), and $C_1$-$C_4$ alkylamino.

When $R^7$ and $R^8$ or $R^6$, $R^7$ and $R^8$, with the respective carbon and nitrogen atoms to which they are bounded, combine to afford a stable substituted 5 or 6 membered nitrogen containing heterocyclic ring which may further contain another hetero atom selected from nitrogen, oxygen and sulfur, or a stable substituted 9 or 10 membered nitrogen containing heterocyclic ring which may further contain another hetero atom selected from nitrogen, oxygen and sulfur, there are one or two substituents selected from halo, hydroxyl, $C_1$-$C_4$ alkyl, $C_1$-$C_4$ alkoxy, amino (—$NH_2$), mono($C_1$-$C_4$ alkyl ) amino, di($C_1$-$C_4$ alkyl)amino, mercapto, ($C_1$-$C_4$ alkyl)thio (—$S(O)_r C_1$-$C_4$ alkyl), —$NHS(O)_r$ ($C_1$-$C_4$ alkyl), —NHC(O) $C_1$-$C_4$ alkyl, —$S(O)_rNH_2$, —$S(O)_rNH(C_1$-$C_4$alkyl ), and —$S(O)_rN(C_1$-$C_4$alkyl$)_2$, and r is 0, 1 or 2;

In addition, diastereomers may exist at the carbon atoms to which the $R^6$ and $R^7$ substituents are bonded depending on substitutions. The compounds of the present invention include mixtures of two or more diastereomers as well as each individual isomer.

In the representation of Formula I, the carbonyl functionality of group X is attached to the amine functionality of the Y group. The carbonyl functionality of Y is attached to the amino group drawn in Formula I.

The asterisks in formula I and substituent Y denote a chiral center that is (L).

In addition, diastereomers exist at the X substituent and, depending on substitutions on said X substituent, further diastereomers may exist. The adducts of the present invention include mixtures of two or more diastereomers as well as each individual isomer.

Preferred adducts of the present invention are those compounds of formula I where X is a group

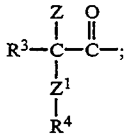

Z is —$NHR^2$;

$R^2$ is $C_1$-$C_6$ alkyl,

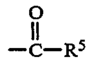

or —$S(O)_p$—$R^5$;

R3 is hydrogen or $C_1$-$C_4$ alkyl;

$Z^1$ is a bond or —$CH_2$—;

$R^4$ is unsubstituted or substituted aryl where aryl is phenyl or naphthyl;

$R^5$ is $C_1$-$C_4$alkyl, $C_1$-$C_4$alkoxy, amino, mono($C_1$-$C_4$) alkylamino or di($C_1$-$C_4$)alkylamino;

or an unsubstituted or monosubstituted fused bicyclic ring selected from

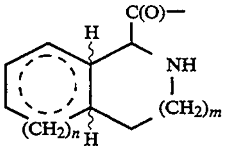

and

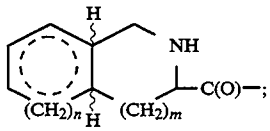

M is sodium, potassium, calcium or magnesium; where n, m, p and Y are as defined above for formula I, and pharmaceutically acceptable salts and solvates thereof.

Particularly preferred adduces of the present invention are those compounds of formula I where X is a group

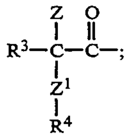

Z is —$NHR^2$;

$R^2$ is $C_1$-$C_6$ alkyl;

$R^3$ is hydrogen;

$Z^1$ is a bond or —$CH_2$—;

$R^4$ is unsubstituted or substituted phenyl;

or a fused bicyclic ring selected from

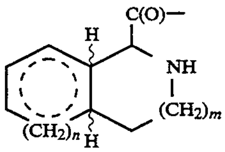

and

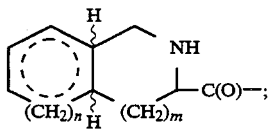

M is sodium;

where n, m and Y are as defined above for formula I; and pharmaceutically acceptable salts or solvates thereof.

As mentioned above, the invention includes pharmaceutically acceptable salts of the adducts defined by the above formula I. A particular adduct of this invention can possess one or more sufficiently basic functional groups, and accordingly react with any of a number of nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene sulfonic, methanesulfonic acid, oxalic acid, p-bromo phenyl sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

As stated above, the present invention includes solvates of the adducts of Formula I and the pharmaceutically acceptable salts thereof. A particular adduct of the present invention or a pharmaceutically acceptable salt thereof may form solvates with water or common organic solvents. Such solvates are included within the scope of compounds of the present invention.

The adducts of the present invention are readily prepared by commonly used procedures. Generally, the corresponding arginine aldehyde compound of formula Ia is combined with about a stoichiometric amount of a pharmaceutically acceptable alkali metal or alkaline earth metal bisulfite in a polar solvent or mixture of solvents to afford the desired bisulfite adduct. The adduct is then isolated and lyophilized by conventional methods or formulated as described below. If lyophilized, the adduct is formulated, as described below, prior to administration. Although preferably a stoichiometric amount of metal bisulfite is combined with the arginine aldehyde, it is possible to use more or less, as desired. The preferred polar solvent is water.

The alkali metal and alkaline earth metal bisulfite compounds contemplated as useful for preparing the bisulfite adducts of the present invention are those pharmaceutically acceptable bisulfite compounds where the metal cation is, for example, sodium, potassium, calcium or magnesium. The preferred bisulfite compound is sodium bisulfite.

The corresponding arginine aldehyde compounds of formula Ia are prepared by known methods of peptide coupling. According to one such method the acid PX—COOH, where X —COOH is the acid equivalent of the X groups as defined for formula I, and P is an amino protecting group, is coupled with a carboxy protected proline (or azetidine-2-carboxy ester) to form the dipeptide. The carboxy protecting ester group of the proline moiety is then removed (deblocked or deesterified) and the free acid form of the dipeptide is coupled with the lactam form of arginine. The above reaction sequence is illustrated by the following Scheme 1:

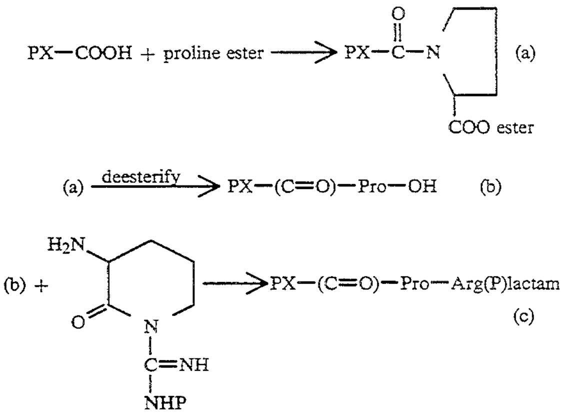

wherein P represents an amino protecting group.

The coupled Arg(P) lactam product (c) is reacted with a hydride reducing agent, preferably lithium aluminum hydride or lithium tri-tert-butoxyaluminohydride, in an inert solvent or mixture of solvents to reduce the lactam ring and provide the tripeptide in the arginine aldehyde form represented by the formula

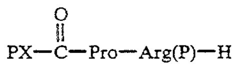

wherein (P) represents amino protecting groups.

The protecting groups are removed by procedures known to those skilled in the art such as hydrogenation over a metal catalyst.

The lactam form of arginine is obtained by intramolecular coupling of amino protected arginine [Arg-OH]. For example, Boc-Arg(Cbz)OH represented by the formula

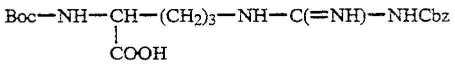

where Boc is t-butyloxycarbonyl and Cbz is benzyloxycarbonyl is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the di-amino protected arginine as shown below

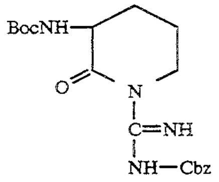

Prior to use in the coupling with the PX(C=O)-Pro-OH as shown in the above scheme, the Boc or other amine protecting group is selectively removed with trifluoroacetic acid or HCl to provide the requisite free amino group.

The coupling of an PXCOOH compound with a proline ester, when X is as defined above for formula I, is carried out by first protecting the amino group of the amino acid. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth- 1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl-)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl)ethoxycarbonyl, allyloxycarbonyl, 1-(trimethylsilylmethyl)-prop-1-enyloxycarbonyl, 5-benzisoxalylmethoxycarbonyl, 4-acetoxybenzyloxycarbonyl, 2,2,2-trichlorethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)-phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction an ester protecting group for proline is employed which is removable by conditions under which the amino protecting group remains intact. The amino protecting group of the acylating acid PXCOOH thus remains in place for protection of the amino group during the subsequent coupling with the arginine lactam compound to form c.

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$–$C_3$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, 2-(trimethylsilyl)ethyl, 2-(di (n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Preferred carboxy protecting groups are $C_1$–$C_3$ alkyl and benzyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of formula I where Y is azetidinyl (or prolinyl) are prepared in an analogous manner by known methods of peptide coupling. According to one such method, the cyclic lactam form of arginine (e) is prepared and coupled with an amino protected azetidine-2-carboxylic acid (d) as shown below to afford the dipeptide (f)

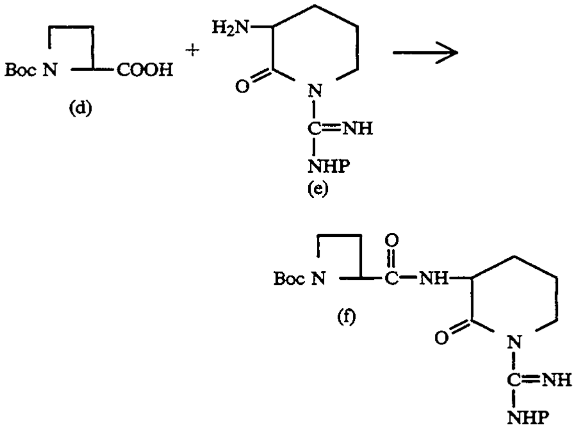

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers, incorporated herein by reference in its entirety. The Boc, or other suitable protecting group, is removed from the azetidine ring nitrogen which is then acylated with the desired amino acid acyl group to afford the tripeptide shown below.

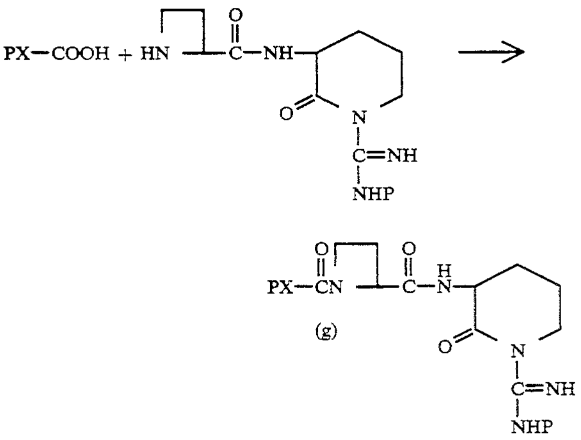

(g)

Although illustrated and described for those compounds of the present invention where Y is azetidinyl-2-carbonyl, one skilled in the art will appreciate these procedures can also be used to afford those compounds of the present invention where Y is prolinyl.

The coupled Arg(P) lactam product (g) is reduced with a hydride reducing agent, preferably lithium aluminum hydride or lithium tri-tert-butoxyaluminohydride, in an inert solvent or mixture of solvents to reduce the lactam and provide the tripeptide in the arginine aldehyde form represented by the formula PX(C=O)—Azt—Arg(P)—H wherein P represents an amino protecting group. The protecting groups are removed by procedures known to those skilled in the art such as hydrogenation over a metal catalyst.

Alternatively, the compounds of the invention are prepared by coupling the PXCOOH acid with carboxy protected azetidine-2-carboxylic acid. The carboxy is deprotected as the dipeptide which is then coupled with the amino protected arginine in the lactam form prepared as described above. The tripeptide is then reduced to provide the amino protected arginal tripeptide as described above.

The coupling of an PXCOOH compound is carried out by first protecting the amino group of the amino acid. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

Those compounds of formula I where the X substituent (α,α-disubstituted amino acids) are not commercially available can be readily prepared by the methods illustrated below in scheme 2. A suitable α-amino ester is condensed with benzophenone imine and the resulting imines are deprotonated with a strong base such as potassium t-butoxide or lithium bis(trimethylsilyl)amide. The resulting carbanions are then treated with an appropriate electrophile such as primary alkylhalides, allylic alkyl halides or benzylic alkyl halides. The imine can then be removed by treatment with aqueous acid (from about 1N to about 3N inorganic acid, preferably HCl) and the resulting amino acid derivative can be carried on to the compounds of formula I as described above.

Scheme 2:

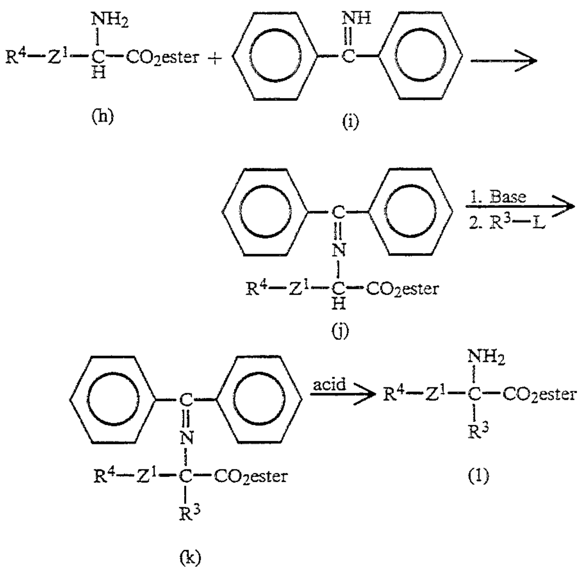

(h) (i) (j) (k) (1)

In Scheme 2, $Z^1$, $R^4$ and $R^3$ are as defined for formula 1, L is a good leaving group, preferably halo, and "ester" is a suitable carboxy protecting group, preferably $C_1$-$C_4$ alkyl. The compound (1) is further reacted using convential synthetic procedures to afford the desired Z substituent as defined for formula I. Such procedures include blocking the amino group with a suitable protecting group, deblocking the carboxy group and then carrying out coupling to afford the compounds of the present invention as described above.

An α-amino acid ester which is N-substituted (such as Azt) (ie., these compounds of formula I were Z is $—NHR^2$ and is taken together with $R^3$) can be α-substituted directly, using a strong base (such as lithium diisopropyl amide, LDA) and an electrophile $R^4$-$Z^1$-L, where $R^4$ and $Z^1$ are defined for formula I and L is a good leaving group, preferably halo, provided a nitrogen protecting group (P) is employed which is stable to the basic reaction conditions.

Both of the above procedures for α-substituting an α-amino acid ester afford a mixture of enantiomers which can be separated or carried forward as a racemic mixture.

A further method for preparing suitable α-substituted-α-amino acids (substituent X of formula I) is by means of the Strecker synthesis. Generally, α-amino nitriles are prepared by the treatment of an aldehyde or ketone with NaCN and $NH_4Cl$. Further details regarding this synthetic method, and variants thereof, are in March, *Advanced Organic Chemistry,* 3rd Ed., John Wiley & Sons, Inc. (1985), pp. 855–856.

The compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of formula Ia, while at the same time preparing a desired stable salt form, is that described in U.S. Pat. No. 5,250,660, incorporated by reference herein. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form e.g. Bio-Rad AG-1X8. After adjustment of the pH, the solution of tripeptide sulfate or hydrochloride salt is lyophilized to provide the pure salt in dry powder form. In an example of the process, crude D-hPro-L-Azt-L-Arg-H sulfate is dissolved in water and the solution is loaded on Vydac $C_{18}$ RPHPLC 5 cm×50 cm column. A gradient of 2–20 percent B (A=0.01 percent $H_2SO_4$; B=acetonitrile) over 10 hours is used. Multiple fractions are collected and those containing product as determined by analytical RPHPLC are pooled. The pH of the pooled fractions is adjusted to pH 4.0–4.5 with AG-1X8 resin in hydroxide form (Bio-Rad, 3300 Ragatta Blvd., Richmond, Calif. 94804). The solution is filtered and the filtrate is lyophilized to provide the pure D-,L-,L-, tripeptide in the form of the sulfate salt.

The optically active isomers of the diastereomers of the X substituent are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe the invention and are not to be construed as limitations thereof.

The $R_f$ values in the following examples unless otherwise stated, were determined by silica gel thin layer chromatography using Kieselgel 60F-254 (Merck, Darmstadt) in the following solvent systems:

(A) chloroform-methanol-acetic acid, 135:15:1, v:v:v
(B) ethyl acetate-acetic acid-absolute ethanol, 90:10:10, v:v:v
(C) chloroform-methanol-acetic acid, 90:30:5, v:v:v
(D) ethyl acetate The analytical HPLC methods used in the examples were as follows:

Method 1. Waters 600E using a Vydac $C_{18}$ reversed-phase column of 0.46 cm×10 cm. The chromatogram was monitored on an LDC at 214 nM using a gradient of A=water containing 0.1 percent (v:v)TFA and B=acetonitrile containing 0.1 percent (v:v) TFA.

Method 2. Pharmacia FPLC using a Vydac $C_{18}$ reversed-phase column measuring 0.46 cm×10.0 cm. Monitoring was done on a Pharmacia UV-M at 214 nM using a gradient of either A=water containing 0.1 percent (v:v) TFA or B=acetonitrile containing 0.1 percent (v:v) TFA.

Method 3. Hitachi L-6200 using a Vydac $C_{18}$ reversed-phase column of 0.46 cm×10 cm. Samples were eluted using a gradient composed of A (0.1% (v:v) aqueous TFA) and B (0.1% TFA in acetonitrile). The chromatogram was monitored at 214 nm using a L-4000 UV detector.

The abbreviations used in the examples have the following meanings.

Amino acids: Arg=arginine, Pro=proline, hPro=-homoproline, Azt=azetidine-2-carboxylic acid, Phe=-phenylalanine, hPhe=homophenylalanine, Gly=glycine Ac=Acetyl
Boc=t-butyloxycarbonyl (t-butoxycarbonyl)
Bzl=benzyl
Cbz=benzyloxycarbonyl
Cha=cyclohexylalanyl
Chg=cyclohexylglycinyl
DCC=dicyclohexylcarbodiimide
DMF=dimethylformamide
DMSO=dimethylsulfoxide
EtOAc=ethyl acetate
$Et_2O$=diethyl ether
EtOH=ethanol
FAB-MS=fast atom bombardment mass spectrum
FD-MS=field desorption mass spectrum
HOBT=1-hydroxybenzotriazole hydrate
HPLC=High Performance Liquid Chromatography
IR=Infrared Spectrum
LAH=Lithium Aluminum Hydride
MOC=methoxycarbonyl
NMR=Nuclear Magnetic Resonance
NMI=N-methylindole-2-carbonyl
OPFF=penta fluorophenoxy
PFF=pentafluorophenyl
Ph=phenyl
Phg=phenylglycinyl
RPHPLC=Reversed Phase High Performance Liquid Chromatography
Piq=perhydroisoquinolyl
1-Piq=perhydroisoquinol-1-ylcarbonyl
3-Piq=perhydroisoquinol-3-ylcarbonyl
TFA=trifluoroacetic acid
THF=tetrahydrofuran
Tiq=1, 2, 3, 4- tetrahydroisoquinolyl
1-Tiq=1, 2, 3, 4- tetrahydroisoquinol-1-ylcarbonyl
3-Tiq=1, 2, 3, 4- tetrahydroisoquinol-3-ylcarbonyl
TLC=thin layer chromatography Unless otherwise stated, pH adjustments and work up are with aqueous acid or base solutions.

EXAMPLE 1

Preparation of D-Homoprolinyl-L-Prolinyl-L-Arginine Aldehyde Dihydrochloride (D-hPro-Pro-Arg-H.2HCl)

A) Cbz-D-homoproline

D-pipecolic acid (5.0 g, 38.7 mmol) was dissolved in tetrahydrofuran (100 mL) and water (30 mL). The pH of the solution was adjusted to 9.5 with 2N NaOH and benzyl chloroformate (5.5 mL, 38.7 mmol) was added dropwise and the pH maintained at 9.5 with 2N NaOH. The reaction was stirred for an additional 1 hour at room temperature. The organic solvent was evaporated in vacuo, diethylether (100mL) and water (50 mL) were added to the residue. The aqueous layer was separated, the pH of the solution was adjusted to 2.8 with 3N HCl and ethyl acetate (150 mL) was added. The organic layer was separated and dried ($MgSO_4$); the filtrate was concentrated in vacuo to give a clear oil of the title compound (9.6 g; 95 percent yield)

FD-MS 264 (MH+);

TLC $R_f$(A) 0.37; $^1$HNMR ($CDCL_3$) δ 1.22–1.58 (m, 2H), 1.60–1.80 (m, 2H), 2.20–2.35 (m, 1H), 2.98–3.18 (m, 1H), 4.00–4.20 (m, 1H), 4.85–5.05 (m, 1H) 5.20 (s, 2H), 7.30–7.40 (d, 5H);

$[\alpha]_D$ +39.0° (C=0.5 / MeOH)

B) Cbz-D-homoprolinyl-Proline

Cbz-D-homoproline (A) (9.5 g, 36 mmol) was dissolved in EtOAc (100 mL) and the solution cooled to 0° C. Added to the solution was 2,4,5 trichlorophenol (7.1 g, 36 mmol) and dicyclohexylcarbodiimide (7.4 g, 36 mmol). The reaction was stirred for 1 hour at 0° C. and 1 hour at room temperature. The precipitate was filtered and the filtrate concentrated in vacuo to an oil. The oil was dissolved in pyridine (100 mL), L-Proline (4.2 g, 36mmol), and triethylamine (5.0 mL, 36 mmol) were added. The reaction was stirred at room temperature (24 hours). The reaction solvent was removed in vacuo to an oil. The residue was dissolved in water (100 mL), diethyl ether (50 mL) was added and the pH adjusted to 9.5 with 2N NaOH. The aqueous layer was extracted twice with diethyl ether. The aqueous layer was separated, the pH adjusted to 2.8 with 3N HCl and EtOAc (150 mL) was added. The organic layer was separated, dried ($MgSO_4$), and the filtrate evaporated in vacuo to an amorphous solid (11.4 g; 88 percent yield);

FD-MS 361 (MH+);

TLC $R_f$(A) 0.78;

$[\alpha]_D$=−2.7° (C=0.5 / Trifluoroethanol);

Elemental Analysis Calculated for $C_{19}H_{24}N_2O_5$: C 63.32 H 6.71 N 7.77 Found: C 63.42 H 6.84 N 7.96

C) Boc-Arg(Cbz)-OH

Boc-Arg(HCL)-OH (82.1 g, 250 mmol) was dissolved in 5N NaOH (240 mL) in a 3 necked flask. The reaction mixture was chilled to −5° C. and the pH was maintained at 13.2–13.5 using 5N NaOH (250 mL) while adding benzylchloroformate (143 mL, 1.0 mol) dropwise (55 min). The reaction mixture was stirred for an additional 1 hour at −5° C. and diluted with $H_2O$ (100 mL) and $Et_2O$ (500 mL). The aqueous layer was separated and extracted with $Et_2O$ (2×500 mL). The aqueous layer was acidified to pH 3.0 with 3N $H_2SO_4$ (560 mL) and extracted with EtOAc (550 mL). The aqueous layer was separated and extracted once with EtOAc. The combined EtOAc layers were washed with water and dried ($MgSO_4$). The organic layers were concentrated to dryness in vacuo to give the title compound (66.1 g; 65 percent yield):

TLC $R_f$(C) 0.43;

FD-MS 408 (M+);

$^1$HNMR ($CDCl_3$) δ 1.42 (s, 9H), 1.61–1.91 (m, 4H), 3.23–3.41 (m, 2H), 4.17 (d, 1H), 5.21 (s,2H), 5.62 (d, 1H), 7.30–7.42 (m,6H), 8.37 m, 1H).

D) Boc-Arg(Cbz)-Lactam

Boc-Arg(Cbz)-OH (C) (66.0 g, 0.162 mol) was dissolved in THF (230 mL) and cooled to −10° C. To the reaction mixture was added N-methylmorpholine (18.7 mL, 0.17 mol) followed by isobutylchloroformate (22.5 mL, 0.17mol). The reaction mixture was stirred 5 minutes at −10° C. and triethylamine (23.5 mL, 0.17 mol) was added. The reaction mixture was stirred for 1 hour at −10° C. and 1 hour at room temperature. The reaction mixture was poured into 1 L of ice-water and the resulting precipitate filtered, washed with cold water, and dried in vacuo. The product was crystallized from EtOAc to give the title compound (38.05 g; 60 percent yield):

TLC $R_f$(A) 0.77;

FD-MS 391 (MH+);

$^1$HNMR ($CDCl_3$) δ 1.48 (s, 9H), 1.78–1.98 (m, 2H), 2.50 (m, 1H), 3.41 (m, 1H), 4.43 (m, 1H), 4.90 (m, 1H), 5.16 (s, 2H), 5.27 (m, 1H), 7.28–7.45 (m, 6H), 9.41 (m, 1H), 9.68 (m, 1H).

E) HCl.Arg(Cbz)-Lactam

A solution of HCl(g) saturated in EtOAc (7.2 L) was added dropwise over 30 minutes to a solution of Boc-Arg(Cbz)-Lactam (D) (641 g, 1.64 mol) dissolved in $CH_2Cl_2$ (3 L ) at −10° C. The reaction was allowed to stir 1 hour at −10° C. and slowly warmed to room temperature over 3 hours. Diethyl ether (12 L) was added and the precipitate was filtered, washed with diethyl ether, dried ($MgSO_4$) and concentrated to dryness in vacuo to give the title compound (580 g):

TLC $R_f$(C) 0.29;

FD-MS 291 (MH+).

F) Cbz-D-hPro-Pro-Arg(Cbz)-Lactam

In flask 1 Cbz-hPro-Pro-OH (B) (11.1 g, 30.8 mmol) was dissolved in DMF (75 mL), cooled to −15° C. and N-methylmorpholine (3.4 mL, 30.8 mmol) was added followed by isobutylchloroformate (4.0 mL, 30.8 mmol). The reaction mixture was stirred at −15° C. for 2 minutes.

In flask 2 HCl.Arg(Cbz)-Lactam (E) (10.1 g, 30.8 mmol) was dissolved in DMF (75 mL), cooled to 0° C., and diisopropylethylamine (10.7 mL, 61.6 mmol) was added. The reaction mixture was stirred at 0° C. for 2 minutes.

The contents of flask 2 were added to flask 1 in one portion and the reaction mixture was stirred for 4 hours at −15° C. The reaction mixture was slowly warmed to room temperature (24 hours). To the reaction mixture was added 1N $NaHCO_3$ (5 mL) and the reaction solvent was removed in vacuo. To the oil was added EtOAc (200 mL) and water (100 mL), the organic layer was separated, washed with 1N $NaHCO_3$, water, 1.5N citric acid, and water. The organic layer was dried ($MgSO_4$), and the filtrate evaporated to an amorphous solid of the title compound (17.4 g, 89 percent yield):

TLC $R_f$(A) 0.66;

FAB-MS 633 (MH+).

G) Cbz-D-hPro-Pro-Arg(Cbz)-H

Cbz-D-hPro-Pro-Arg(Cbz)-Lactam (F) (17.2 g, 27.1 mmol) was dissolved in anhydrous THF (200 mL) and placed in a flask under a $N_2$ atmosphere. The reaction mixture was cooled to −65° C. and lithium aluminum hydride 1M in THF (27.1 mL, 27.1 mmol) was added dropwise over 5 minutes. The reaction mixture was stirred at −65° C. for 30 minutes. A solution of 5 mL of THF and 5 mL of 0.5N $H_2SO_4$ was added dropwise to the reaction mixture over 5 minutes. The reaction mixture was diluted with EtOAc (150 mL), and water (50 mL) and the organic layer separated. The organic layer was washed with water (2×100 mL) and dried ($MgSO_4$). The filtrate was concentrated to dryness in vacuo to an amorphous solid to give the title compound (14.1 g; 82 percent yield):

TLC $R_f$(A) 0.33;

FAB-MS 635 (MH+).

H) D-hPro-Pro-Arg-H-2HCl.1.5 $H_2O$

Cbz-D-hPro-Pro-Arg(Cbz)-H (G) (14.0 g, 22.0 mmol) was dissolved in ethanol (150 mL), water (50 mL), and 1N HCl (55 mL). To the solution was added 5 percent Pd/C (5.0 g) and the reaction was hydrogenated at ambient temperature and pressure for 3 hours and the reaction purged with nitrogen for 5 minutes. The catalyst was removed by filtration through a Celite® pad and the filtrate concentrated in vacuo down to 100 mL. An additional 50 mL of $H_2O$ was added to the reaction and pH of solution adjusted to 4.0 with BioRad AG1-X8 resin (hydroxide form). The resin was removed by filtration and the solution lyophilized to give 8.29 g (86 percent ) of crude title compound. The crude material in two portions was dissolved in 20 mL 0.05 percent HCl (pH 2.5) and applied to two 5×25 cm columns (Vydac $C_{18}$ resin) connected in series. A gradient system consisting of (A) 0.05 percent HCl and (B) $CH_3CN$ was used to elute the pure peptide. The gradient used was an increasing concentration of $CH_3CN$ from 2 percent to 10 percent. Fractions were collected and pooled on the basis of analytical RPHPLC profile. The combined fractions were adjusted to pH 4.0 using AG1-X8 resin (Bio-Rad analytical anion exchange resin 50–100 mesh) in hydroxide form. The solution was filtered, and the filtrate was lyophilized to dryness resulting in pure title compound (3.1 g; 61 percent yield):

FAB-MS 367 (MH+);

Amino acid analysis: hPro, 1.00; Pro, 0.98; $[\alpha]_D = -88.4°$ (C=0.5 / 0.1N HCl);

Elemental Analysis Calculated for $C_{17}H_{30}N_6O_3.2HCl.1.5H_2O$: C 43.78, H 7.56, N 18.02 Found: C 43.48, H 7.25, N 18.00

The following compounds were synthesized using methods substantially equivalent to those described in Example 1 above or as described elsewhere herein.

EXAMPLE 2

Preparation of D-Prolinyl-L-Prolinyl-L-Arginine Aldehyde Dihydrochloride (D-Pro-Pro-Arg-H.2HCl)

Elemental Analysis Calculated for $C_{16}H_{30}N_6O_3Cl_2$: C, 45.18; H, 7.11; N, 19.76 Found: C, 44.96, H, 6.90, N, 19.56

EXAMPLE 3

Preparation of D-Homoprolinyl-L-Azetidinyl-L-Arginine Aldehyde Dihydrochloride (D-hPro-Azt-Arg-H.2HCl)

Elemental Analysis Calculated for $C_{16}H_{34}N_6O_5Cl_2$: C, 41.65; H, 7.43; N, 18.22 Found: C, 42.05, H, 7.35, N, 18.37

EXAMPLE 4

Preparation of D-Thiazolidinyl-4–Carbonyl-L-Prolinyl-L-Arginine Aldehyde Dihydrochloride FAB-MS 371 (MH+) $[\alpha]_D$ −36.2° (C=0.5/0.1N HCl)

EXAMPLE 5

Preparation of D-2-Isopropyl-5,5-Dimethylthiazolidinyl-4-Carbonyl-L-Prolinyl-L-Arginine Aldehyde Dihydrochloride A) D-2,2,5,5-Tetramethylthiazolidine A solution of D-penicillamine (29.8 g, 0.2 mol) in acetone (1800 mL) was reacted with 12N HCl (18.3 mL) at 50° C. for 4 hours. The reaction mixture was filtered, the filtrate was concentrated down in vacuo to 1500 mL and was allowed to stand at 4° C. for 24 hours. The solid was filtered and dried to give pure title compound (39.1 g, 86 percent yield): mp=188°–191°

B) D-5,5-Dimethyl-2-isopropylthiazolidine

A solution of D-2,2,5,5 tetramethylthiazolidine (A) (11.25 g, 0.050 mol) was dissolved in dioxane (150 mL), isobutyraldehyde (14 mL, 0.153 mol) was added and the reaction mixture heated 2 hours at reflux. The reaction mixture was cooled to room temperature and allowed to stand for 24 hours. The precipitate was filtered, and re-crystallized from ethanol (EtOH) (45 mL)/diethyl ether (125 mL) to afford pure title compound (9.0 g, 77 percent yield): mp=214°–216° C.

C) D-2-Isopropyl-5,5-dimethylthiazolidinyl-4-carbonyl-L-prolinyl-L-arginine Aldehyde Dihydrochloride By substantially following the procedures of Steps B through H of Example 1, the title compound was prepared FAB-MS 441 (MH+) $[\alpha]_D$ −88.4° (C=0.5/0.01N HCl)

Elemental Analysis Calculated for $C_{20}H_{40}N_6O_4Cl_2S$: C, 45.20; H, 7.57; N, 15.81; S, 6.03 Found: C, 45.44; H, 7.39; N, 15.86; S, 5.87

EXAMPLE 6

Preparation of trans-4-(2-Naphthyloxy)-D-Prolinyl-L-Prolinyl-L-Arginine Aldehyde Trihydrochloride Monohydrate A) N-Cbz-cis-4-hydroxy-D-proline methyl ester A 5° C. solution of (30 g; 229 mmol) of cis-4-hydroxy-D-proline in 115 mL of 2N aq NaOH was treated simultaneously with 36 mL (252 mmol) of benzyl chloroformate and 115 mL of 2N aq NaOH. After the pH of the reaction had stabilized, the mixture was washed with $Et_2O$ (2×150 mL) and was acidified to pH 2 with 5N aq HCl. The reaction was extracted EtOAc (4×200 mL) and the combined EtOAc extracts were dried over $Na_2SO_4$ and evaporated in vacuo to give 64.1 g of the crude N-Cbz-protected acid as a gum.

A mixture of the crude acid and 33.0 g (239 mmol) of $K_2CO_3$ in 300 mL of DMF was treated with 14.5 mL (233 mmol) of MeI in a dropwise manner. After stirring for 54 hours at room temperature, the reaction was poured into 300 mL of $H_2O$ and the mixture extracted with EtOAc (5×200 mL). The combined organic extracts were washed with $H_2O$ (3×200 mL), were dried over $Na_2SO_4$ and were evaporated in vacuo to give 65.3 g of an oil. Purification by flash chromatography ($SiO_2$; 25 percent EtOAc in hexanes) afforded 47.3 g (169 mmol; 74 percent from cis-4-hydroxy-D-proline) of the title compound as a viscous oil.

FD-MS, m/e 279 ($M^+$)

Elemental Analysis Calculated for $C_{14}H_{17}NO_5$: C 60.21, H 6.13, N 5.01; Found: C 59.95, H 6.11, N 4.92

B) N-Cbz-trans-4-(2-naphthyloxy)-D-proline methyl ester

A solution of 15.0 g (53.7 mmol) of N-Cbz-cis-4-hydroxy-D-proline methyl ester, 11.3 g (78.4 mmol) of $\beta$-naphthol, and 20.5 g (78.2 mmol) of triphenylphosphine in 300 mL of THF was treated with 12.3 mL (78.1 mmol) of diethyl azidodicarboxylate over 0.5 hour. The reaction was stirred at room temperature for 18 hours and was quenched by the addition of 100 mL sat'd aq NaCl. The two layers were separated and the organic solution dried ($Na_2SO_4$). Evaporation of the solvent gave 46.2 g of an oil which was purified by flash chromatography ($SiO_2$; gradient of 25 percent to 50 percent EtOAc in hexanes) to afford 15.2 g (37.5 mmol; 70 percent) of the title compound.

FD-MS, m/e 405 ($M^+$)

IR (film) 3014, 1749, 1705, 1630, 1422, 1357, 1179, 1121 $cm^{-1}$.

Elemental Analysis Calculated for $C_{24}H_{23}NO_5$: C 71.10, H 5.72, N 3.46; Found: C 71.04, H 5.73, N 3.59

C) trans-4-(2-naphthyloxy)-D-Proline-L-Proline-L-Arginine Aldehyde Trihydrochloride Monohydrate By substantially following the procedures of Example 1 except using lithium tri-t-butoxyalumino hydride, rather than lithium aluminum hydride, to reduce the coupled aminoprotected Arg lactam, N-Cbz-trans-4-(2-naphthyloxy)-D-Proline methyl ester was converted to the title compound which was isolated as the trihydrochloride monohydrate.

FAB-MS 495 ($MH^+$)

Elemental Analysis Calculated for $C_{26}H_{39}C_{13}N_6O_5$: C 50.21, H 6.32, N 13.51; Found: C 50.11, H 6.07, N 13.72

$[\alpha]_D = -5.11$ (C=0.01 MeOH).

EXAMPLE 8

Preparation of DL-cis-3-aza-bicyclo[5.4.0]undecanyl-2-carbonyl-L-prolinyl-L-arginine aldehyde dihydrochloride

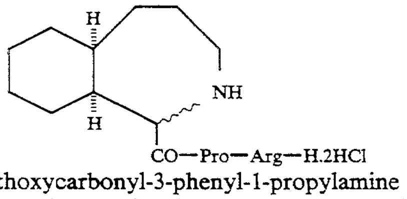

A) N-methoxycarbonyl-3-phenyl-1-propylamine

A stirred solution of 3-phenyl-1-propylamine (19.6 g, 145 mmol) in THF (50 mL) and water (50 mL) was adjusted to pH 9.0 with 2N NaOH. To the reaction was added methyl chloroformate (12.3 mL, 159 mmol) dropwise while the pH was maintained at 9.0 with 2N NaOH. After the reaction was stirred for an additional 30 minutes at room temperature, ethyl acetate (250 mL) was added. The organic layer was separated, dried ($MgSO_4$), filtered, and the filtrate was concentrated in vacuo to give a clear oil of pure title compound (28 g, 100 percent yield)

FAB-MS 193 ($M^+$);

TLC $R_f$(C) 0.83.

B) Moc-DL-2-carboxy-3,4-benzohomopiperidine

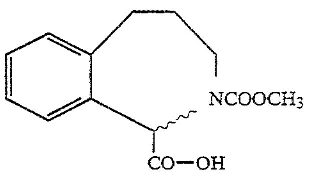

To a solution of N-methoxycarbonyl-3-phenyl-1-propylamine (A) (24.1 g, 125 mmol) in trifluoroacetic acid (125 mL) was added glyoxylic acid (11.1 g, 150 mmol) and heated to reflux temperature. After 4 hours at reflux the reaction was cooled to room temperature, the solvent was removed in vacuo, and diethylether (200 mL) / water (50 mL) was added to the residue. The reaction mixture pH was raised to 9.3 with 5N NaOH and the aqueous layer was separated. To the aqueous layer was added ethyl acetate (250 mL), and the solution was acidified to pH 2.5 with 3N HCl. The organic layer was separated, dried ($MgSO_4$), filtered, and the filtrate was concentrated in vacuo to afford an oil of pure title compound (26.9 g, 86 percent yield);

FAB-MS 250 ($MH^+$);

Elemental Analysis Calculated for $C_{13}H_{15}NO_4$: C 62.64, H 6.07, N 5.62 Found: C 62.72, H 6.02, N 5.87 c) Moc-DL-cis-3-aza-2-carboxybicyclo [5,4,0 ]undecane

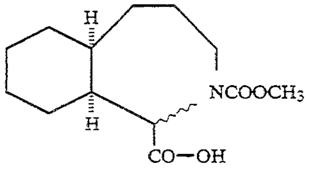

A solution of B (31.5 g, 126 mmol) in EtOH (400 mL) was reacted with hydrogen over 5 percent Rh / $Al_2O_3$ (16.0 g) at 2000 psi in a high pressure apparatus at 160° C. for 16 hours. The reaction mixture was filtered through a Celite® pad, and the filtrate was concentrated in vacuo to give pure title compound (27.8 g, 87 percent yield)

FAB-MS 256 ($MH^+$).

D) Cbz -DL-cis-3-aza-2-carboxybicyclo [5,4,0 ]undecane

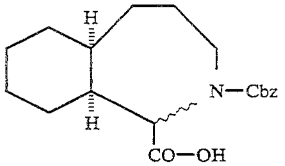

To a stirred solution of C (27.8 g, 109 mmol), at room temperature, in anhydrous $CH_3CN$ (200 mL) under an inert atmosphere was added a solution of iodotrimethyl silane (35.7 mL, 250 mmol) in $CH_3CN$ (20 mL). The reaction was stirred at 45° C. for 30 minutes and cooled to room temperature. The reaction was quenched with water (200 mL) followed by sodium metabisulfite (1 g). The pH of the reaction was raised to 9.5 with 5N NaOH and benzyl chloroformate (14.4 mL, 101 mmol) was added dropwise while the pH maintained at 9.5 with 2N NaOH. After the reaction was stirred for an additional 30 minutes at room temperature the organic solvent was evaporated in vacuo, and ethyl acetate (200 mL) was added, and the solution was acidified to pH 2.5 with 5N HCl. The organic layer was separated, dried ($MgSO_4$), filtered, and the filtrate was concentrated in vacuo to give a crude oil (31.8 g). The crude oil was purified by chromatography on silica gel using a step gradient elution ($CHCl_3$ 100 percent to $CHCl_3$ / EtOAc 1:1) to yield an oil (18.2 g, 50 percent yield). To a stirred, cooled (0° C.) solution of the oil (18.2 g) in THF (100 mL) and water (50 mL) was added 2N NaOH (25.3 mL, 50.6 mmol). The reaction was stirred 24 hour at room temperature. The reaction was diluted with diethylether (200 mL) and water (100 mL). The aqueous layer was separated, EtOAc (200 mL) was added, and the solution was acidified to pH 2.0 with 5N HCl. The organic layer was separated, dried ($MgSO_4$), filtered, and the filtrate was concentrated in vacuo to give pure title compound as an oil (6.9 g, 40 percent yield);

FAB-MS 332 (MH+);

Elemental Analysis Calculated for $C_{19}H_{25}NO_4$: C 68.86, H 7.60, N 4.23 Found: C 68.26, H 7.57, N 4.12

E) Cbz-DL-cis-3-aza-bicyclo[5,4,0] undecanyl-2-carbonyl-Pro-O-t-butyl

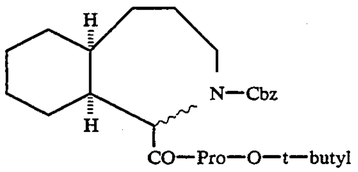

To a stirred, cooled (0° C.) solution of D (6.7 g, 20.2 mmol) in DMF (60 mL) was added L-Pro-O-t-butyl (3.46 g, 20.2 mmol), HOBT (2.73 g, 20.2 mmol), and DCC (4.17 g, 20.2 mmole). The reaction mixture was stirred for 2 hours at 0° C. and warmed to room temperature and stirred (24 h). The reaction mixture was concentrated to dryness in vacuo and the residue was dissolved in EtOAc. The organic solution was washed sequentially with 1N $NaHCO_3$ (100 ml), water, 1.5N citric acid, and water. The organic layer was dried ($MgSO_4$), filtered, and concentrated to dryness in vacuo to give the title pure compound (9.2 g, 94 percent yield):

TLC $R_f$(A) 0.74;

FAB-MS 484 (M+).

F) Cbz-DL-cis-3-aza-bicyclo[5,4,0] undecanyl-2-carbonyl-Pro-OH

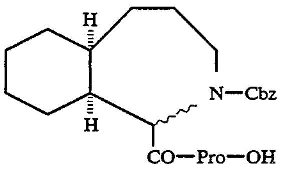

To a stirred, cooled (0° C.) solution of E (9.2 g, 19 mmole) in $CH_2Cl_2$ (20 mL), anisole (2.5 ml) was added trifluoroacetic acid (50 ml). The reaction was stirred 1 hour at room temperature. The reaction was concentrated in vacuo without heating and diluted with diethylether (200 mL) and water (200 mL). The pH of the solution was adjusted to 9.8 with 5N NaOH. The aqueous layer was separated, ethyl acetate (250 mL) was added, and the solution was acidified to pH 2.8 with 5N HCl. The organic layer was separated, dried ($MgSO_4$), filtered, and the filtrate was concentrated in vacuo to give the title compound (7.7 g, 95 percent yield) as a clear oil.

TLC $R_f$(A) 0.75;

FAB-MS 429 (MH+).

G) Cbz-DL-cis-3-azabicyclo[5,4,0] undecanyl-2-carbonyl-Pro-Arg(Cbz)lactam

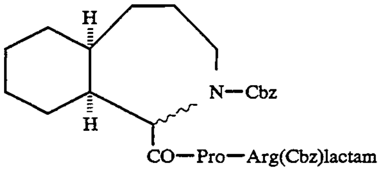

In flask 1 compound F (7.4 g, 17.3 mmole) was dissolved in DMF (50 ml), cooled to −15° C., and N-methylmorpholine (1.9 ml, 17.3 mmole) was added followed by isobutylchloroformate (2.3 ml, 17.3 mmole). The reaction mixture was stirred at −15° C. for 2 minutes. In flask 2 HCl.Arg(Cbz)-Lactam (5.7 g, 17.3 mmole) prepared substantially as described in Example 1, steps D and E, was dissolved in DMF (40 ml), cooled to 0° C., and diisopropylethylamine (7.5 ml, 43.2 mmole) was added to the solution. The reaction mixture was stirred at 0° C. for 2 minutes.

The contents of flask 2 was added to flask 1, and the reaction mixture was stirred for 2 hours (−15° C.) followed by 24 hour at room temperature. The reaction solvent was removed in vacuo to an oil. The residue was dissolved in EtOAc (200 ml) and washed sequentially with 1N $NaHCO_3$ (100 ml), water, 1.5N citric acid, and water. The organic solution was dried ($MgSO_4$), filtered, and concentrated to dryness in vacuo to give a crude solid. The crude solid was purified by chromatography on silica gel using a step gradient elution (hexanes 100 percent to hexane-EtOAc 20:80) to yield as the slower running material pure title compound (2.1 g, 17 percent yield):

FAB-MS 701 (MH+);

Elemental Analysis Calculated for $C_{38}H_{48}N_6O_7$: C 65.12, H 6.90, N 11.99 Found: C 65.58, H 7.26, N 11.13

H) Cbz-DL-cis-3-aza-bicyclo[5,4,0 ]undecanyl-2-carbonyl-Pro-Arg(Cbz)aldehyde

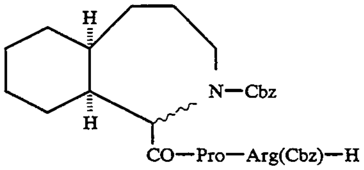

To a stirred, cooled (−70° C.) solution of G (2.1 g, 3.0 mmol) under a $N_2$ atmosphere in anhydrous THF (30 mL) was added lithium aluminum hydride 1M in THF (3.0 mL, 3.0 mmol). The reaction was stirred for 30 min at −70° C. A solution of 5 mL of THF and 5 mL of 0.5N $H_2SO_4$ was added dropwise to the reaction. The reaction was diluted with EtOAc (100 mL) and water (50 mL). The organic layer was separated, dried ($MgSO_4$), and filtered. The organic solvent was removed in vacuo to give an amorphous solid of the title compound (2.0 g, 95 percent):

FAB-MS 703 (MH+).

I) DL-cis-3-aza-bicyclo[5,4,0]undecanyl-2-carbonyl-L-prolinyl-L-arginine aldehyde dihydrochloride

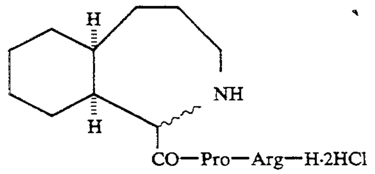

Compound H (2.0 g 2.8 mmol) dissolved in ethanol (120 mL), water (30 mL), and 1N HCl (7.0 mL, 7.0 mmol) was hydrogenated in the presence of 5 percent Pd/C catalyst (1.5 g) at ambient temperature and pressure. After the reaction was completed, the catalyst was removed by filtration. The filtrate was concentrated down to 30 mL in vacuo and water (50 mL) was added. The pH of the solution was adjusted to 4.0 with BioRad AG1-X8 resin (hydroxide form). The resin was removed by filtration and the solution lyophilized to give the title compound (1.27 g, 89 percent):

FAB-MS 435 (MH+);

Elemental Analysis Calculated for $C_{22}H_{38}N_6O_3$.2HCl.3$H_2O$: C 46.31, H 8.30, N 14.73 Found: C 46.10, H 7.94, N 14.43.

EXAMPLE 9

Preparation of D,L-Piperazin-2-yl-L-Prolinyl-L-Arginine Aldehyde Dihydrochloride The title compound was prepared from D,L-piperazine-2-carboxylic acid dihydrochloride by substantially following the procedures of Example 1 except using lithium tri-t-butoxyaluminohydride, rather than lithium aluminum hydride, to reduce the coupled amino-protected Arg lactam.

FAB-MS, m/e 368 (MH+)

Elemental Analysis Calculated for $C_{16}H_{31}Cl_2N_7O_3$: C 43.64, H 7.10, N 22.26; Found: C 43.17, H 7.78, N 15.21

EXAMPLE 10

Preparation of D,L-Thiazolidinyl-2-carbonyl-L-prolinyl-L-arginine aldehyde dihydrochloride A) Cbz-D,L-thiazolidinyl-2-carbonyl-L-prolinyl-L-Arginyl Lactam The title compound was prepared from D,L-thiazolidinyl-2-carboxylic acid by substantially following the procedures described in Example 9.

FD-MS: m/e 636 (M+)

Elemental Analysis Calculated for $C_{31}H_{36}N_6O_7S$: C 58.48, H 5.70, N 13.20. Found: C 58.49, H 5.57, N 12.95

$[\alpha]_D = -74.26°$ (C=0.01 $CH_2Cl_2$)

B) Cbz-D,L-thiazolidinyl-2-carbonyl-L-Proline-Cbz-L-Arginine Aldehyde

A −25° C. solution of 12.3 g (19.0 mmol) of Cbz-D,L-thiazolidinyl-2-carbonyl-L-prolyinyl-L-arginyl lactam in 200 mL THF was treated with 29 mL (1M in THF; 29 mmol) of Li(t-BuO)$_3$AlH solution at a rate that did not warm the reaction temperature to above −20° C. The reaction was stirred at −25° C. for 3 hours and was poured into 100 mL HCl. The mixture was extracted with 1:1 THF-hexane (2×100 mL) and EtOAc (2×100 mL). The EtOAc layer was dried over $Na_2SO_4$ and evaporated in vacuo to afford 6.96 g (10.9 mmol; 58 percent yield) of the crude product as a white foam. The presence of the desired product was confirmed by mass spec. [FD-MS; m/e 638 (M+)] and the mixture taken on to the next reaction without further purification.

C) D,L-thiazolidinyl-2-carbonyl-L-prolinyl-L-arginine aldehyde dihydrochloride

To a mixture of the protected aldehyde (B) (6.72 g; 10.5 mmol) and p-cresol (7.0 mL) was added 35 mL of liquid HF in a Teflon/Kel-F apparatus. The mixture was stirred at 0° C. for 20 min, and then the HF was removed in vacuo. The residue was triturated with $Et_2O$ to give a white solid which was purified by reverse phase chromatography using a 5×25 cm Vydac $C_{18}$ RP-HPLC column using a gradient of 2 percent $CH_3CN$ in 0.5 percent aq HCl to 40 percent $CH_3CN$ in 0.5 percent aq HCl. The pure fractions were combined and lyopholized to afford 2.65 g (6.0 mmol; 60 percent) of the title compound as the dihydrochloride.

FAB-MS, m/e 370 (M+)

Elemental Analysis Calculated for $C_{15}H_{28}Cl_2N_6O_3S$: C 40.63, H 6.37, N 18.95 Found: C 40.84, H 6.19, N 18.80

EXAMPLE 11

Preparation of D,L-thiomorpholinyl-2-carbonyl-L-Proline-L-Arginine Aldehyde Dihydrochloride The title compound was prepared by substantially following the procedure used in the synthesis of D,L-thiazolidinyl-2-carbonyl-L-proline-arginine aldehyde dihydrochloride (Example 10).

FAB-MS m/e 385 (M+)

Elemental Analysis Calculated for $C_{16}H_{30}Cl_2N_6O_3S$: C 42.01, H 6.61, N 18.37 Found: C 40.73, H 6.73, N 15.09

$[\alpha]_D = -58.43°$ (C=0.01 MeOH).

EXAMPLE 12

Preparation of D-Cis-(4-phenoxy)Prolinyl-L-Prolinyl-L-Arginine Aldehyde Trihydrochloride Monohydrate By substantially following the procedures of Example 6, the title compound was prepared.

Elemental Analysis Calculated for $C_{22}H_{32}N_6O_4$.3HCl.3HCl.$H_2O$ C 46.20, H 6.52, N 14.69 Found: C 46.04, H 6.73, N 14.44

FAB-MS 445 (MH+)

EXAMPLE 13

Preparation of 4-(3-pyridyloxy)-D-prolinyl-L-prolinyl-L-arginine aldehyde hydrochloride hydrate A) N-CBz-trans-4-(3-pyridyloxy)-D-Proline Methyl Ester The title compound was prepared from 3-hydroxy pyridine and N-Cbz-cis-4-hydroxy-D-proline methyl ester by substantially following the procedure used in the preparation of N-Cbz-trans-4-(2-naphthyloxy)-D-proline methyl ester, Example 6, Steps A and B.

FD-MS 356 (M+)

Elemental Analysis Calculated for $C_{19}H_{20}N_2O_5$: C 64.04, H 5.66, N 7.86 Found C 64.22, H 5.81, N 7.76

B) 4-(3-pyridyloxy)-D-Proline-L-Proline-Arginine Aldehyde Hydrochloride Hydrate

The title compound was prepared from N-Cbz-trans-4-(3-pyridyloxy)-D-proline methyl ester by substantially following the procedures of Example 9.

FAB-MS 368 (M+)

Elemental Analysis Calculated for $C_{21}H_{34}ClN_7O_5$: C 50.45, H 6.38, N 19.61 Found C 50.62, H 6.61, N 19.60

EXAMPLE 14

Preparation of trans-4-phenylthio-D-prolinyl-L-prolinyl-L-arginine aldehyde trihydrochloride trihydrate A) N-Cbz-cis-4-tosyl-D-proline methyl ester A solution of 20 g (71.6 mmol) of N-Cbz-cis-4-hydroxy-D-proline methyl ester, 15 mL (107 mmol) of triethylamine and 0.4 g (3.3 mmol) of 4-dimethylaminopyridine in 200 mL of $CHCl_3$ was treated with 15.1 g (79.2 mmol) of p-toluenesulfonyl chloride in portions. The reaction was stirred at room temperature for 18 hours and was washed successively with 100 mL of $H_2O$, 100 mL of 1N aqueous citric acid, and 100 mL of $H_2O$. The organic fraction was dried over $Na_2SO_4$ and evaporated in vacuo to give 31.4 g of an oil which was purified by flash chromatography ($SiO_2$; 50 percent EtOAc in hexanes) to afford 18.2 g (42 mmol; 59 percent) of the title compound as a white solid.

FD-MS, m/e 433 ($M^+$)

Elemental Analysis Calculated for $C_{21}H_{23}NO_7S$: C 58.19, H 5.35, N 3.23 Found: C 58.43, H 5.33, N 3.16

B) N-Cbz-trans-4-Phenylthio-D-Proline ethyl ester

Thiophenol (3.3 mL; 32.2 mmol) was added to a solution of 35.6 mmol of sodium ethoxide in 40 mL EtOH (generated from adding 820 mg of Na to 40 mL EtOH). The mixture was stirred for 15 min and was treated with 6.0 g (15 mmol) of solid N-Cbz-cis-4-tosyl-D-proline methyl ester. The reaction was stirred at 40° C. for 19 hours at which time it was cooled and diluted with 100 mL of $H_2O$. The EtOH was evaporated in vacuo and the aqueous layer extracted with EtOAc (3×100 mL). The combined organic extracts were dried over $Na_2SO_4$ and evaporated in vacuo to give 7.40 g of an oil which was purified by flash chromatography ($SiO_2$; 5 percent EtOAc in hexanes) to afford 4.60 g (12 mmol; 79 percent) of the title compound as a clear oil.

FD-MS, m/e 385 ($M^+$)

Elemental Analysis Calculated for $C_{14}H_{17}NO_5$: C 65.43, H 6.01, N 3.63 Found C 65.39, H 6.01, N 3.85

C) trans-4-Phenylthio-D-Proline-L-proline-Arginine Aldehyde Trihydrochloride Trihydrate The title compound was prepared from N-Cbz-trans-4-phenylthio-D-proline ethyl ester by substantially following the procedures used in the synthesis of D,L-thiazolidinyl-2-carbonyl-L-Proline-L-Arginine Aldehyde dihydrochloride, Example 10.

FAB-MS m/e 461 ($M^+$).

High Resolution Mass Spec. (HRMS) ($MH^+$), $C_{22}H_{33}N_6O_3S$. Theory 461.2341, Found 461.2318.

Elemental Analysis Calculated for $C_{22}H_{35}Cl_3N_6O_3S.3H_2O$: C 42.35, H 6.62, N 13.47 Found C 42.46, H 5.73, N 13.53

EXAMPLE 15

Preparation of N-methyl-3-amino-3-phenylpropionyl-L-Prolinyl-L-Arginine Aldehyde Dihydrochloride Dihydrate A) D,L-N-Cbz-3-amino-3-phenyl propionic acid.

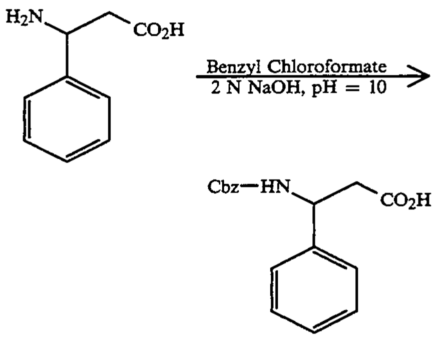

A 0° C. slurry of 50.0 g (300 mmole) of DL-3-amino-3phenyl propionic acid in 300 mL of 1N aq NaOH (300 mmole) was treated simultaneously with 48.0 mL (340 mmole) of benzyl chloroformate and 300 mL of 1N aq NaOH (300 mole). The reaction was stirred at ambient temperature for 18 h at which time the reaction was acidified to pH 2 with conc. aq HCl and extracted with EtOAc (4×200 mL). The combined organic fractions were dried over $Na_2SO_4$ and evaporated in vacuo to give 73.4 g (250 mmol; 82%) of N-Cbz-3-amino-3-phenyl propionic acid as an off white solid.

FD-MS, m/e 299 ($M^+$, 100).

IR (KBr) 3362, 3038, 1697, 1532, 1289, 1231, 1028, 699 $cm^{-1}$. Analytical Calculated for $C_{17}H_{17}NO_4$: C 68.22, H 5.72, N 4.68 Found: C 68.51, H 5.81, N 4.90

B) D,L-N-methyl-N-cbz-3-amino-3-phenyl propionic acid.

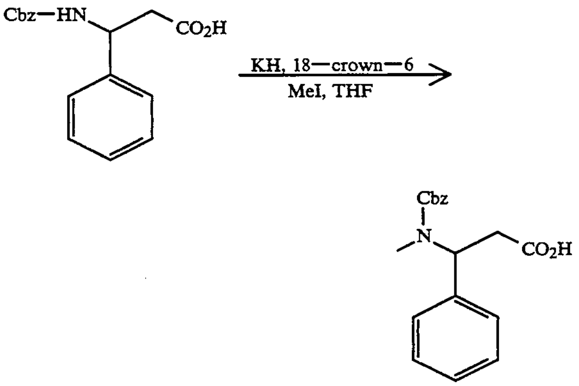

A solution of 22.8 g (76 mmol) of N-Cbz-3-amino-3-phenyl propionic acid in 50 mL THF was added to a 0° C. slurry of 36.6 g (230 mmole; 25% suspension in mineral oil) of KH and 1.0 g (4 mmol) of 18-crown-6 at a rate that kept the reaction temp below 10° C. A solution of MeI (86.3 g; 610 mmol in 50 mL THF was added dropwise and the reaction stirred at 10° C. for 3 h. The reaction was quenched with 15 mL of acetic acid and was poured into 200 mL $H_2O$. The aqueous pool was adjusted to pH 10 with 5N aq NaOH and washed with $Et_2O$ (2×100 mL). The aqueous layer was acidified to pH 4 with 5N aq HCl and extracted with EtOAc (4×200 mL). The combined EtOAc layers were dried over $MgSO_4$ and evaporated in vacuo to give 15.6 g of an orange oil which was purified by flash chromatography ($SiO_2$; 5% MeOH in $CHCl_3$) to afford 10.5 g (33.5 mmol; 45%) of N-methyl-N-Cbz-3-amino-3-phenyl propionic acid as a clear oil.

$^1H$ NMR ($CDCl_3$) δ 10.05-7.90 (broad, 1H), 5.95-5.78 (m, 1H), 5.20 (s, 2H), 3.04 (d, J=6.7 Hz), 2.74 (s, 3H).

FD-MS m/e 313 (M+, 100).

C) N-Methyl-N-Cbz-3-amino-3-phenyl propionyl-L-Pro-benzyl ester.

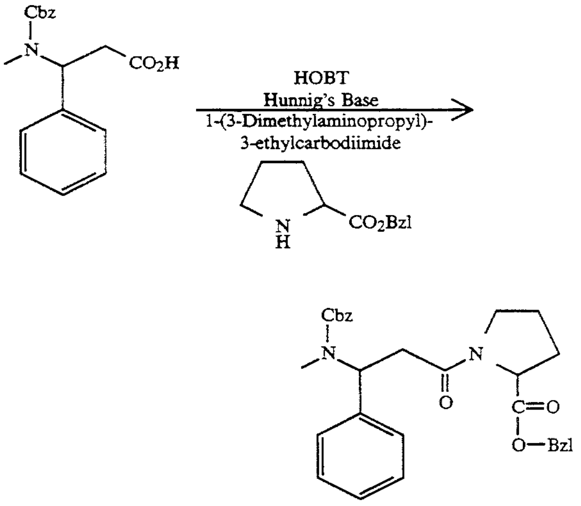

A 5° C. solution of 10.5 g (33.5 mmol) of N-methyl-N-cbz-3-amino-3-phenyl propionic acid, 8.12 g (33.5 mmol) of L-proline benzylester, and 4.53 g (33.5 mol) of 1-hydroxybenzotriazole hydrate in 300 mL of THF was treated with 12.96 g (100 mmol) of diisopropylethylamine and 7.08 g (36.9 mmol) of 1-(3-dimethylamino-propyl)-3-ethylcarbodiimide hydrochloride. The mixture was stirred at 5° C. for 30 min and allowed to warm to ambient temperature over 66 hrs. The solvent was evaporated in vacuo and the residue diluted with 500 mL of EtOAc. The mixture was washed successively with 1N aq. HCl (2×), sat'd aq. $NaHCO_3$ (2×), and brine. The organic layer was dried over $Na_2SO_4$ and evaporated in vacuo to give a colorless oil which was purified by flash chromatography ($SiO_2$; 10% EtOAc in $CH_2Cl_2$) to afford 12.88 g (25.8 mmol; 77%) of N-methyl-N-Cbz-3-amino-3-phenyl propionyl-L-Pro-benzyl ester as a clear oil.

IR ($CHCl_3$) 3025, 3019, 3013, 1741, 1690, 1645, 1453 $cm^{-1}$.

FD-MS, m/e 500 (M+, 100).

Analytical Calculated for $C_{30}H_{32}N_2O_5$: C 71.98, H 6.44, N 5.60 Found: C 72.11, H 6.54, N 5.60

$[\alpha]_D = -43.1°$ (c=0.01, MeOH).

D) N-methyl-N-Cbz-3-amino-3-phenyl propionyl-L-Pro-Arg-(Cbz) lactam.

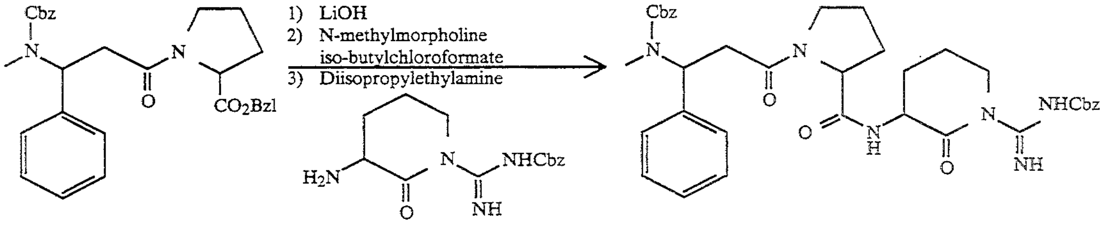

A solution of 12.5 g (25 mmol) of N-methyl-N-Cbz-3-amino-3-phenyl propionyl-L-Pro-benzyl ester in 200 mL dioxane was treated with 5.23 g (125 mmol) of LiOH followed by 100 mL of $H_2O$. The reaction was stirred at RT for 16 h at which time the dioxane was evaporated in vacuo. The cloudy mixture was diluted with 20 mL $H_2O$ and was extracted with $CH_2Cl_2$ (2×). The aqueous layer was acidified to pH 2 with 5N aq HCl and was extracted with $CHCl_3$ (3×). The combined chloroform extracts were evaporated in vacuo to give 9.85 g of the crude corresponding acid as a white foam. The presence of the desired product was confirmed by FD-MS (m/e 411, M+1, 100) and the mixture taken on directly to the next reaction.

A −15° C. solution of 9.65 g of the crude acid in 100 mL THF was treated with 2.38 g (23 mmol) of N-methylmorpholine followed by 3.20 g (23 mmol) of isobutylchloroformate. The mixture was stirred for 5 min and was treated with a solution of 8.54 g (23 mmol) of the arg-lactam and 6.07 g (46 mmol) of diisopropylethylamine in 300 mL of a 2:1 mixture of DMF and THF. The reaction was allowed to reach ambient temperature overnight at which time 15 mL of 1N aq. $NaHCO_3$ was added. The solvent was evaporated in vacuo and the resulting oil partitioned between 200 mL EtOAc and 100 mL $H_2O$. The organic layer was separated and was washed successively with 1M aq $NaHSO_4$, $H_2O$, saturated aq $NaHCO_3$, and brine. The organic phase was dried over $Na_2SO_4$ and evaporated in vacuo to give a white foam which was purified by flash chromatography ($SiO_2$: 30% $CH_3CN$ in $CH_2Cl_2$) to afford 6.96 g (10 mmol; 40% from N-methyl-N-Cbz-3-amino-3-phenyl propionyl-L-Pro-benzyl ester) of N-methyl-N-Cbz-3-amino-3-phenyl propionyl-L-Pro-Arg-(Cbz) lactam as a white foam.

FD-MS, m/e 683 (MH+).

IR ($CHCl_3$) 3373, 3012, 1687, 1614, 1499, 1266, 1180 $cm^{-1}$.

Analytical Calculated for $C_{37}H_{42}N_6O_7$: C 65.09, H 6.20, N 12.31 Found: C 65.31, H 6.37, N 11.85

$[\alpha]_D = -52.8°$ (c=0.01, $CH_2Cl_2$).

E) N-methyl-3-amino-3-phenyl propionyl-L-Pro-L-Arg-Aldehyde.

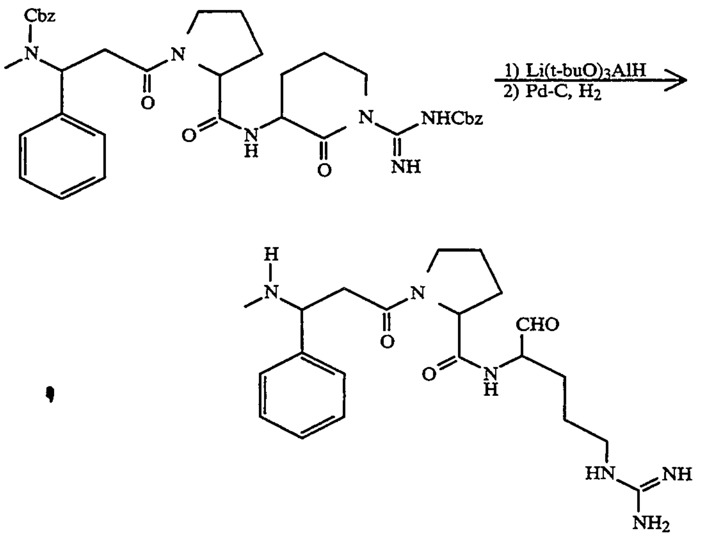

A −25° C. solution of 6.96 g (10 mmol) of N-methyl-N-Cbz-3-amino-3-phenyl propionyl-L-Pro-Arg-(Cbz) lactam in 120 mL THF was treated with 15 mL (15 mmol; 1M in THF) of $Li(t\text{-}BuO)_3AlH$ solution at a rate that did not warm the reaction temperature to above −20° C. The reaction was stirred at −25° C. for 2.5 h and was poured into 100 mL of 1N aq HCl. The mixture was extracted with a 1:1 mixture of THF:hexanes (2×300 mL) followed by EtOAc (2×300 mL). The combined EtOAc extracts were dried over $Na_2SO_4$ and evaporated in vacuo to give 6.88 g of a white foam. The presence of the desired product was confirmed by FD-MS (m/e 685, Mt) and the mixture taken on directly to the next reaction.

A solution of the crude reduction product in 300 mL of EtOH, 100 mL of $H_2O$ and 15 mL of 1N aq HCl was charged with 1.7 g of 5% Pd/C and the mixture treated with a stream of $H_2$ gas for 3 h. The catalyst was filtered and washed with 200 mL of a 3:1 EtOH:$H_2O$ mixture. The combined filtrates were evaporated in vacuo to 15 mL and diluted back to 75 mL with $H_2O$. The mixture was adjusted to pH 4 with AG 1-X8 anion exchange resin and was lyopholized to afford 3.6 g (6.9 mmol; 69% from N-methyl-N-Cbz-3-amino-3-phenyl propionyl-L-Pro-Arg-(Cbz) lactam) of N-methyl-3-amino-3-phenyl propionyl-L-Pro-L-Arg-aldehyde dihydrochloride dihydrate.

FAB-MS m/e 417 (MH+, 100).

IR (KBr) 3314, 2958, 1657, 1457, 703 $cm^{-1}$.

Analytical Calculated for $C_{21}H_{32}N_6O_3.2HCl.2H_2O$: C 48.00, H 7.29, N 15.99 Found: C 47.54, H 7.04, N 15.92

$[\alpha]_D = -90.3°$ (c=0.01, MeOH).

EXAMPLE 16

Preparation of N-methyl-3-amino-3-cyclohexyl propionyl-L-Pro-L-Arg aldehyde dihydrochloride hemihydrate.

A) N-Cbz-3-amino-3-cyclohexyl propionic acid.

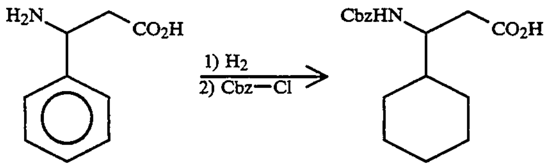

A solution of 25 g (151 mmol) of 3-amino-3-phenylproprionate in 450 mL of HOAc was charged with 25 g of 5% $Rh/Al_2O_3$ and the mixture hyrogenated at 60 psi for 30 hr at 60° C. The reaction was filtered over celite and evaporated in vacuo to a dark oil. The presence of the desired product was confirmed by FD-MS (m/e 172, MH+, 100). The crude reduction product was treated with benzylchloroformate (25.67 g; 151 mmol) under basic conditions substantially according to the procedures of Example 1, A, to afford 23.4 g of N-Cbz-3-amino-3-cyclohexyl propionic acid as a grey solid.

FD-MS, m/e 306 (MH+; 100)

IR ($CHCl_3$) 3438, 2932, 1715, 1751, 1451 $cm^{-1}$.

Analytical Calculated for $C_{17}H_{23}NO_4$: C 66.86, H 7.59, N 4.59 Found: C 66.56, H 7.65, N 4.41

B) N-methyl-N-Cbz-3-amino-3-cyclohexyl propionic acid.

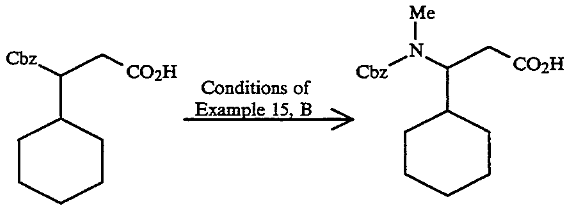

By substantially following the procedures of Example 15, B, 11.0 g (36.07 mmol) of N-Cbz-3-amino-3-cyclohexyl propionic acid was treated with KH and MeI to afford 24.76 g of crude methyl N-methyl-N-Cbz-3-amino-3-cyclohexyl propionate. The methyl ester was hydrolyzed to the corresponding acid substantially according to the procedures of Example 15, D, to afford 7.50 g of N-methyl-N-Cbz-3-amino-3-cyclohexyl propionic acid, as an oil.

FD-MS m/e 320 ($MH^+$, 100)

IR ($CHCl_3$) 3012, 2932, 1698, 1451, 1124, 986 $cm^{-1}$.

C) N-methyl-N-Cbz-3-amino-3-cyclohexyl-L-Pro-benzyl ester.

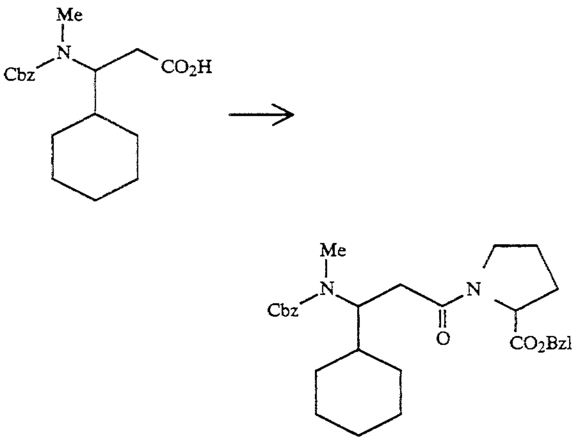

By substantially following the methods of Example 15, C, 8.6 g (27.0 mmol) of N-methyl-N-Cbz-3-amino-3-cyclohexyl propionic acid was coupled to L-proline benzyl ester. Purification of the crude product by flash chromatograpy ($SiO_2$; 10% EtOAc in $CH_2Cl_2$) afforded 5.80 g (11.5 mmol; 43%) of N-methyl-N-Cbz-3-amino-3-cyclohexyl-L-Pro-benzyl ester as a clear oil.

FD-MS, m/e 507 ($MH^+$; 100)

IR ($CHCl_3$) 3012, 2934,1742, 1689, 1451, 1172 $cm^{-1}$.

Analytical Calculated for $C_{30}H_{38}N_2O_5$: C 71.12, H 7.56, N 5.53 Found: C 71.30, H 7.61, N 5.69

D) N-methyl-N-Cbz-3-amino-3-cyclohexyl propionyl-L-Pro-Arg-(Cbz) lactam.

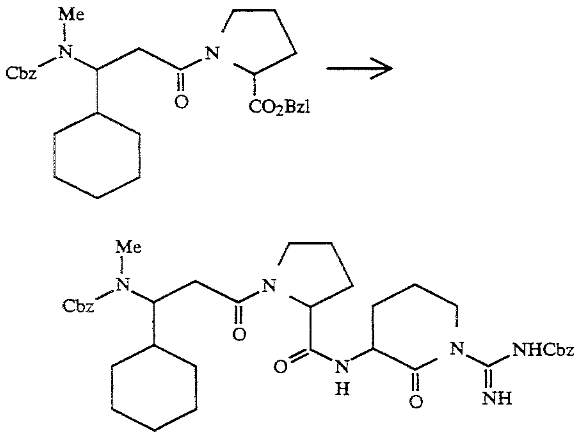

By substantially following the conditions of Example 15, D, 5.37 g (10.6 mmol) of N-methyl-N-Cbz-3-amino-3-cyclohexyl-L-Pro benzyl ester was hydrolyzed to afford 4.36 g of the corresponding acid. The presence of the desired acid was confirmed by FD-MS (m/e 417; Mtl, 100) and the crude product coupled to the Cbz-protected arg-lactam (3.80 g; 10.48 mmol). The coupled product was purified by flash chromatography ($SiO_2$; 75% EtOAc in $CH_2Cl_2$) to afford 4.24 g (6.17 mmol; 58% from N-methyl-N-Cbz-3-amino-3-cyclohexyl-L-pro-benzyl ester) of the title compound.

FD-MS, m/e 688 ($M^+$), 511 (100).

IR ($CHCl_3$) 3011, 2935, 1687, 1615, 14989, 1267, 1182 $cm^{-1}$.

Analytical Calculated for $C_{37}H_{48}N_6O_7$: C 64.52, H 7.02, N 12.20 Found: C 64.63, H 7.11, N 12.13

$[\alpha]_D = -51.8°$ (c=0.01, $CH_2Cl_2$).

E) N-methyl-3-amino-3-cyclohexyl propionyl-L-Pro-L-Arg Aldehyde.

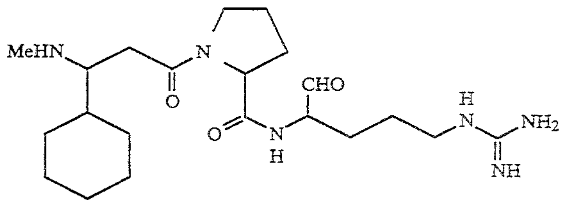

By substantially following the procedures of Example 15, E, 1.83 g (2.66 mmol) of N-methyl-N-Cbz-3-amino-3-cyclohexyl propionyl-L-Pro-Arg-(Cbz) lactam was reduced with lithium tri-t-butoxyaluminum hydride to afford 1.09 g of the crude protected arginal. Deprotection according to Example 15, E, gave 0.56 g (1.07 mmol; 40% over two steps) of N-methyl-3-amino-3-cyclohexyl propionyl-L-Pro-L-Arg Aldehyde as the dihydrochloride hemihydrate.

FAB-MS, m/e 423 ($M^+$; 100).

IR (KBr) 3347, 2932, 1657, 1450 $cm^{-1}$.

Analytical Calculated for $C_{21}H_{38}N_6O_3.2HCl.0.5H_2O$: C 50.17, H 8.14, N 16.96 Found: C 49.99, H 8.19, N 16.71

$[\alpha]_D = -49.3°$ (c=0.01 MeOH).

EXAMPLE 17

Preparation of N-Methyl-3-amino-2-benzylpropionyl-L-Pro-L-Arg Aldehyde Dihydrochloride Monohydrate.

A) Ethyl N-Cbz-3-amino-2-benzyl propionate.

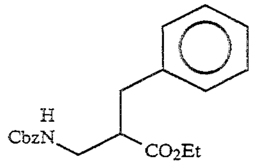

A solution of 21.0 g (103 mmol) of ethyl-2-cyano-3-phenylproprionate in 140 mL of EtOH was charged with 3.0 g of 5% Pd/C and 3.0 g of HCl (g). The resulting mixture was hydrogenated at 60 psi for 3 h at room temperature. The reaction was filtered through Celite® and evaporated to give 25.14 g of a dark viscous oil which was treated with benzylchloroformate (19.34 g; 113 mmol) under basic conditions substantially according to Example 15, A. Purification of the reaction mixture by flash chromatography ($SiO_2$; $CH_2Cl_2$) afforded 16.70 g (48.7 mmol; 49%) of ethylN-Cbz-3-amino-2-benzyl propionate as a clear oil.

FD-MS, m/e 341 ($M^+$; 100)

IR ($CHCl_3$) 3453, 3029, 1722, 1514, 1196 $cm^{-1}$.

Analytical Calculated for $C_{20}H_{23}NO_4$: C 70.36, H 6.79, N 4.10 Found: C 70.59, H 6.82, N 4.21

B) N-Cbz-3-amino-2-benzyl propionic acid.

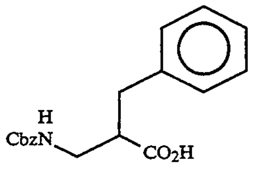

A sample of 16.60 g (48.68 mmol) of ethyl N-Cbz-3-amino-2-benzyl propionate was hyrdrolyzed substantially according to the conditions of Example 15, D, to afford 14.40 g (46.0 mmol; 94%) of a N-Cbz-3-amino-2-benzyl propionic acid as a white solid.

FD-MS, m/e 313 (M+; 100)

IR ($CHCl_3$) 3022, 1700, 1405, 1142 $cm^{-1}$.

Analytical Calculated for $C_{18}H_{19}NO_4$: C 68.99, H 6.11, N 4.47 Found: C 68.78, H 6.23, N 4.50

C. N-Methyl-N-Cbz-3-amino-2-benzyl propionic acid.

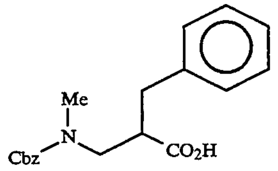

By substantially following the procedures of Example 15, B, 13.90 g (44.4 mmol) of N-Cbz-3-amino-2-benzyl propronic acid, was alkylated to afford 14.23 g of a mixture of the N-methylated carboxylic acid and the N-methylated methyl ester. The crude mixture was hydrolyzed substantially according to the conditions of Example 15, D, to afford 8.10 g of N-methyl-N-Cbz-3-amino-2-benzyl propionic acid. The presence of the desired product was confirmed by FD-MS (m/e 328, MH+, 100) and the crude material taken on directly to the next reaction.

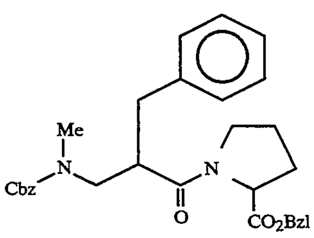

D) N-methyl-N-Cbz-3-amino-2-benzyl propionyl-L-Pro-benzyl ester.

By substantially following the methods described in Example 15, C, 8.07 g of crude N-methyl-N-Cbz-3-amino-2-benzyl propionic acid was coupled to proline benzyl ester. Purification of the reaction mixture by flash chromatography ($SiO_2$, 10% EtOAc in $CH_2Cl_2$) afforded 9.0 g (17.5 mmol; 39% from N-methyl-N-Cbz-3-amino-2-benzyl propionic acid) of N-methyl-N-Cbz-3-amino-2-benzyl propionyl-L-Pro-benzyl ester as a clear oil.

FD-MS, m/e 515 (MH+; 100)

IR ($CHCl_3$) 3010, 1742, 1694, 1638, 1451, 1172 $cm^{-1}$.

Analytical Calculated for $C_{31}H_{34}N_2O_5$: C 72.35, H 6.66, N 5.44 Found: C 72.60, H 6.75, N 5.42

$[\alpha]_D = -53.5°$ (c=0.01, MeOH).

E) N-Methyl-N-Cbz-3-amino-2-benzylpropionyl-L-Pro-Arg-(Cbz) lactam

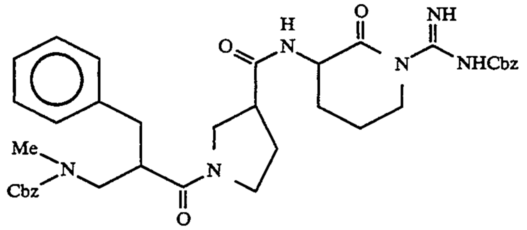

By substantially following the procedures of Example 15, D, 9.0 g (17.5 mmol) of N-methyl-N-Cbz-3-amino-3-phenyl propionyl-L-Pro-benzyl ester was hydrolyzed to afford 7.19 g of the corresponding acid. The presence of the desired product was confirmed by FD-MS (m/e 425; MH+, 100) and the crude mixture was coupled to the Cbz-protected Arg-lactam (6.05 g; 16.67 mmol). The crude product was purified by flash chromatography ($SiO_2$; 75% EtOAc in $CH_2Cl_2$) to afford 5.71 g (8.2 mmol 47% from N-methyl-N-Cbz-3-amino-3-phenyl propionyl-L-Pro-benzyl ester) of N-methyl-N-Cbz-3-amino-2-benzylpropionyl-L-pro-Arg-(Cbz) lactam.

FD-MS, m/e 698 (Mt2, 100).

IR ($CHCl_3$) 3376, 3012, 1699, 1615, 1498, 1267, 1181 $cm^{-1}$.

Analytical Calculated for $C_{38}H_{44}N_6O_7$: C 65.50, H 6.36, N 12.06 Found: C 65.31, H 6.39, N 12.08

$[\alpha]_D = -36.3°$ (c=0.01, $CH_2Cl_2$).

F) N-methyl-3-amino-2-benzylpropionyl-L-Pro-L-Arg Aldehyde dihydrochloride monohydrate

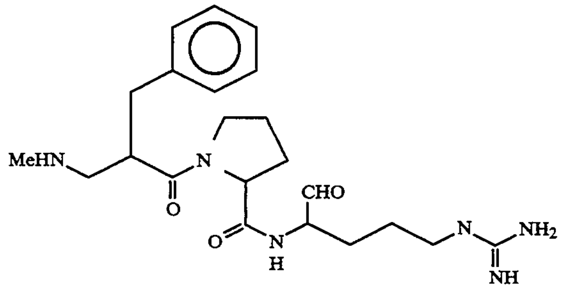

By substantially following the procedures of Example 15, E, 5.65 g (8.1 mmol) of N-methyl-N-Cbz-3-amino-2-benzylpropionyl-L-Pro-Arg-(Cbz)-lactam was reduced with lithium tri-t-butoxyaluminum hydride to afford 4.71 g of the crude protected arginal. Deprotection, again substantially according to the procedures of Example 15, E. gave 2.45 g of crude N-methyl- 3-amino-2-benzylpropionyl-L-Pro-L-Arg aldehyde. Purification by reverse phase chromatography yielded 1.51 g (2.9 mmol; 36% over two steps) of N-methyl-3-amino-2-benzylpropionyl-L-Pro-L-Arg aldehyde as the dihydrochloride monohydrate.

FAB-MS, m/e 431 (MH+; 100).

IR (KBr) 3390, 1653, 1453, 754 $cm^{-1}$.

Analytical Calculated for $C_{22}H_{34}N_6O_3.2HCl.H_2O$: C 50.67, H 7.34, N 16.11 Found: C 50.52, H 7.24, N 15.97

$[\alpha]_D = -103.8°$ (c=0.01, MeOH).

EXAMPLE 18

Preparation of 2-(2-Piperidino)acetyl-L-Pro-L-Arginine Aldehyde Dihydrochloride Monohydrate A) N-Cbz-2-(2-piperidino) acetic acid

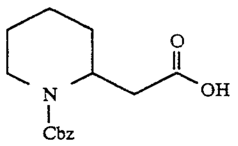

A solution of 24.5 g (140 mmol) of 2-pyridylacetic acid in 470 mL of EtOH was charged with 5.0 g of $PtO_2$ and the mixture hydrogenated at 60 psi for 6 hr at 40° C. The reaction was filtered through Celite ® and evaporated to give 29.72 g of a grey oil. The presence of the saturated acid was confirmed by FD-MS (m/e 144; Mt1, 100) and the crude reaction mixture was treated with benzylchloroformate (56.45 g; 332 mmol) under basic conditions substantially according to the procedures of Example 15, A, to afford 21.92 g (79.1 mmol; 56% of N-Cbz-2-piperidinoacetic acid as a clear oil.

FD-MS, m/e 277 (M+, 100).

IR ($CHCl_3$) 3011, 2947, 1714, 1690, 1428, 1265, $cm^{-1}$.

Analytical Calculated for $C_{15}H_{19}NO_4$: C 64.97, H 6.91, N 5.05 Found: C 65.20, H 6.88, N 5.34

B) N-Cbz-2-(2-piperidino) acetyl-L-Pro-benzyl ester

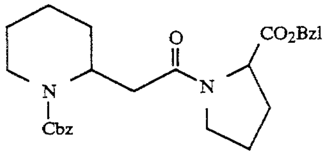

By substantially following the procedures of Example 15, C, 20.85 g (75 mmol) of N-Cbz-2-(2-piperidino)acetic acid was coupled to proline benzylester. The crude product was purified by flash chromatography ($SiO_2$; 10% EtOAc in $CH_2Cl_2$) to give 27.61 g (59.6 mmol; 79%) of N-Cbz-2-(2-piperidino)acetyl-L-Pro-benzyl ester as a clear oil.

FD-MS, m/e 464 (M+; 100)

IR ($CHCl_3$) 3013, 1742, 1685, 1425, 1263, 1172 $cm^{-1}$.

Analytical Calculated for $C_{27}H_{32}N_2O_5$: C 69.81, H 6.94, N 6.03 Found: C 69.82, H 7.10, N 6.02

$[\alpha]_D = -40.0°$ (c=0.01, MeOH).

C) N-Cbz-2-(2-piperidino) acetyl-L-Pro-Arg-(Cbz)-lactam

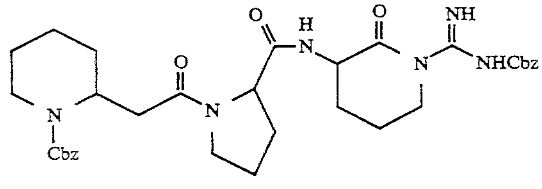

By substantially following the procedures of Example 15, D, 27.36 g (59 mmol) of N-Cbz-2-(2-piperidino)acetyl-L-Pro-benzyl ester was hydrolyzed to afford 31.40 g of the corresponding acid. The presence of the desired acid was confirmed by FDMS (m/e 375; MH+, 100) and a 12.80 g sample of the crude reaction mixture was coupled to N-Cbz-Arg-lactam (12.44 g; 34 mmol) substantially according to the procedures of Example 15, D. Purification of the crude product by flash chromatography ($SiO_2$; 30% $CH_3CN$ in $CH_2Cl_2$) afforded 4.27 g (6.5 mmol) of N-Cbz-2-(2-piperidinino)acetyl-L-Pro-Arg-(Cbz) lactam.

FD-MS, m/e 647 (MH+, 100).

IR ($CHCl_3$) 3012, 1685, 1615, 1499, 1264, 1179 $cm^{-1}$.

Analytical Calculated for $C_{34}H_{42}N_6O_7$: C 63.14, H 6.55, N 12.99 Found: C 63.41, H 6.71, N 12.75

$[\alpha]_D = -45.3°$ (c=0.01, $CH_2Cl_2$).

D) 2-(2-Piperidino) acetyl-L-Pro-L-Arg Aldehyde dihydrochloride monohydrate

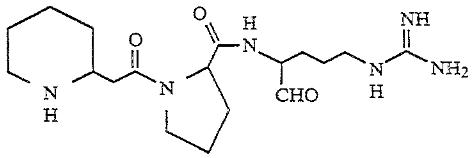

By substantially following the procedures of Example 15, E, 2.60 g (4.2 mmol) of N-Cbz-2-(2-piperdinino)acetyl-L-Pro-Arg-N-Cbz-lactam was reduced with lithium tri-t-butoxyaluminum hydride to afford 2.10 g of the crude protected arginal. Deprotection, again substantially according to the procedures of Example 15, E, afforded 1.13 g (2.49 mmol; 59%) of 2-(2-piperidino)acetyl-L-Pro-L-Arg aldehyde as the dihydrochloride monohydrate.

FAB-MS, m/e 381 (MH+; 100).

IR (KBr) 3336, 2951, 1657, 1453, 1302, 752 $cm^{-1}$.

Analytical Calculated for $C_{18}H_{32}N_6O_3.2HCl.H_2O$: C 47.68, H 7.50, N 18.54 Found: C 47.37, H 7.19, N 18.11

$[\alpha]_D = -143.3°$ (c=0.01, MeOH).

EXAMPLE 19

Preparation of 3-piperidinocarbonyl-L-Pro-L-Arginine Aldehyde Dihydrochloride Monohydrate A) N-Cbz-nipecotic acid

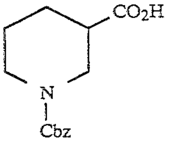

By substantially following the procedures of Example 15, A, 25.0 g (194 mmol) of nipecotic acid was protected with benzylchloroformate under basic conditions to afford 18.0 g (68 mmol; 35%) of analytically pure N-Cbz-nipecotic acid as a white solid.

FD-MS, m/e 264 (MH+, 100).

IR (KBr) 3092, 2950, 1732, 1649, 1449, 1273, 1155, 696 $cm^{-1}$.

Analytical Calculated for $C_{14}H_{17}N_1O_4$: C 63.87, H 6.51, N 5.32 Found: C 63.98, H 6.58, N 5.36

B) N-Cbz-nipecotoyl-L-Pro methyl ester

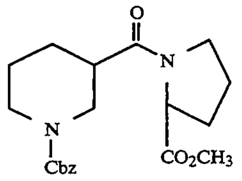

By substantially following the procedures of Example 15, C, 17.0 g (65 mmol) of N-Cbz-nipecotic acid was coupled to proline methyl ester. Purification of the reaction mixture by flash chromatography ($SiO_2$; 70% EtOAc in hexanes) afforded 13.9 g (37.2 mmol; 57%) of N-Cbz-nipecotoyl-L-Pro methyl ester as a clear oil.

FAB-MS, m/e 375 ($MH^+$, 100).

IR (film) 2951, 1746, 1699, 1644, 1426, 1259, 1148, 700 $cm^{-1}$.

Analytical Calculated for $C_{20}H_{26}N_2O_5$: C 64.16, H 7.00, N 7.48 Found: C 64.12, H 7.16, N 7.74

C) N-Cbz-nipecotoyl-L-Pro-Arg-(Cbz) lactam

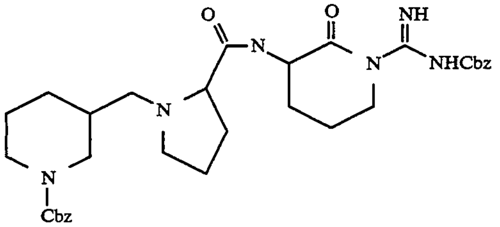

By substantially following the procedures of Example 15, D, 12.9 g (35 mmol) of N-Cbz-nipecotoyl-L-Pro methyl ester was hydrolyzed to afford 10.0 g of the corresponding acid. The presence of the desired product was confirmed by FD-MS (m/e 361; M+1, 100) and the crude reaction mixture was coupled to the Cbz-protected Arg-lactam (10.09 g; 27.8 mmol) again, substantially according to the procedures of Example 1,D. Purification by flash chromatography ($SiO_2$; 50% EtOAc in hexanes) afforded 3.45 g (5.5 mmol; 16% from N-Cbz-nipecotoyl-L-Pro methyl ester) of N-Cbz-nipecotoyl-L-Pro-Arg-N-Cbz lactam.

FD-MS, m/e 633 ($MH^+$, 100).

IR (KBr) 3370, 1700, 1641, 1612, 1264, 1150, 698 $cm^{-1}$.

Analytical Calculated for $C_{33}H_{40}N_6O_7$: C 62.65, H 6.37, N 13.28 Found: C 62.72, H 6.50, N 13.01

$[\alpha]_D = -53.8°$ (c=0.01, MeOH).

D) Nipecotoyl-L-Pro-L-Arg Aldehyde

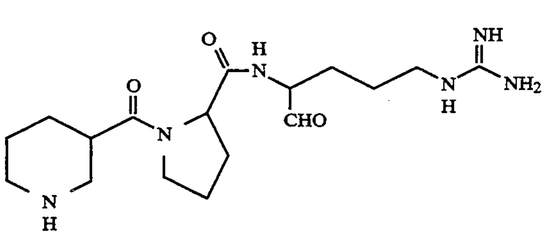

By substantially following the procedures of Example 15, E, 3.0 g (4.7 mmol) of N-Cbz-nipecotoyl-L-Pro-Arg-(Cbz)-lactam was reduced with lithium tri-t-butoxyaluminum hydride to afford 0.75 g of the crude protected arginal. Deprotection by substantially following the procedures of Example 15, E followed by reverse phase chromatography of the crude product yielded 0.13 g (0.2 mmol; 5%) of 3-piperidinocarbonyl-L-Pro-L-Arg aldehyde as the dihydrochloride monohydrate.

FAB-MS, m/e 367 ($M^+$; 100).

IR (KBr) 3336, 2951, 1657, 1453, 1302, 752 $cm^{-1}$.

Analytical Calculated for $C_{18}H_2N_6O_3.2HCl.H_2O$: C 47.68, H 7.50, N 18.54 Found: C 47.37, H 7.19, N 18.11

$[\alpha]_D = -32.2°$ (c=0.01, MeOH).

EXAMPLE 20

Preparation of 3-perhydroindolylcarbonyl-L-pro-L-Arginine Aldehyde Dihydrochloride Monohydrate A) N-Cbz-3-perhydroindolylcarboxylic acid

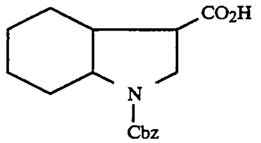

A solution of 25 g (155 mmol) of indole-3-carboxylic acid in 1500 mL $H_2O$ and 150 mL HOAc was charged with 25 g of 5% $Rh/Al_2O_3$ and the mixture hydrogenated at 60 psi for 30 hr at 60° C. The mixture was filtered through Celite ® and evaporated in vacuo to a dark oil which was treated with benzylchloroformate (26.35 g; 155 mmol) under basic conditions substantially according to the procedures of Example 15, A. The crude product crystallized out of hot $CH_2Cl_2$/hexanes to yield 16.06 g (53 mmol; 49%) of N-Cbz-3-perhydroindolylcarboxylic acid as a white solid.

FD-MS, m/e 303 ($M^+$; 100)

IR ($CHCl_3$) 3012, 2942, 1698, 1414, 1305, 1117 $cm^{-1}$.

Analytical Calculated for $C_{17}H_{21}NO_4$: C 67.31, H 6.98, N 4.62 Found: C 67.61 H 6.99, N 4.72

B) N-Cbz-3-perhydroindolylcarbonyl-L-pro-benzyl ester

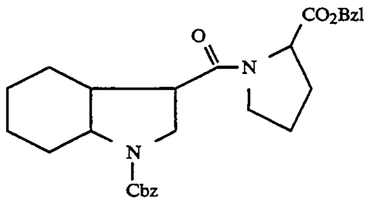

By substantially following the procedures of Example 15, C, 14.03 g (46.3 mmol) of N-Cbz-3-perhydroindolylcarboxylic acid was coupled to proline benzylester to give 22.6 g of crude coupled product. Purification by flash chromatography ($SiO_2$; 10% EtOAc in $CH_2Cl_2$) afforded 18.79 g (38.3 mmol; 83%) of N-Cbz-3-perhydroindolylcarbonyl-L-Pro-benzyl ester as a clear oil.

FD-MS, m/e 490 ($M^+$; 100)

IR ($CHCl_3$) 3013, 2942, 1741, 1694, 1644, 1413, 1174 $cm^{-1}$.

Analytical Calculated for $C_{29}H_{34}N_2O_5$: C 71.00, H 6.98, N 5.71 Found: C 71.10, H 7.12, N 5.77

$[\alpha]_D = -52.9°$ (c=0.01, MeOH).

C) N-Cbz-3-perhydroindolylcarbonyl-L-Pro-Arg-N-Cbz-lactam

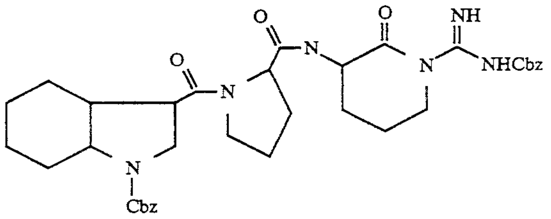

By substantially following the procedures of Example 15, D, 7.54 g (15.39 mmol) of N-Cbz-3-perhydroindolylcarbonyl-L-Pro benzyl ester was hydrolyzed to afford 5.45 g of the corresponding acid. The presence of the desired product was confirmed by FD-MS (m/e 400; M+, 100) and the crude material was coupled to the Cbz-protected Arg-lactam (4.76 g; 13.12 mmol). The product was purified by flash chromatography ($SiO_2$; 75% EtOAc in $CH_2Cl_2$) to afford 4.30 g (6.4 mmol; 42% from N-Cbz-3-perhydroindolylcarbonyl-L-Pro-benzyl ester) of N-Cbz-3-perhydroindolylcarbonyl-L-Pro-Arg-(Cbz) lactam.

FD-MS, m/e 673 ($MH^+$, 100).

IR ($CHCl_3$) 3011, 1687, 1616, 1499, 1268, 1181, 1108 $cm^{-1}$.

Analytical Calculated for $C_{36}H_{44}N_6O_7$: C 64.27, H 6.59, N 12.49 Found: C 64.00, H 6.61, N 12.19

$[\alpha]_D = -59.2°$ (c=0.01, $CH_2Cl_2$).

D) 3-Perhydroindolylcarbonyl-L-Pro-L-Arg Aldehyde

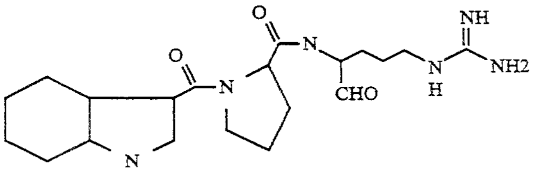

By substantially following the procedures of Example 15, E, 4.08 g (6.16 mmol) of N-Cbz-3-perhydroindolylcarbonyl-L-Pro-Arg-(Cbz)-lactam was reduced with lithium tri-t-butoxyaluminum hydride to afford 2.31 g of the crude protected arginal. Deprotection, again substantially according to Example 15, E, afforded 1.30 g (2.71 mmol; 44% from N-Cbz-3-perhydroindolylcarbonyl-L-pro-Arg-N-Cbz-lactam) of analytically pure 3-perhydroindolylcarbonyl-L-pro-L-Arg Aldehyde as the dihydrochloride monhydrate.

FAB-MS, m/e 407 ($M^+$; 100).

IR (KBr) 3351, 2939, 1658, 1449 $cm^{-1}$.

Analytical Calculated for $C_{20}H_{34}N_6O_3.2HCl.1H_2O$: C 48.30, H 7.69, N 16.89 Found: C 48.72, H 7.41, N 17.01

$[\alpha]_D = -61.8°$ (c=0.01, MeOH).

EXAMPLE 21

Preparation of 2-(N-methyl)aminocyclohexyl-carbonyl-L-Pro-L-Arginine Aldehyde Dihydrochloride

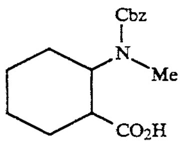

A. 2-(N-methyl-N-Cbz-amino)cyclohexanoic acid

A solution of 50 g (331 mmol) of N-methyl anthranilic acid in $H_2O$ was charged with $RuO_2$ and the mixture hydrogenated at 2000 psi for 10 hrs at 120° C. The catalyst was filtered and the reaction concentrated in vacuo to give 47.2 g of a viscous oil. The oil was taken up in 500 mL of 2N aq NaOH and was washed with $CH_2Cl_2$ (2×250 mL). The basic aqueous layer was treated with benzylchloroformate (56.47 g; 331 mmol) substantially according to the procedures of Example 15, A to afford 50.03 g of crude 2-(N-methyl-N-Cbz-amino)cyclohexanoic acid. The presence of the desired product was confirmed by FDMS (m/e 291, $MH^+$, 100) and the crude product taken on directly to the next step.

B) 2-(N-methyl-N-Cbz-amino)cyclohexylcarbonyl-L-Pro-benzyl ester (21A) and 2-(N-Cbz-amino)cyclohexylcarbonyl-L-Pro-benzyl ester (21B)

21A

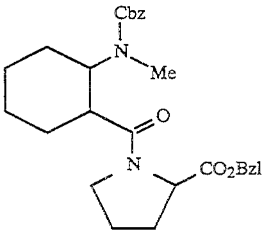

21B

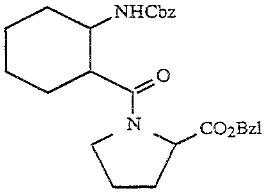

A 24.64 g sample of 2-(N-methyl-N-Cbz-amino)cyclohexanoic acid was coupled to proline benzyl ester (20.49 g; 85 mmol) substantially according to the procedures of Example 15, C. The crude reduction product was purified by flash chromatography ($SiO_2$; 25% EtOAc in hexanes) to afford 22.70 g (47.5 mmol) of 2-(N-methyl-N-Cbz-amino)cyclohexylcarbonyl-L-pro-benzyl ester and 5.37 g (11.6 mmol) of 2-(N-Cbz-amino)cyclohexylcarbonyl-L-pro-benzyl ester.

2-(N-methyl-N-Cbz-amino )cyclohexylcarbonyl-L-Pro-benzyl ester: FD-MS, m/e 478 ($M^+$; 100).

IR ($CHCl_3$) 3013, 2938, 1742, 1683, 1637, 1450, 1347, 1155 $cm^{-1}$.

Analytical Calculated for $C_{28}H_{34}N_2O_5$: C 70.27, H 7.16, N 5.85 Found: C 70.39, H 7.38, N 5.74

$[\alpha]_D = -10.9°$ (c=0.01, MeOH).

2-(N-Cbz-amino)cyclohexylcarbonyl-L-pro-benzyl ester: FD-MS, m/e 464 ($M^+$; 100).

IR ($CHCl_3$) 3011, 2941, 1741, 1691, 1449,1173 $cm^{-1}$.

Analytical Calculated for $C_{27}H_{32}N_2O_5$: C 69.81, H 6.94, N 6.03 Found: C 69.55, H 7.16, N 5.91

$[\alpha]_D = -41.6°$ (c=0.01, MeOH).

C) 2-(N-methyl-N-Cbz-amino)cyclohexylcarbonyl-L-Pro-L-Arg-(Cbz)-lactam

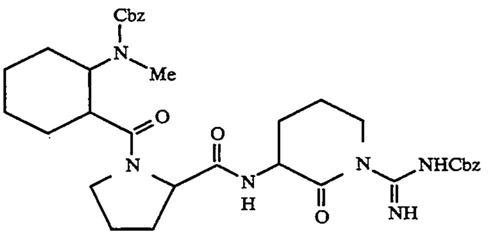

A 22.55 g (47 mmol) sample of 2-(N-methyl-N-Cbz-amino)cyclohexylcarbonyl-L-pro-benzyl ester was hydrolyzed substantially according to the procedures of Example 15, D, to afford 18.90 g of the crude acid. The presence of the desired product was confirmed by FD-MS (m/e 389, Mt1, 100) and the crude material was coupled to Cbz-protected Arg-lactam (17.29 g; 47 mmol), again by substantially the same procedures of Example 15, D. The product was purified by flash chromatography ($SiO_2$; 30% $CH_3CN$ in $CH_2Cl_2$) to afford 12.20 g (33.6 mmol; 72% from 2-(N-methyl-N-Cbz-amino)cyclohexylcarbonyl-L-pro-benzyl ester) of 2-(N-methyl-N-Cbz-amino)cyclohexylcarbonyl-L-pro-L-Arg-(Cbz)-lactam.

FD-MS, m/e 661 (MH+, 100).

IR ($CHCl_3$) 3375, 2941, 1683, 1615, 1498, 1149, 1105 $cm^{-1}$.

Analytical Calculated for $C_{35}H_{44}N_6O_7$: C 63.62, H 6.71, N 12.72 Found: C 63.67, H 6.80, N 12.98

$[\alpha]_D=-31.4°$ (c=0.01, $CH_2Cl_2$).

D) 2-(N-methyl-amino) cyclohexylcarbonyl-L-pro-L-Arg Aldehyde Dihydrochloride

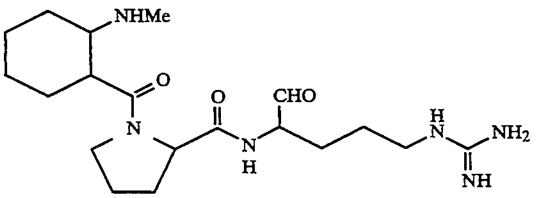

By substantially following the procedures of Example 5, E, 7.90 g (11.97 mmol) of 2-(N-methyl-N-Cbz-amino)cyclohexylcarbonyl-L-pro-L-Arg-(Cbz)-lactam was reduced with lithium tri-t-butoxyaluminum hydride to afford 5.40 g of the crude protected arginal. Deprotection substantially according to the procedures of Example 15, E, afforded 2.84 g (6.08 mmol; 51% from 2-(N-methyl-N-Cbz-amino)cyclohexylcarbonyl-L-Pro-L-Arg-(Cbz)-lactam) of analytically pure 2-(N-methyl-amino)cyclohexylcarbonyl-L-Pro-L-Arg aldehyde as the dihydrochloride salt.

FAB-MS, m/e 395 (MH+; 100).

IR (KBr) 3318, 1659, 1456, 1363 $cm^{-1}$.

Analytical Calculated for $C_{19}H_{34}N_6O_3.2HCl$: C 48.82, H 7.76, N 17.98 Found: C 48.54, H 7.63, N 17.83

$[\alpha]_D=-71.6°$ (c=0.01, MeOH).

EXAMPLE 22

Preparation of 2-aminocyclohexylcarbonyl-L-Pro-L-Arginine Aldehyde Trihydrochloride Monohydrate A) 2-(N-Cbz-amino) cyclohexylcarbonyl-L-Pro-Arg-(Cbz)-lactam

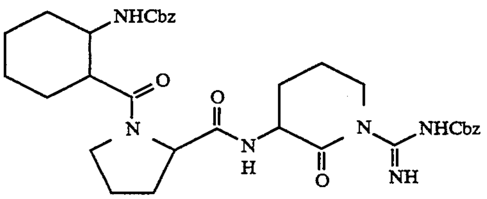

A 5.09 g (10.6 mmol) sample of 2-(N-Cbz-amino)cyclohexylcarbonyl-L-Pro-benzyl ester was hydrolyzed substantially according to the procedures of Example 15, D, to afford 4.34 g of the crude acid. The presence of the desired product was confirmed by FD-MS (m/e 375, MH+, 100) and the crude material was coupled to Cbz-protected Arg-lactam (4.02 g; 11.1 mmol) by substantially the same procedures of Example 15, D. The product was purified by flash chromatography ($SiO_2$; 30% $CH_3CN$ in $CH_2Cl_2$) to afford 1.46 g (2.21 mmol; 20% from 2-(N-Cbz-amino)cyclohexylcarbonyl-L-Pro-benzyl ester) of 2-(N-Cbz-amino)cyclohexylcarbonyl-L-Pro-Arg-(Cbz)-lactam.

FD-MS, m/e 647 (MH+, 100).

IR ($CHCl_3$) 3376, 2943, 1703, 1616, 1509, 1267, 1181, 1043 $cm^{-1}$.

Analytical Calculated for $C_{34}H_{42}N_6O_7$: C 63.14, H 6.55, N 12.99 Found: C 63.23, H 6.47, N 12.79

$[\alpha]_D=-43.7°$ (c=0.01, $CH_2Cl_2$).

B) 2-Aminocyclohexylcarbonyl-L-Pro-L-Arg Aldehyde

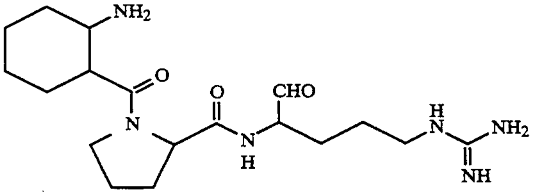

By substantially following the procedures of Example 15, E, 1.28 g (1.94 mmol) of 2-(N-Cbz-amino)cyclohexylcarbonyl-L-Pro-Arg-N-Cbz-lactam was reduced with lithium tri-t-butoxyaluminum hydride to afford 0.82 g of the crude protected arginal. Deprotection, again substantially according to the procedures of Example 15, E, afforded 0.40 g (0.88 mmol; 46% from 2-(N-Cbz-amino)cyclohexylcarbonyl-L-pro-Arg-(Cbz)-lactam) of analytically pure 2-aminocyclohexylcarbonyl-L-pro-L-Arg Aldehyde as the trihydrochloride monohydrate.

FAB-MS, m/e 381 (M+; 100).

IR (KBr) 3330, 1663, 1451, 1002 $cm^{-1}$.

Analytical Calculated for $C_{19}H_{34}N_6O_3.3HCl.H2O$: C 48.82, H 7.76, N 17.98 Found: C 48.54, H 7.63, N 17.83

$[\alpha]_D=-74.5°$ (c=0.01, MeOH).

In Examples 23 through 78, RPHPLC is carried out using 0.1% aqueous (v:v) HCl (designated "A" in the Examples) and acetonitrile (designated "B" in the Examples). Mixtures of A and B are v:v. Where 1H-NMR is shown, the product afforded by the reaction was characterized by proton NMR to confirm the desired compound was obtained.

EXAMPLE 23

1-methylindole-2-carbonyl-D-(α-methyl)phenylglycine-Azt-Arg-H hydrochloride

A) Boc-Arg(Cbz)-OH

To a solution of Boc-Arg(HCL)-OH (82.1 g, 250 mmole) in 5N NaOH (240 ml) chilled to −5° C. was added benzylchloroformate (143 ml, 1.0 mole) (4 eq.) dropwise over 55 minutes while the pH was maintained at 13.2–13.5 using 5N NaOH (250 ml) was added. The aqueous layer was separated and extracted with $Et_2O$ (2×500 ml). The aqueous layer was acidified to pH 3.0 with 3N $H_2SO_4$ (560 ml) and extracted with EtOAc (550 ml). The organic layer separated and aqueous layer extracted with an additional amount of EtOAc. The combined organic layers were washed with water, dried ($MgSO_4$), and concentrated to dryness in vacuo to give the title compound (66.1 g, 65 percent yield):

TLC $R_f$(C) 0.43;

FD-MS 408 ($M^+$);

$^1$HNMR ($CDCl_3$) δ 1.42 (s,9H), 1.61–1.91 (m,4H), 3.23–3.41 (m,2H), 4.17 (d, 1H), 5.21 (s, 2H), 5.62 (d, 1H), 7.30–7.42 (m, 6H), 8.27 (m, 1H).

B) Boc-Arg(Cbz)-lactam

To a solution of Boc-Arg(Cbz)-OH (A) (66.0 g, 0.162 mole) in dry THF (230 ml), cooled to −10° C., was added N-methylmorpholine (18.7 ml, 1.05 eq) followed by isobutylchloroformate (22.5 ml, 1.05 eq). The reaction was stirred 5 minutes at −10° C. and triethylamine (23.5 ml, 1.05 eq) was added. After the reaction was stirred for one hour at −10° C. and one hour at room temperature the reaction was poured into 1 L of ice-water. The resulting precipitate was filtered, washed with cold water, and dried in vacuo. The product was crystallized from EtOAc to give the title compound as a white solid (38.05 g. 60 percent yield):

TLC $R_f$(A) 0.77;

FD-MS 391 ($MH^+$);

$^1$HNMR ($CDCl_3$) δ 1.48 (s,9H), 1.78–1.98 (m,2H), 2.50 (m, 1H), 3.41 (m, 1H), 4.43 (m, 1H), 4.90 (m, 1H), 5.16 (s, 2H), 5.27 (m, 1H), 7.28–7.45 (m, 6H), 9.41 (m, 1H), 9.68 (m, 1H).

C) HCl.Arg(Cbz)-lactam

A solution of HCl(g) saturated in EtOAc (7.2 L) was added dropwise over 30 minutes to a solution of Boc-Arg(Cbz)-lactam (B) (641 g, 1.64 mol) dissolved in $CH_2Cl_2$ (3 L) at −10° C. The reaction was allowed to stir one hour at −10° C. and slowly warmed to room temperature (3 hours). Diethyl ether (12 L) added and the precipitate was filtered, washed with diethyl ether, and dried in vacuo to give the title compound (580 g):

TLC $R_f$(C) 0.29;

FD-MS 291 ($MH^+$).

D) Methyl-$N^α$diphenylmethylene-DL-phenylglycinate

To a solution of benzophenone imine (53.8 g, 297 mmol) in methylene chloride (500 mL) at room temperature was added DL-phenylglycine methylester hydrochloride (59.9 g, 297 mmol) and the reaction stirred for 48 hours. The reaction mixture was washed 3 times with water (200 mL) and the organic layer was separated, dried ($MgSO_4$), filtered, and concentrated in vacuo to give a clear oil. The oil was crystallized from pentane to give the title compound (98.5 g, 100 percent yield)

FAB-MS 330 (MHt); Analysis Calculated for $C_{22}H_{19}NO_2$: C 80.22 H 5.81 N 4.25 Found: C 80.50 H 5.93 N 4.14

E) Methyl-$N^α$diphenylmethylene-DL-(α-methyl)phenylglycinate

A solution of methyl-$N^α$diphenylmethylene-DL-phenylglycinate (D) (14.8 g, 44.8 mmol) in anhydrous THF (200 mL) was added dropwise to a mixture of 18-crown-6 (11.8 g, 44.8 mmol), potassium hydride (11.2 g, 67.3 mmol), THF (100 mL) under an inert atmosphere. To the reaction was added a solution of methyl iodide (6.0 mL, 89.7 mmol) in THF (20 mL) dropwise. The reation was stirred for an additional 1.5 hours at room temperature. To the reaction was added a solution containing D, HOAc (7.0 mL), water (25 mL), and THF (30 mL) dropwise. The reaction was diluted with ethyl acetate and water, the organic layer was separated, washed three times with water, dried ($MgSO_4$), and filtered. The filtrate was concentrated in vacuo to give an oil which crystallized from hexane to give the title compound (10.2 g, 66 percent yield)

FAB-MS 344 ($MH^+$)

Analysis Calculated for $C_{23}H_{21}NO_2$: C 80.44 H 6.15 N 4.08 Found: C 80.40 H 6.26 N 4.03

F) DL-(α-methyl)phenylglycine

A solution of methyl-$N^α$diphenylmethylene-DL-(α-methyl)phenylglycinate (E) (72.4 g, 211 mmol) in 5N HCl (400 mL) was refluxed (24 hours). The solution was cooled to room temperature, filtered, and the filtrate pH adjusted to 5.8 with dilute $NH_4OH$ solution. The aqueous solution concentrated in vacuo until crystallization began. The reaction stored overnight at 5° C. and the precipatate filtered, and dried in vacuo to give the title compound (22 g, 63 percent yield)

FAB-MS 166 ($MH^+$).

G) D-(α-methyl)phenylglycine

A solution of DL-(α-methyl)phenylglycine (F) (87 g, 431.4 mmol) in water was adjusted to pH 6.0 with 5N NaOH. The precipitate was filtered and dried to yield 82 g of white solid. The solid (82 g) was suspended in 96 percent formic acid (750 mL) and acetic anhydride (200 mL, 431.4 mmol) was added slowly to the reaction mixture. The reaction was allowed to stir at room temperature for 30 minutes and the solution concentrated in vacuo to an oil. The oil was dissolved in EtOAc (1500 mL), washed three times with water, dried ($MgSO_4$), and filtered. The filtrate was concentrated in vacuo and crystallized from EtOAc/hexane to give a white solid of $N^α$-formyl-DL-(α-methyl)phenylglycine (77.9 g, 93 percent). The $N^α$-formyl-DL-(α-methyl)phenylglycine (77.3 g, 400 mmol) was dissolved in EtOAc (450 mL) and EtOH (50 mL). To this solution was added quinine (68.18 g, 210 mmol) and diethylether (1000 mL). The solution was allowed to stand at room temperature (24 hours). The resulting crystalline material was filtered and the mother liquors were concentrated in vacuo to a white solid. The white solid was suspended in EtOAc, washed with 1.5N citric acid, water, dried ($MgSO_4$), and filtered. The filtrate was concentrated in vacuo to a white solid of $N^α$-formyl-D-(α-methyl)phenylglycine (26.3 g, 67 percent yield);

$[α]_D=-61°$ (C=0.5/MeOH). The $N^α$-formyl-D-(α-methyl)phenylglycine (25 g, 124 mmol) was suspended in 2N HCl (130 mL) and the reaction was refluxed (2 hours). The reaction mixture was cooled to room temperature and the aqueous solution concentrated in vacuo until crystallization began. The precipitate was collected and dried in vacuo to give pure title compound (18.6 g, 74 percent yield).

H) 1-methylindole-2-carbonyl-D-(α-methyl)phenylglycine

To a solution of D-(α-methyl)phenylglycine (G) (2.01 g, 10 mmol) in water was added 2N NaOH to adjust the pH to 6.5 and the solution was freeze dried. The solid was suspended in DMF (30 mL), bis(trimethylsilyl)acetamide (3.7 mL, 15 mmol), and 1-methylindole-2-carboxylpentafluorophenyl ester (3.41 g, 10 mmol) was added to the reaction. The reaction mixture was stirred at 60° C. (24 hours) and concentrated in vacuo to an oil. The residue was dissolved in water (100 mL), diethyl ether (50 mL), and the pH adjusted to 9.0 with 2N NaOH. The aqueous layer was separated, EtOAc (150 mL) was added, and the solution was acidified with 5N HCl to pH 2.8. The organic layer separated, dried ($MgSO_4$), filtered, and concentrated in vacuo to an amorphous solid of the title compound (2.27 g, 70 percent yield)

FAB-MS 323 (MH+).

I) 1-methylindole-2-carbonyl-D-(α-methyl)phenylglycine-Azt-OH

To a solution of 1-methylindole-2-carbonyl-D-(α-methyl)phenylglycine (H) (2.2 g, 6.9 mmol) in EtOAc (25 mL) was added 2,4,5 trichlorophenol (1.65 g, 8.3 mmol), DCC (1.72 g, 8.3 mmol), and cooled to 0° C. The reaction was stirred for one hour at 0° C. and 1.5 hours at room temperature. The resultant precipitate was removed by filtration, and the mother liquor was concentrated in vacuo to an oil. The resultant oil was dissolved in pyridine (35 mL), and L-azetidine-2-carboxylic acid (0.7 g, 6.9 mmol), and triethylamine (0.97 mL, 6.9 mmol) were added to the reaction mixture. After the reaction was stirred at room temperature (24 hours) the pyridine was removed in vacuo to an oil. The residue was dissolved in water (100 mL), diethyl ether (50 mL) and the pH of the solution was adjusted to 9.0 with 2N NaOH. The aqueous layer separated, EtOAc (150 mL) was added, and the pH of the solution adjusted to 3.0 with 3N HCl. The organic layer separated, dried ($MgSO_4$), filtered, and the filtrate evaporated in vacuo to an amorphous solid of crude title compound (2.3 g). The crude solid (2.3 g) was purified by chromatography on silica gel using a step gradient elution ($CHCl_3$ 100 to $CHCl_3$-MeOH 70:30) to yield pure title compound as an amorphous solid (0.81 g, 29 percent yield);

FD-MS 406 (MH+).

J) 1-methylindole-2-carbonyl-D-(α-methyl)phenylglycine-Azt-Arg(Cbz)-lactam

In flask 1 1-methylindole-2-carbonyl-D-(α-methyl)-phenylglycine-Azt-OH (I) (0.51 g, 1.5 mmol) was dissolved in DMF (10 mL), cooled to −15° C., and N-methylmorpholine (0.17 mL, 1.55 mmol) was added followed by isobutylchloroformate (0.19 mL, 1.41 mmol). The reaction mixture was stirred at −15° C. for 2 minutes. In flask 2 HCl.Arg(Z)-lactam (C) (0.46 g, 1.41 mmol) was dissolved in DMF (10 mL), cooled to 0° C., and diisopropylethylamine (0.27 mL, 1.55 mmol) was added. The reaction mixture was stirred at 0° C. for 2 minutes.

The contents of flask 2 were added to flask 1, and the reaction mixture was stirred for 4 hours (−15° C.) followed by 24 hours at room temperature. A solution of 1N $NaHCO_3$ (2 mL) was added, and the reaction mixture concentrated in vacuo. The residue was dissolved with EtOAc (100 mL) and water (50 mL). The organic layer was separated and washed sequentially with 1N $NaHCO_3$, water, and 0.1N HCl. The organic layer was dried ($MgSO_4$), filtered, and evaporated in vacuo to an amorphous solid of title compound (0.88 g, 92 percent yield).

TLC $R_f$(A) 0.74;

FAB-MS 678 (MH+).

K) 1-methylindole-2-carbonyl-D-(α-methyl)phenylglycine-Azt-Arg-H .HCl

To a stirred, cooled (−70° C.) solution of 1-methylindole-2-carbonyl-D-(α-methyl) phenylglycine-Azt-Arg(Cbz)-lactam (J) (0.81 g, 1.19 mmol) under a nitrogen atmosphere in anhydrous THF (50 mL) was added lithium aluminum hydride 1M in THF (1.2 mL, 1.2 mmol). The reaction stirred for 30 minutes at −70° C. A solution of 5 mL of THF and 5 mL of 0.5N $H_2SO_4$ was added dropwise to the reaction. The reaction was diluted with EtOAc (100 mL) and water (50 mL). The organic layer was separated, dried ($MgSO_4$), filtered, and concentrated to dryness in vacuo to give an amorphous solid (0.76 g). The solid was dissolved in ethanol (100 mL), water (25 mL), and 1N HCl (1.67 mL, 1.67 mmol), and was hydrogenated in the presence of 5 percent Pd/C catalyst (0.5 g) at ambient temperature and pressure. After the reaction was completed, the catalyst was removed by filtration. The filtrate was concentrated to 100 mL in vacuo and freeze dried. The white solid was dissolved in water, filtered through a Millipore 0.5 μm filter, and freeze dried to give pure title comopund (0.445 g, 64 percent yield):

FAB-MS 546 (MH+);

$[\alpha]_D = -42.9°$ (C=0.5/0.01N HCl).

EXAMPLE 24

Preparation of D-Prolinyl (αbenzyl)-L-Prolinyl-L-arginine aldehyde, dihydrochloride dihydrate

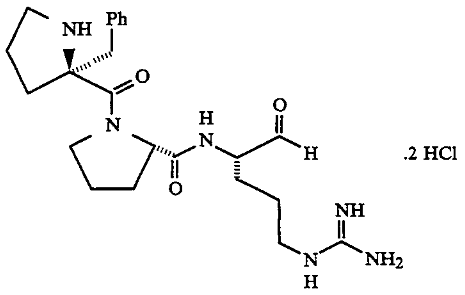

A) N-Cbz-Pro-OMe

To a solution of N-Cbz-proline (140 g, 562 mmol) in methanol (850 mL) was added p-toluenesulfonic acid monohydrate (5 g, 26 mmol). The solution was heated to reflux and stirring continued for 12 h. The heating mantle was removed, and after cooling to room temperature, the solvent was removed by rotary evaporation. The residue was dissolved in ethyl acetate (500 mL), and washed twice with saturated aqueous $NaHCO_3$ (300 mL), twice with brine (200 mL), dried with $MgSO_4$ filtered and concentrated to give a colorless oil (129 g, 88% yield)

FD-MS, m/e 263 (M+)

Analysis Calculated for $C_{14}H_{17}NO_4$; C 63.87, H 6.51, N 5.32; Found: C 64.03, H 6.56, N 5.28.

B) N-Cbz-D,L-Pro-(αbenzyl)-OMe

To a 0.5 M solution of potassium hexamethyldisilazide (200 mL, 100 mmol) in toluene at −78° C. and under $N_2$, was added a solution of N-Cbz-Pro-OMe in tetrahydrofuran (150 mL) via an addition funnel over 1 h. To this mixture was then added a solution of benzyl bromide (11.9 mL, 100 mmol) in tetrahydrofuran (50 mL), via another addtion funnel over 15 min. The cold bath was removed after stirring for 20 h, 1N citric acid (100 mL) was added. The solution was then concentrated to a volume of about 100 mL in vacuo and then partitioned between ethyl acetate (300 mL) and water (200 mL). The organic phase was then washed with 1N citric acid (200 mL), twice with saturated aqueous $NaHCO_3$, twice with brine, dried with $MgSO_4$, filtered and concentrated in vacuo to give an amber oil. The oil was then chromatographed over silica gel, eluting with a gradient from hexanes through 20% ethyl acetate/hexanes. The product containing fractions as judged by TLC were combined and concentrated to give a colorless oil (26.9 g, 76% yield).

$^1$H-NMR C) N-Cbz-D,L-Pro-(αbenzyl)-OH

To a solution of N-Cbz-D,L-Pro-(αbenzyl)-OMe (26.9 g, 76 mmol) in p-dioxane (200 mL) was added a solution of $LiOH.H_2O$ (12.8 g, 304 mmol) in water (100 mL ). The solution was heated to reflux and stirring continued for 12 h. The heating mantle was then removed and after cooling to room temperature, the solvents were removed by rotary evaporation. The residue was dissolved in water (300 mL) and washed with diethyl ether (200 mL). The aqueous phase was then acidified with 1N citric acid and then extracted three times with diethyl ether (300 mL). The combined ether extracts were dried with $MgSO_4$, filtered and concentrated to give a white solid (23.9 g, 92% yield).

$^1$H-NMR FD-MS, m/e 340 ($MH^+$)

Analysis Calculated for $C_{20}H_{21}NO_4$; C 70.78, H 6.24, N 4.13; Found: C 71.00, H 6.38, N 4.17.

D) N-Cbz-D-Pro-(αbenzyl)-Pro-OMe

To a solution of N-Cbz-D-Pro-(αbenzyl)-OH (23 g, 68 mmol), Pro-OMe.HCl (14 g, 85 mmol), 1-hydroxybenzotriazole (11.4 g, 85 mmol), and N,N-diisopropylethylamine (35.4 mL, 203 mmol) in dichloromethane (400 mL) was added 1-(3-dimethylaminopropyl)-3-ethylcarbodiimide hydrochloride (16.2 g, 85 mmol). After stirring for 12 h, the solvent was removed in vacuo. The residue was dissolved in ethyl acetate (500 mL) and washed twice with 1N citric acid (200 mL), twice with saturated aqueous $NaHCO_3$, and twice with brine. The ethyl acetate was removed by rotary evaporation to give a yellow oil. The oil was chromatographed, eluting with a solvent gradient from hexanes through 30% ethyl acetate/hexanes. The fractions containing the higher $R_f$ diastereomer only (TLC, $R_f$ 0.38, 10:1 chloroform:methanol) were combined and concentrated to give a white crystaline solid (10.5 g, 34%). Subsequently, the structure and stereochemistry of this diastereomer was proven to be N-Cbz-D-Pro-(αbenzyl)-pro-OMe by single crystal X-ray diffraction analysis.

$^1$H-NMR, FD-MS, m/e 450 ($M^+$)

Analysis Calculated for $C_{26}H_{30}N_2O_5$; C 69.31, H 6.71, N 6.22; Found: C 69.18, H 6.73, N 6.25.

E) N-Cbz-D-Pro-(αbenzyl)-Pro-OH

To a solution of N-Cbz-D-Pro-(αbenzyl)-Pro-OMe 8 g, 17.8 mmol) in p-dioxane (200 mL) was added a solution of $LiOH.H_2O$ (3 g, 71 mmol) in water (100 mL) with vigorous stirring. After 12 h, the solution was concentrated to a volume of 50 mL in vacuo, diluted with water (100 mL), and extracted twice with diethyl ether (150 mL). The aqueous phase was adjusted to pH 2 with 5N aqueous HCl and the resulting precipitate was filtered, washed with water and dried to give a white solid (4.2 g, 54% yield). The combined aqueous phase was extracted twice with ethyl acetate (250 mL) and the resulting organic phase was washed with brine (200 mL), dried with $Na_2SO_4$, filtered, and concentrated to give another 3.2 g (41% yield) of the same product (95% yield combined).

$^1$H-NMR, FD-MS, m/e 437 ($MH^+$)

Analysis Calculated for $C_{25}H_{28}N_2O_5$; C 68.79, H 6.47, N 6.42; Found: C 68.51, H 6.51, N 6.45.

F) D-Pro-(αbenzyl)-Pro-Arg-H.2 HCl

By methods substantially equivalent to those described in Example 23-J and 23-K, using $LiAl(O\text{-}t\text{-}Bu)_3H$ at −23° C. in place of LAH at −78° C., 1.3 g of D-Pro-(αbenzyl)-Pro-Arg-H.2 HCl dihydrate was prepared from N-Cbz-D-Pro-(αbenzyl)-Pro-OH.

$^1$H-NMR, FAB-MS, m/e 443 ($MH^+$)

Analysis Calculated for $C_{23}H_{34}N_6O_3.2.5HCl.2H_2O$; C 48.49, H 7.16, N 14.75; Found; C 48.84, H 7.05, N 14.48.

EXAMPLE 25

Preparation of Prolinyl (αbenzyl)-L-Prolinyl-L-Arginine Aldehyde Dihydrochloride

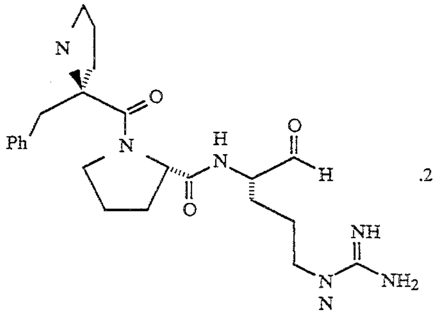

.2 HCl

A) N-Cbz-Pro(αbenzyl)-Pro-OMe

N-Cbz-Pro(αbenzyl)-Pro-OMe was prepared in Example 24-D. After silica gel chromatography of the yellow oil, the fractions containing lower $R_f$ material (TLC, $R_f$ 0.31, 10:1 chloroform:methanol) were combined and concentrated to give a white foam (9.6 g, 31% yield), which was assigned by inference to be N-Cbz-Pro-(αbenzyl)-Pro-OMe.

$^1$H-NMR, FD-MS, m/e 450 ($M^+$)

Analysis Calculated for $C_{26}H_{30}N_2O_5$; C 69.31, H 6.71, N 6.22; Found: C 69.25, H 6.93, N 6.16.

B) Pro(αbenzyl)-Pro-Arg-H.2 HCl

By methods substantially equivalent to those described in Example 24-E and 24-F, 2.0 g of Pro(αbenzyl)-Pro-Arg-H.2 HCl dihydrate was prepared from N-Cbz-Pro-(αbenzyl)-Pro-OMe.

$^1$H-NMR, FAB-MS, m/e 443 ($MH^+$)

Analysis Calculated for $C_{23}H_{34}N_6O_3.3HCl.2.5H_2O$; C 46.28, H 7.09, N 14.08; Found: C 46.67, H 7.13, N 13.75.

EXAMPLE 26

Preparation of Azetidinyl(αbenzyl)-L-Prolinyl-L-Arginine Aldehyde Dihydrochloride

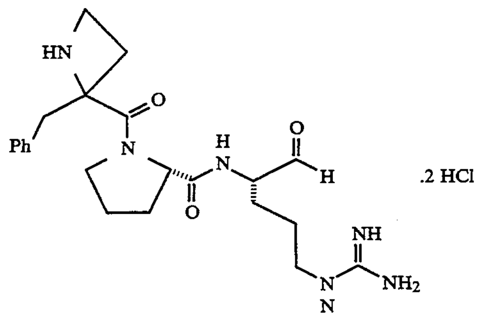

Azt-(αbenzyl)-Pro-Arg-H.2 HCl

By methods substantially equivalent to those described in Example 23-A and 24, 1.5 g of Azt(αbenzyl)-Pro-Arg-H.2 HCl was prepared from azetidine-2-carboxylic acid.

$^1$H-NMR, FAB-MS, m/e 429 (MH+)

Analysis Calculated for $C_{22}H_{32}N_6O_3.2.5HCl.2H_2O$; C 47.55, H 6.98, N 15.12; Found; C 47.21, H 6.62, N 14.83.

EXAMPLE 27

Preparation of N-ethoxycarbonyl-D-Phenylalanyl(α-methyl)-L-prolinyl-L-arginine aldehyde hydrochloride

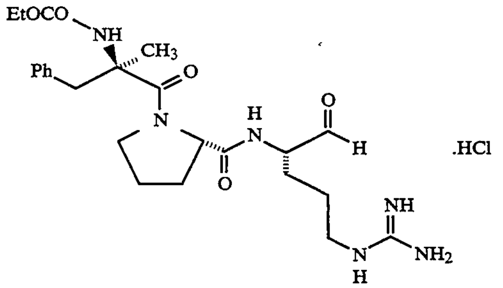

A) EtOCO-D,L-Phe(αMe)-OH

To a stirring suspension of D,L-Phe(αMe)-OH (7.5 g, 42 mmol) in tetrahydrofuran (250 mL) was added N,O-bis(trimethylsilyl)acetamide (12.8 g, 62.8 mmol). Upon clarification the solution was cooled to 0° C. and N,N-diisopropylethylamine (5.4 g, 42 mmol) was added, followed by ethyl chloroformate (4.5 g, 42 mmol). After 2 h, water (100 mL) was added and then the organic solvent was removed in vacuo. The aqueous phase was diluted with 1N NaOH and washed twice with diethyl ether. The aqueous phase was then acidified to pH 2 with concentrated HCl and extracted three times with ethyl acetate. The combined ethyl acetate extracts were dried ($Na_2SO_4$), filtered and concentrated in vacuo to give 10.3 g (98% yield) of a white solid.

$^1$H NMR

B) EtOCO-D,L-Phe(αMe)-Pro-OBzl

To a stirring solution of EtOCO-D,L-Phe(αMe)-OH (10.3 g, 41 mmol), HOBT (5.5 g, 41 mmol), Pro-OBzl.HCl (9.9 g, 41 mmol) and N,N-diisopropylethylamine (15.9 g, 123 mmol) in dimethylformamide (200 mL) at 0° C., was added 1-(3-dimethylaminopropyl)-3-ethylcarbodiimide.HCl (8.6 g, 45 mmol). After stirring for 16 h, the solvents were removed in vacuo and the residue was dissolved in ethyl acetate (500 mL). The organic phase was washed three times with 0.1N HCl, three times with saturated aqueous $NaHCO_3$, and once with brine. The organic phase was then dried ($Na_2SO_4$), filtered and concentrated in vacuo. The residue was chromatographed over silica gel eluting with 1:1 ethyl acetate:hexanes and the product containing fractions (as judged by TLC) were combined and concentrated in vacuo to give 13.5 g (75% yield) of a white foam.

$^1$H NMR FD-MS, m/e 438 (M+)

Analysis Calculated for $C_{25}H_{30}N_2O_5$; C 68.47 H 6.90 N 6.39 Found: C 68.20 H 7.09 N 6.28

C) EtOCO-D,L-Phe(αMe)-Pro-OH

To a stirring solution of EtOCO-D,L-Phe(αMe)-Pro-OBzl (13.2 g, 30 mmol) in p-dioxane (250 mL) was added a solution of $LiOH.H_2O$ (6.3 g, 151 mmol) in water (125 mL). After stirring for 2.5 h, the solvent was removed in vacuo and the residue was diluted with water and washed three times with diethyl ether. The aqueous phase was then taken to pH 2 with conc. HCl and extracted three times with ethyl acetate. The combined ethyl acetate extracts were dried ($Na_2SO_4$), filtered and concentrated in vacuo to give 10.7 g of a white solid.

$^1$H NMR FD-MS, m/e 349 (MH+)

Analysis Calculated for $C_{18}H_{24}N_2O_5$; C 62.05 H 6.94 N 8.04 Found: C 62.29 H 6.98 N 8.12

D) Boc-Arg(Cbz)-OH

Boc-Arg(HCl)-OH (82.1 g, 250 mmol) was dissolved in 5N NaOH (240 mL) in a 3 necked flask. The reaction mixture was chilled to −5° C. and the pH was maintained at 13.2–13.5 using 5N NaOH (250 mL) while adding benzyl chloroformate (143 mL, 1.0 mol) dropwise (55 min). The reaction mixture was stirred for an additional 1 hour at −5° C. and diluted with water (100 mL) and diethyl ether (500 mL). The aqueous layer was separated and extracted twice with diethyl ether (500 mL). The aqueous layer was then acidified to pH 3.0 with 3N $H_2SO_4$ (560 mL) and extracted with ethyl acetate (550 mL). The aqueous layer was separated and extracted once with ethyl acetate. The combined ethyl acetae layers were washed with water, dried ($MgSO_4$) and concentrated in vacuo to give 66.1 g (65% yield) of a white solid:

$^1$H NMR FD-MS 408 (M+)

E) Boc-Arg(Cbz)-lactam

Boc-Arg(Cbz)-OH (66.0 g, 0.162 mol) was dissolved in tetrahydrofuran (230 mL) and cooled to −10° C. To this solution was added N-methylmorpholine (18.7 mL, 0.17 mol) followed by isobutyl chloroformate (22.5 mL, 0.17 mol). After stirring 5 minutes at −10° C., triethylamine (23.5 mL, 0.17 mol) was added. After an additional 1 hour at −10° C., the mixture was allowed to warm to room temperature and stirring continued for 1 h at room temperature. The reaction mixture was then poured into 1 L of ice-water and the resulting precipitate was filtered, washed with cold water, and dried in vacuo. The product was crystallized from ethyl acetate to give 38 g (60% yield) of a white solid.

$^1$H NMR FD-MS 391 (MH+)

F) 2HCl.Arg(Cbz)-lactam

A solution of HCl(g) saturated in ethyl acetate (7.2 L) was added dropwise over 30 minutes to a solution of Boc-Arg(Cbz)-lactam (641 g, 1.64 mol) dissolved in dichloromethane (3 L) at −10° C. After 1 h at −10° C.

the cold bath was removed and the solution was allowed to warm to room temperature over 3 h. Diethyl ether (12 L) was added and the resulting precipitate was filtered, washed with diethyl ether, and dried in vacuo to give 580 g (97% yield)

FD-MS 291 (MH+)

G) EtOCO-D-Phe(αMe)-Pro-Arg(Cbz)lactam

In flask 1, EtOCO-D,L-Phe(αMe)-Pro-OH (6 g, 17.2 mmol) was dissolved in dimethylformamide (100 mL), cooled to −15° C. and N-methylmorpholine (1.7 g, 17.2 mmol) was added, followed by isobutyl chloroformate (2.4 g, 17.2 mmol). The reaction mixture was allowed to stir at −15° C. for 10 min.

In flask 2, HCl.Arg(Cbz)lactam (6.3 g, 17.2 mmol) was dissolved in dimethylformamide (100 mL), cooled to 0° C., and N,N-diisopropylethylamine (4.5 g, 34.5 mmol) was added.

The contents of flask 2 were added to flask 1 in one portion and the reaction mixture was allowed to slowly warm to room temperature (24 h). Then saturated aqueous $NaHCO_3$ (100 mL) was added and the solvent was removed in vacuo. The residue was partitioned between ethyl acetate and water and the layers were separated. The organic layer was washed twice with 0.01N HCl, twice with saturated $NaHCO_3$, and once with brine. The organic layer was dried ($Na_2SO_4$), and the filtrate was concentrated in vacuo. The residue was chromatographed over silica gel, eluting with ethyl acetate, which provided separation of the diastereomeric products. The fractions containing pure EtOCO-D-Phe(αMe)-Pro-Arg(Cbz)lactam (TLC $R_f$=0.57, 4:1 ethyl acetate:acetonitrile) were combined and concentrated in vacuo to give 1.3 g of white foam. The fractions containing pure EtOCO-Phe(αMe)-Pro-Arg(Cbz)lactam (TLC $R_f$=0.44, 4:1 ethyl acetate:acetonitrile) were combined and concentrated in vacuo to give 1.7 g of white foam. Fractions containing a mixture of the two diastereomers were combined and concentrated in vacuo to give 3.3 g of white foam. The mixture was chromatographed again and the pure fractions of each diastereomer were combined with those from the initial chromatography and concentrated in vacuo to give a total of 2.1 g (20%) of EtOCO-D-Phe(αMe)-Pro-Arg(Cbz)lactam and 3.7 g (35%) of EtOCO-Phe(αMe)-Pro-Arg(Cbz)lactam. The structure of the diastereomeric tripeptides was tentatively assigned by inference from the biological activity of the corresponding arginine aldehydes.

$^1H$ NMR FD-MS, m/e 621 (M+)

Analysis Calculated for $C_{32}H_{40}N_6O_7$; C 61.92 H 6.50 N 13.54 Found C 61.74 H 6.51 N 13.33

H) EtOCO-D-Phe(αMe)-Pro-Arg-H.HCl

To a stirring solution of EtOCO-D-Phe(αMe)-Pro-Arg(Cbz)lactam (2 g, 3.2 mmol) in tetrahydrofuran (50 mL) at −23° C., was slowly added a solution of 1N $LiAl(O\text{-}t\text{-}Bu)_3H$ (4.8 mL, 4.8 mmol) in tetrahydrofuran. After 2.5 h, the reaction mixture was poured into a stirring solution of cold 1N HCl (50 mL). The solution was then diluted with water (100 mL), washed with 1:1 tetrahydrofuran: hexanes (200 mL) and extracted twice with ethyl acetate and once with n-butanol. The combined ethyl acetate and n-butanol extracts were dried ($Na_2SO_4$), and concentrated in vacuo.

The residue was then dissolved in ethanol (75 mL) and then water (25 mL) and 1N HCl (10 mL) were added. To this stirring solution was then added 5% Pd on carbon (1 g). $H_2$ was then bubbled through the solution for 1.5 h, and then the reaction was flushed with $N_2$ and filtered over a pad of Celite ®. The ethanol was removed in vacuo at 35° C. and then the resiude was redissolved in water (25 mL). The pH of the aqueous solution was adjusted to 4.7 with Bio Rad ion exchange resin (basic form), filtered and lyophilized to give 1.15 g of a white powder. The product was then purified by RPHPLC (98/2 (A:B), 40 min; ramp up to 80/20 (A:B), 280 min; hold to 400 min) to give 0.49 g (29%) of pure EtOCO-D-Phe(αMe)-Pro-Arg-H.HCl dihydrate.

$^1H$ NMR FAB-MS, m/e 489 (MH+)

Analysis Calculated for $C_{24}H_{36}N_6O_5$.HCl; C 54.91 H 7.10 N 16.01 Cl 6.75 Found C 54.89 H 7.12 N 15.81 Cl 6.87

EXAMPLE 28

Preparation of N-ethylsulfonyl-D-Phenylalanyl(α-methyl)-L-prolinyl-L-arginine aldehyde hydrochloride

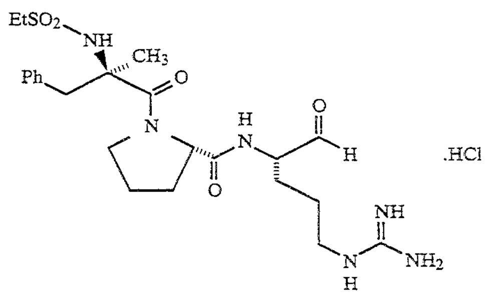

A) $EtSO_2$-D,L-Phe (αMe)-OH

To a stirring suspension of D,L-Phe(αMe)-OH (9 g, 50 mmol) in tetrahydrofuran (250 mL) was added N,O-bis(trimethylsilyl)acetamide (15.3 g, 75 mmol). Upon clarification the solution was cooled to −78° C. and N,N-diisopropylethylamine (6.5 g, 50 mmol ) was added, followed by ethanesulfonyl chloride (7.1 g, 55 mmol). The mixture was allowed to warm slowly to room temperature. After 16 h, water (100 mL) was added and then the organic solvent was removed in vacuo. The aqueous phase was diluted with 1N NaOH and washed twice with diethyl ether. The aqueous phase was then acidified to pH 3 with concentrated HCl and extracted three times with ethyl acetate. The combined ethyl acetate extracts were dried ($Na_2SO_4$), filtered and concentrated in vacuo to give 4.9 g (36% of a white foam.

$^1H$ NMR FD-MS, m/e 271 (M+)

Analysis Calculated for $C_{12}H_{17}NO_4S$; C 53.12 H 6.32 N 5.16 Found: C 53.36 H 6.16 N 5.08

B) $EtSO_2$-D-Phe(αMe)-Pro-Arg-H.HCl

By methods substantially equivalent to those described in Example 27-B, 27-C, 27-G, and 27-H, was prepared 1.1 g of $EtSO_2$-D-Phe(αMe)-Pro-Arg-H.HCl. The diastereomeric peptides were separated at the lactam stage (see Example 27-G) by silica gel chromatography ($EtSO_2$-D-Phe(αMe)-Pro-Arg(Cbz)lactam; TLC $R_f$=0.75, 4:1 ethyl acetate:acetonitrile). $EtSO_2$-D-Phe(αMe)-Pro-Arg-H.HCl was purified by RPHPLC (98/2 (A/B), 40 min; up to 80/20 (A/B), 280 min; hold to 400 min)

$^1H$ NMR FAB-MS, m/e 509 (MH+)

Analysis Calculated for $C_{23}H_{36}N_6O_5S$.HCl; C 50.68 H 6.84 N 15.42 Found: C 50.59 H 6.67 N 15.35

EXAMPLE 29

Preparation of N-ethoxycarbonyl-phenylalanyl(αmethyl)-L-prolinyl-L-arginine aldehyde hydrochloride

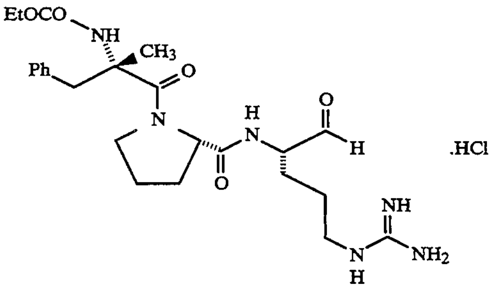

EtOCO-Phe(αMe)-Pro-Arg-H.HCl

By methods substantially equivalent to those described in Example 27-H, 0.78 g (42%) of EtOCO-Phe(αMe)-Pro-Arg-H.HCl was prepared from EtOCO-Phe(αMe)-Pro-Arg(Cbz)lactam (for preparation of EtOCO-Phe(αMe)-Pro-Arg(Cbz)lactam, see Example 27-G). EtOCO-Phe(αMe)-Pro-Arg-H.HCl hydrate was purified by RPHPLC (95/5 (A/B), 40 min; to 80/20 (A/B), 280 min; hold to 400 min)

$^1H$ NMR FAB-MS, m/e 489 (MH+)

Analysis Calc. for $C_{24}H_{36}N_6O_5.1.1HCl.0.5H_2O$; C 53.61 H 7.14 N 15.63 Cl 7.25 Found: C 54.01 H 6.70 N 15.12 Cl 7.18

EXAMPLE 30

Preparation of N-(1-methylindolyl-2-carbonyl)-D-phenylalanyl(α-methyl)-L-prolinyl-L-arginine aldehyde dihydrochloride

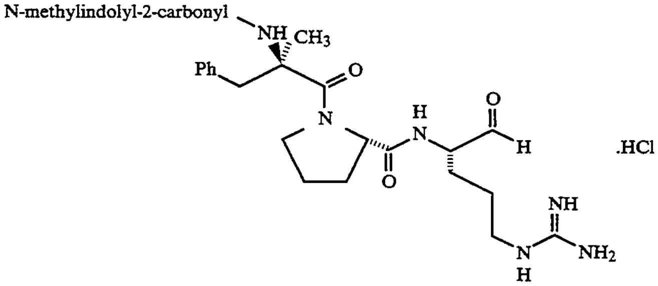

A) NMI-OPFF

To a solution of N-methyl indole-2-carboxylic acid (25 g, 143 mmol) and pentafluorophenol (35.3 g, 192 mmol) in tetrahydrofuran (250 mL) was added 1-(3-dimethylaminopropyl)-3-ethylcarbodiimide.HCl (30.5 g, 159 mmol). After stirring for 5 h, the solution was diluted with dichloromethane (200 mL) and hexanes (300 mL). The organic phase was washed with once with 1 N $NaHSO_4$ (100 mL), three times with 1N $K_2CO_3$ (100 mL) and twice with brine. The organic phase was dried ($Na_2SO_4$), filtered and concentrated in vacuo to give a tan solid which was recrystalized from hexanes to give 38 g (78% yield) of an off white solid.

$^1H$ NMR FD-MS, m/e 341 (M+)

Analysis Calculated for $C_{16}H_8NO_2F_5$; C 56.32 H 2.36 N 4.10 Found: C 56.53 H 2.37 N 4.20

B) NMI-D,L-Phe(αMe)-OH

To a stirring suspension of D,L-Phe(αMe)-OH (2.5 g, mmol) in dimethylformamide (50 mL) was added N,O-bis(trimethylsilyl)acetamide (4.3 g, 21 mmol). Upon clarification of the solution, NMI-OPFF (5 g, 14.7 mmol) was added and the reaction was heated to 65° C. After 16 h, the heating mantle was removed and water (20 mL) was added. The solvents were then removed in vacuo and the residue was dissolved in 1N NaOH and washed three times with diethyl ether. The aqueous phase was then acidified to pH 3 with 5N HCl and extracted three times with ethyl acetate. The combined ethyl acetate extracts were dried ($Na_2SO_4$), filtered and concentrated in vacuo to give a yellow oil which was chromatographed over silica gel, eluting with 70% ethyl acetate:hexanes (0.5% acetic acid). The product containing fractions as judged by TLC were combined and concentrated in vacuo. The residue was dissolved in toluene and concentrated in vacuo three times (to remove acetic acid) to yield 4 g (85% yield) of a white solid.

$^1H$ NMR FD-MS, m/e 336 (M+)

Analysis Calculated for $C_{20}H_{20}N_2O_3$; C 71.41 H 5.99 N 8.33 Found C 71.66 H 6.15 N 8.05

C) NMI-D-Phe(αMe)-Pro-Arg-H.HCl

By methods substantially equivalent to those described in Example 27-B, 27-C, 27-G, and 27-H, 1.4 g of NMI-D-Phe(αMe)-Pro-Arg-H.HCl was prepared. The diastereomeric peptides were spearated at the lactam stage (see Example 27-G) by silica gel chromatography (NMI-D-Phe(αMe)-Pro-Arg(Cbz)lactam; TLC $R_f$=0.35, ethyl acetate). NMI-D-Phe(αMe)-Pro-Arg-H.HCl was purified by RPHPLC (95/5 (A/B) to 70/30 (A/B), 180 min; hold to 400 min).

$^1H$ NMR FAB-MS, m/e 574 (MH+)

Analysis Calculated for $C_{31}H_{39}N_7O_4.HCl$; C 61.02 H 6.61 N 16.07 Cl 5.81 Found: C 61.30 H 6.40 N 15.98 Cl 6.09

EXAMPLE 31

Preparation of 1-(ethylsulfonylamino)cyclohexoyl-L-prolinyl-L-arginine aldehyde hydrochloride

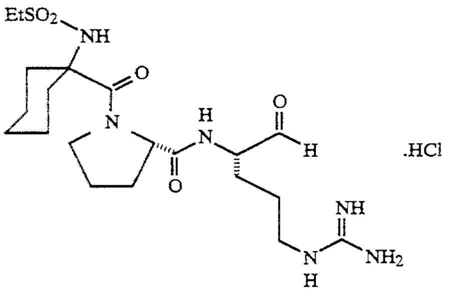

1-(ethylsulfonylamino)cyclohexoyl-Pro-Arg-H.HCl

By methods substantially equivalent to those described in Example 28, 0.95 g of 1-(ethylsulfonylamino)-cyclohexoyl-pro-Arg-H.HCl hydrate was prepared from 1-amino-cyclohexane-1-carboxylic acid. 1-(ethylsulfonylamino)cyclohexoyl-pro-Arg-H.HCl hydrate was purified by RPHPLC (98/2 (A/B) to 80/20 (A/B), 240 min).

$^1$H NMR FAB-MS, m/e 473 (MH+)

Analysis Calc for $C_{20}H_{36}N_6O_5S.HCl.H_2O$ C 45.58 H 7.46 N 15.94 Cl 6.73 Found: C 45.49 H 7.37 N 15.65 Cl 6.54

EXAMPLE 32

Preparation of 1-(1-methylindolyl-2-carbonylamino)cyclohexoyl-L-prolinyl-L-arginine aldehyde hydrochloride

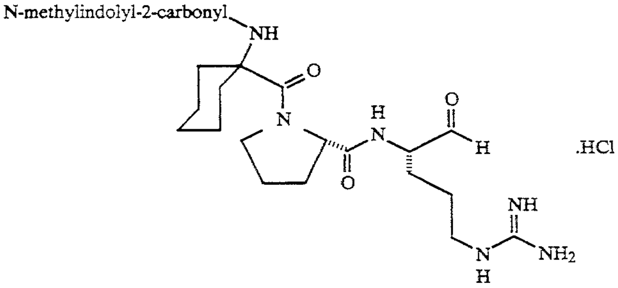

1-(N-methylindolyl-2-carbonylamino ) cyclohexoyl-Pro-Arg-H.HCl

By methods substantially equivalent to those described in Example 30, 1.9 g of 1-(N-methylindolyl-2-carbonylamino) cyclohexoyl-Pro-Arg-H.HCl hydrate was prepared from 1-amino-cyclohexane-1-carboxylic acid. Purification by RPHPLC was not required.

$^1$H NMR FAB-MS, m/e 538 (MH+)

Analysis Calculated for $C_{28}H_{39}N_7O_4.2HCl.1.5H_2O$; C 52.75 H 6.96 N 15.38 Found: C 53.11 H 7.03 N 15.17

EXAMPLE 33

Preparation of N-ethylsulfonylphenylalanyl(αmethyl)-L-prolinyl-L-arginine aldehyde hydrochloride

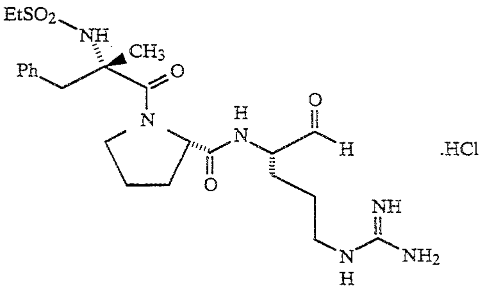

N-EtSO$_2$-Phe(αMe)-Pro-Arg-H.HCl

By methods substantially equivalent to those described in Example 28, 0.73 g of EtSO$_2$-Phe(αMe)-Pro-Arg-H.HCl dihydrate was prepared from EtSO$_2$-Phe(αMe)-Pro-Arg(Cbz)lactam (TLC $R_f$=0.66, 4:1 ethyl acetate:acetonitrile). EtSO$_2$-Phe(αMe)-Pro-Arg-H.HCl dihydrate was purified by RPHPLC (98/2 (A/B) to 85/15 (A/B), 180 min).

$^1$H NMR FAB-MS, m/e 509 (MH+)

Analysis Calc for $C_{23}H_{36}N_6O_5S.HCl.2H_2O$; C 47.54 H 7.11 N 14.46 Cl 6.10 Found: C 47.80 H 6.65 N 14.23 Cl 6.67

EXAMPLE 34

Preparation of N-(1-methylindolyl-2carbonyl)phenylalanyl(αmethyl)-L-prolinyl-L-arginine aldehyde hydrochloride

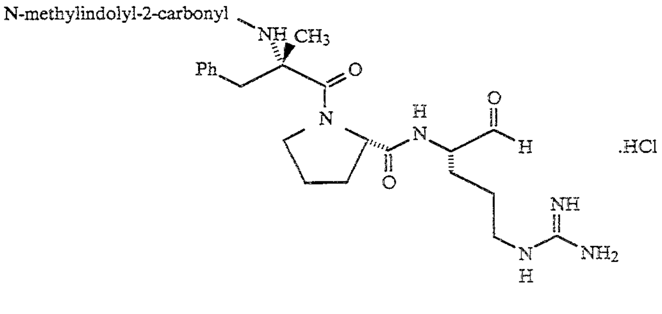

N-methylindolyl-2-carbonyl-Phe(αMe)-Pro-Arg-H.HCl

By methods substantially equivalent to those described in Example 30, 0.29 g of N-methylindolyl-2-carbonyl-Phe(αMe)-Pro-Arg-H.HCl hydrate was prepared from N-methylindolyl-2-carbonyl-Phe(αMe)-Pro-Arg(Cbz)lactam (TLC $R_f$=0.30, ethyl acetate). NMI-Phe(αMe)-Pro-Arg-H.HCl hydrate was purified by RPHPLC (95/5 (A/B) to 70/30 (A/B), 180 min; hold to 400 min).

$^1$H NMR FAB-MS, m/e 574 (MH+)

Analysis Calc for $C_{31}H_{39}N_7O_4$.1.1HCl.1.5$H_2O$; C 58.10 H 6.78 N 15.30 Cl 6.09 Found: C 58.25 H 6.55 N 15.00 Cl 6.25

EXAMPLE 35

Preparation of N-ethoxycarbonyl-D-phenylalanyl(αethyl)-L-prolinyl-L-arginine aldehyde hydrochloride

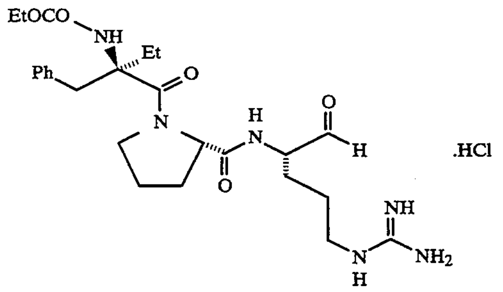

A) N-(diphenylmethylene)Phe-OMe

To a stirring suspension of Phe-OMe.HCl (89.3 g, 414 mmol) in dichloromethane (500 mL) was added a solution of benzophenone imine (75 g, 414 mmol) in dichloromethane (400 mL). After stirring for 16 h, the solution was filtered, washed with water, dried ($Na_2SO_4$) and concentrated in vacuo. The residue was recrystallized from diethyl ether to give 107 g (75% yield) of white solid.

$^1$H NMR FD-MS, m/e 343 (M+)

B) N-(diphenylmethylene)-Phe(αEt)-OMe

To a stirring solution of potassium t-butoxide (9 g, 80 mmol) in tetrahydrofuran (500 mL) at −78° C. was added a solution of N-(diphenylmethylene)Phe-OMe (25 g, 73 mmol) in tetrahydrofuran (250 mL). After 10 min, a solution of ethyl iodide (12.5 g, 80 mmol) in tetrahydrofuran (200 mL) was added. The cold bath was then removed and the solution was allowed to stir for 16 h. The solution was then filtered and the solvent was removed in vacuo. The residue was dissolved in diethyl ether and washed twice with water, once with brine, and then dried ($Na_2SO_4$), filtered and concentrated in vacuo. The residue was chromatographed over silica gel, eluting with a step gradient of 5% ethyl acetate:hexanes through 10% ethyl acetate:hexanes. The product containing fractions as judged by TLC were combined and concentrated in vacuo to yield 18.1 g (70% yield) of a thick yellow oil.

$^1$H NMR FD-MS, m/e 371 (M+)

C) D,L-Phe(αEt)-OMe

To a stirring solution of N-(diphenylmethylene)-Phe(αEt)-OMe (17.6 g, 47.4 mmol) in methanol (200 mL) was added 5N HCl (15 mL, 75 mmol). After 3 h, the solvent was removed in vacuo and the residue was dissolved in water and washed three times with diethyl ether. The aqueous phase was then adjusted to pH 10 with solid $NaHCO_3$ and extracted three times with ethyl acetate. The combined ethyl acetate extracts were then dried ($Na_2SO_4$), filtered and concentrated in vacuo to give 8.75 g (89% yield) of clear, colorless oil.

$^1$H NMR FD-MS, m/e 208 (MH+)

D) D,L-Phe(αEt)-OH

To a stirring solution of D,L-Phe(αEt)-OMe (24 g, 116 mmol) in tetrahydrofuran (200 mL) was added 5N NaOH (24 mL, 120 mmol), followed by water (50 mL) and methanol (50 mL) and the solution was heated to reflux. After 16 h, the solution was cooled to room temperature and the solvents were removed in vacuo. The residue was dissolved in water and washed three times with diethyl ether. The pH was adjusted to 6 with 5N HCl and the solution was concentrated to a volume of about 50 mL in vacuo. The precipitate was filtered, washed with water and dried to give 17.5 g (78% yield) of white solid.

$^1$H NMR FD-MS, m/e 194 (MH+)

Analysis Calculated for $C_{11}H_{15}NO_2$; C 68.37 H 7.82 N 7.25 Found: C 68.58 H 7.65 N 7.41

E) EtOCO-D-Phe(αEt)-Pro-Arg-H.HCl

By methods substantially equivalent to those described in Example 27, 2.65 g of EtOCO-D-Phe(αEt)-Pro-Arg-H.HCl ethanolate was prepared from D,L-Phe(αEt)-OH. Purification of EtOCO-D-Phe(αEt)-Pro-Arg-H.HCl ethanolate by RPHPLC was not required. The diastereomeric peptides were separated at the dipeptide ester stage (see Example 27-B) by silica gel chromatography (EtOCO-D-Phe(αEt)-Pro-OBzl; TLC $R_f$=0.66, 50% ethyl acetate:hexanes).

$^1$H NMR FAB-MS, m/e 503 (MH+)

Analysis Calc for $C_{25}H_{38}N_6O_5$.1.1HCl.0.5EtOH; C 55.20 H 7.50 N 14.85 Cl 6.89 Found: C 55.19 H 7.13 N 14.55 Cl 6.79

EXAMPLE 36

Preparation of N-ethoxycarbonylphenylalanyl(αethyl)-L-prolinyl-L-arginine aldehyde hydrochloride

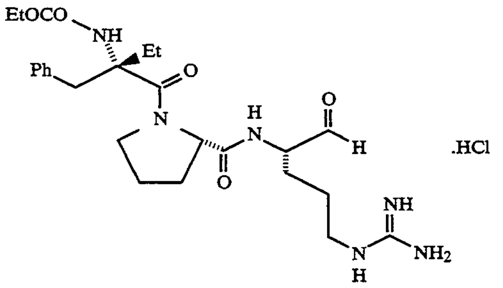

EtOCO-Phe(αEt)-Pro-Arg-H.HCl

By methods substantially equivalent to those described in Example 35, 2.15 g of EtOCO-Phe(αEt)-Pro-Arg-H.HCl ethanolate were prepared from EtOCO-Phe(αEt)-Pro-OBzl (TLC $R_f$=0.77, 50% ethyl acetate:hexanes). Purification of EtOCO-Phe(αEt)-Pro-Arg-H.HCl ethanolate by RPHPLC was not required.

$^1$H NMR FAB-MS, m/e 503 (MH+)

Analysis Calculated for $C_{25}H_{38}N_6O_5$.2HCl.0.5EtOH; C 52.17 H 7.24 N 14.04 Found: C 52.33 H 6.96 N 13.99

EXAMPLE 37

Preparation of N-ethoxycarbonyl-D-phenylalanyl (αn-propyl)-L-prolinyl-L-arginine aldehyde hydrochloride

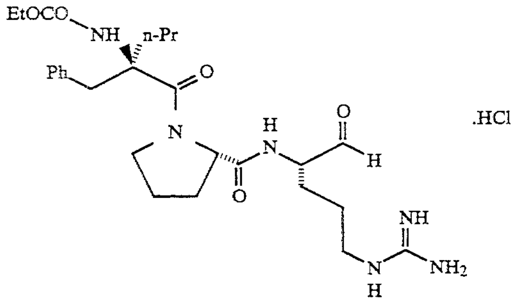

A) D,L-Phe(αn-Pr)-OMe

By methods substantially equivalent to those described in Example 35-A and 35-B, 10.1 g (63%) of D,L-Phe(αn-Pr)-OMe was prepared from N-(diphenylmethylene)-Phe-OMe and n-propyl iodide.

$^1$H NMR FD-MS, m/e 222 ($MH^+$)

B) EtOCO-D,L-Phe(αn-Pr)-OH

To a stirring solution of D,L-Phe(αn-Pr)-OMe (9 g, 41 mmol) in tetrahydrofuran (250 mL) at 0° C. was added N,N-diisopropylethylamine (5.3 g, 41 mmol) followed by ethyl chloroformate (4.4 g, 41 mmol). After 3.5 h, the solvent was removed in vacuo and the residue was dissolved in ethyl acetate. The organic phase was washed twice with saturated aqueous $NaHCO_3$, once with brine, and then dried ($Na_2SO_4$), filtered and concentrated in vacuo.

The residue was dissolved in tetrahydrofuran (120 mL) and to this solution was added 5N NaOH (11 mL, 55 mmol) with vigorous stirring, followed by methanol (30 mL). The solution was heated to 55° C. and allowed to stir for 48 h. The solution was then cooled to room temperature and the solvents were removed in vacuo. The residue was dissolved in water and washed twice with diethyl ether. The aqueous phase was adjusted to pH 3 with conc. HCl and extracted twice with ethyl acetate. The combined ethyl acetate extracts were dried ($Na_2SO_4$), filtered and concentrated in vacuo to yield 10.3 g (91%) of a yellow solid.

$^1$H NMR FD-MS, m/e 279 ($M^+$)

C) EtOCO-D-Phe(αn-Pr)-Pro-Arg-H.HCl

By methods substantially equivalent to those described in Example 27-B, 27-C, 27-G and 27-H, 0.69 g of EtOCO-D-Phe(αn-Pr)-Pro-Arg-H.HCl was prepared. The diastereomeric peptides were separated at the dipeptide ester stage (see Example 27-B) by silica gel chromatography (EtOCO-D-Phe(αn-Pr)-Pro-OBzl; TLC Rf=0.77, 50% ethyl acetate:hexanes). EtOCO-D-Phe(αn-Pr)-Pro-Arg-H.HCl was purified by RPHPLC (98/2 (A/B), 60 min; to 80/20 (A/B), 300 min).

$^1$H NMR FAB-MS, m/e 517 ($MH^+$)

Analysis Calculated for $C_{26}H_{40}N_6O_5$.HCl;

C 56.46 H 7.47 N 15.19 Pound: C 56.22 H 7.41 N 15.11

EXAMPLE 38

Preparation of N-ethoxycarbonylphenylalanyl(αn-propyl)-L-prolinyl-L-arginine aldehyde hydrochloride

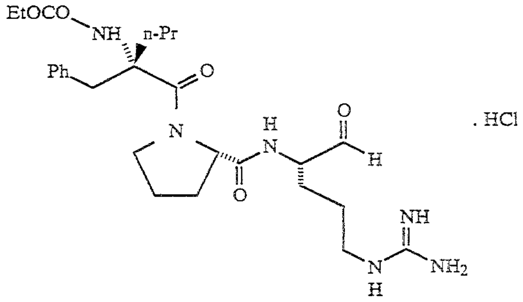

EtOCO-Phe(αn-Pr)-Pro-Arg-H.HCl

By methods substantially equivalent to those described in Example 37, 0.34 g of EtOCO-Phe(αn-Pr)-Pro-Arg-H.HCl was prepared from EtOCO-Phe(αn-Pr)-Pro-OBzl (TLC $R_f$=0.67, 50% ethyl acetate:hexanes). EtOCO-Phe(αn-Pr)-Pro-Arg-H.HCl was purified by RPHPLC (98/2 (A/B), 60 min; to 80/20 (A/B), 300 min).

$^1$H NMR FAB-MS, m/e 517 ($MH^+$)

Analysis Calculated for $C_{26}H_{40}N_6O_5$.HCl; C 56.46 H 7.47 N 15.19 Found: C 56.75 H 7.55 N 15.47

EXAMPLE 39

Preparation of N-ethoxycarbonyl-D-phenylalanyl(αn-butyl)-L-prolinyl-L-arginine aldehyde hydrochloride

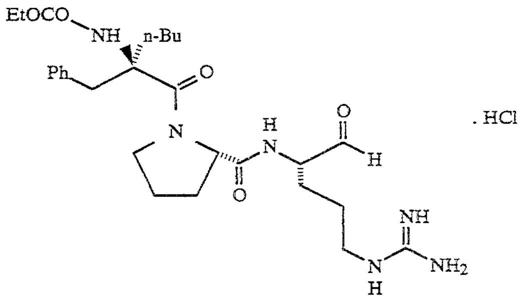

EtOCO-D-Phe(αn-Bu)-Pro-Arg-H.HCl

By methods substantially equivalent to those described in Example 37, 2.2 g of EtOCO-D-Phe(αn-Bu)-Pro-Arg-H.HCl was prepared, starting with N-(diphenylmethylene)-Phe-OMe and n-butyl iodide. The diastereomeric peptides were separated at the dipeptide ester stage (see Example 27-B) by silica gel chromatography (EtOCO-D-Phe(αn-Bu)-Pro-OBzl; TLC Rf=0.86, 50% ethyl acetate:hexanes). EtOCO-D-Phe(αn-Bu)-Pro-Arg-H.HCl was purified by RPHPLC (98/2 (A/B), 60 min; to 85/15 (A/B), 300 min).

$^1$H NMR FAB-MS, m/e 531 ($MH^+$)

Analysis Calculated for $C_{27}H_{42}N_6O_5$.HCl; C 57.18 H 7.64 N 14.82 Found: C 57.32 H 7.74 N 14.95

EXAMPLE 40

Preparation of N-ethoxycarbonylphenylalanyl(αn-butyl)-L-prolinyl-L-arginine aldehyde

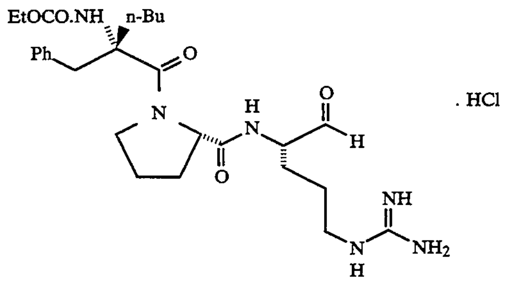

EtOCO-Phe(αn-Bu)-Pro-Arg-H.HCl

By methods substantially equivalent to those described in Example 39, 1.47 g of EtOCO-Phe(αn-Bu)-Pro-Arg-H.HCl was prepared from EtOCO-Phe(αn-Bu)-Pro-OBzl (TLC $R_f$=0.74, 50% ethyl acetate:hexanes). EtOCO-Phe(αn-Bu)-Pro-Arg-H.HCl was purified by RPHPLC (98/2 (A/B), 60 min; to 85/15 (A/B), 300 min).

$^1$H NMR FAB-MS, m/e 531 ($MH^+$)

Analysis Calculated for $C_{27}H_{42}N_6O_5$.HCl; C 57.18 H 7.64 N 14.82 Found: C 56.92 H 7.59 N 14.76

EXAMPLE 41

Preparation of N-ethylsulfonyl-(D,L)-phenylglycinyl(αmethyl)-L-prolinyl-L-arginine aldehyde hydrochloride

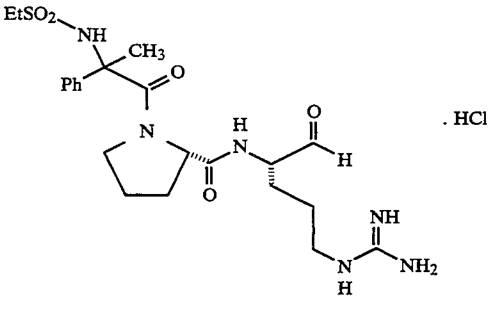

$EtSO_2$-D,L-Phg(αMe)-Pro-Arg-H.HCl

By methods substantially equivalent to those described in Example 37, 0.21 g of $EtSO_2$-D,L-Phg(αMe)-Pro-Arg-H.HCl hydrate was prepared starting from D,L-Phg-OMe.HCl and using $EtSO_2Cl$ in place of EtOCOCl, and $CH_3I$ in place of n-propyliodide. $EtSO_2$-D,L-Phg(αMe)-Pro-Arg-H.HCl hydrate was purified by RPHPLC (98/2 (A/B), 30 min; to 80/20 (A/B), 240 min). The diastereomers could not be separated during the course of this synthesis and thus, the product was prepared and tested as a mixture of isomers.

$^1$H NMR FAB-MS, m/e 495 ($MH^+$)

Analysis Calculated for $C_{22}H_{34}N_6O_5S$.1.2HCl.$H_2O$; C 47.49 H 6.74 N 15.10 Found: C 47.50 H 6.44 N 14.91

EXAMPLE 42

Preparation of N-ethoxycarbonylglycinyl(α,αdi-n-butyl)-L-prolinyl-L-arginine aldehyde hydrochloride

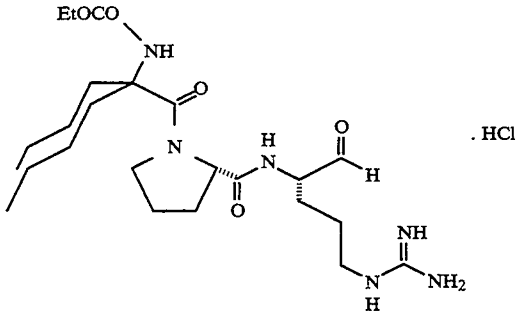

EtOCO-Gly(α,αdi-n-Bu)-Pro-Arg-H.HCl

By methods substantially equivalent to those described in Example 37, 1.4 g of EtOCO-Gly(α,αdi-n-Bu)-Pro-Arg-H.HCl hydrate was prepared starting with N-(diphenylmethylene)Gly-OEt and two equivalents of n-butyl iodide. Reduction of the intermediate EtOCO-Gly (α,αdi-n-Bu)-Pro-Arg(Cbz)lactam was accomplished by a method similar to that described in Example 27-G, except lithium aluminum hydride was used as the reducing agent at −78° C. EtOCO-Gly(α,αdi-n-Bu)-Pro-Arg-H.HCl hydrate was purified by RPHPLC (98/2 (A/B), 60 min; to 80/20 (A/B), 320 min).

$^1$H NMR FAB-MS, m/e 497 ($MH^+$)

Analysis Calc for $C_{24}H_{44}N_6O_5$.1.2HCl.$H_2O$; C 51.62 H 8.52 N 15.05 Cl 7.62 Found: C 51.82 H 7.91 N 14.69 Cl 7.75

EXAMPLE 43

Preparation of N-methylsulfonyl-D-phenylalanyl(αmethyl)-L-prolinyl-L-arginine aldehyde hydrochloride

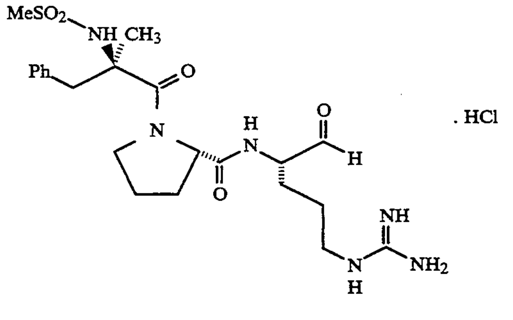

$MeSO_2$-D-Phe(αMe)-Pro-Arg-H.HCl

By methods substantially equivalent to those described in Example 28, 0.16 g of $MeSO_2$-D-Phe(αMe)-Pro-Arg-H.HCl hydrate was prepared, using $MeSO_2Cl$ in place of $EtSO_2Cl$. The diastereomeric peptides were separated at the tripeptide arginine aldehyde stage by RPHPLC (98/2 (A/B), 80 min; up to 85/15 (A/B), 320 min). Stereochemistry is tentatively assigned based on the thrombin inhibitory activity of Example 43 and Example 44.

$^1$H NMR FAB-MS, m/e 495 ($MH^+$)

Analysis Calc for $C_{22}H_{34}N_6O_5S.1.1HCl.H_2O$; C 47.81 H 6.77 N 15.20 Cl 7.06 Found: C 47.73 H 6.45 N 15.25 Cl 7.12

EXAMPLE 44

Preparation of N-methylsulfonylphenylalanyl(αmethyl)-L-prolinyl-L-arginine aldehyde hydrochloride

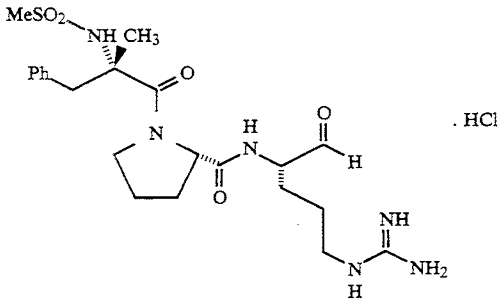

$MeSO_2$-Phe(αMe)-Pro-Arg-H.HCl

By methods substantially equivalent to those described in Example 28, 0.16 g of $MeSO_2$-Phe(αMe)-Pro-Arg-H.HCl hydrate was prepared, using $MeSO_2Cl$ in place of $EtSO_2Cl$. The diastereomeric peptides were separated at the tripeptide arginine aldehyde stage by RPHPLC (98/2 (A/B), 80 min; up to 85/15 (A/B), 320 min). Stereochemistry is tentatively assigned based on the thrombin inhibitory activity of Example 43 and Example 44.

$^1H$ NMR NAB-MS, m/e 495 (MH+)

Analysis Calc for $C_{22}H_{34}N_6O_5S.1.1HCl.H_2O$; C 47.81 H 6.77 N 15.20 Cl 7.06 Found C 47.81 H 6.38 N 14.96 Cl 7.06

EXAMPLE 45

Preparation of N-(1-methylindolyl-2-carbonyl)-D-phenylalanyl-L-Prolinyl-L-Arginine Aldehyde Hydrochloride

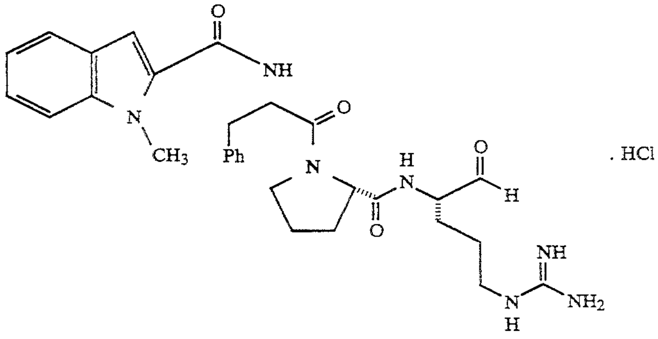

A) Boc-D-Phe-Pro-OBzl

To a solution of Boc-D-Phe-OH (89.1 g, 336 mmol), Pro-OBzl.HCl (81.2g, 336 mmol), HOBT (50 g, 370 mmol) and N,N-diisopropylethylamine (176 mL, 1,008 mmol) at 0° C. in dichloromethane (600 mL) was added 1-(3-dimethylaminopropyl)-3-ethylcarbodiimide.HCl (71 g, 370 mmol). After stirring for 18 h, the mixture was diluted with diethyl ether 1 L) and washed three times with 1N citric acid (250 mL), once with water (250 mL), three times with sat'd aqueous $NaHCO_3$ (250 mL) and once with sat'd aqueous NaCl (250 mL). The organic phase was dried ($Na_2SO_4$), filtered, and concentrated in vacuo to yield 140 g (92.5%) of a pale yelow foam.

FD-MS, m/e 452 (M+) $^1H$ NMR

B) TFA. D-Phe-Pro-OBzl

To a stirring solution of Boc-D-Phe-Pro-OBzl (68 g, 150 mmol) in dichloromethane (50 mL) at 0° C., was added anisole (20 mL) followed by trifluoroacetic acid (400 mL). After sirring for 3 h, the solvents were evaporated in vacuo and the thick oily residue was dissolved in diethyl ether (1.5 L) and refrigerated (72 h). The white precipitate was filtered, washed with diethyl ether (300 mL) and dried to yield 59.4 g (85%) of white powder.

$^1H$ NMR

C) NMI-D-Phe-Pro-OBzl

To a solution of N-methylindole-2-carboxylic acid (2.6 g, 14.9 mmol) in dry tetrahydrofuran (45 mL) was added pentafluorophenol (3 g, 16.5 mmol), followed by 1-(3-dimethylaminopropyl)-3-ethylcarbodiimide (3.2 g, 16.5 mmol). The mixture was allowed to stir at reflux for 3.5 h and then cooled to room temperature. Then, to this mixture was added a solution of TFA. D-Phe-Pro-OBzl (7 g, 14.9 mmol) and N,N-diisopropylethyl amine (4 g, 30 mmol) in tetrahydrofuran (25 mL). After stirring for an additional 2 h, the solvents were removed in vacuo and the residue was dissolved in ethyl acetate (500 mL), then washed three times with 0.1N aqueous $NaHSO_4$ (250 mL) and three times with 1N aqueous $K_2CO_3$ (250 mL). The organic phase was dried ($Na_2SO_4$), filtered, and concentrated in vacuo to give 6.5 g of amorphous solid (a mixture of the desired product, contaminated with pentafluorophenol).

$^1H$ NMR FD-MS, m/e 509 (M+)

D) NMI-D-Phe-Pro-OH

To a stirring solution of NMI-D-Phe-Pro-OBzl (8.8 g, 17.3 mmol) in p-dioxane (150 mL) was added a solution of $LiOH.H_2O$ (3.6 g, 86.3 mmol) in water (75 mL). After stirring for 4 h, the volume of the solution was reduced to about 50 mL in vacuo, and the solution was diluted with 1N NaOH (10 mL). The aqueous phase was washed three times with diethyl ether and then acidified to pH 2 with 5N HCl, and then extracted three times with ethyl acetate. The combined ethyl acetate extracts were washed with sat'd aqueous NaCl (200 mL), dried ($MgSO_4$), filtered and concentrated to give 5.4 g (75%) of white solid.

$^1H$ NMR FD-MS, m/e 419 (M+)

E) Boc-Arg(Cbz)-OH

Boc-Arg(HCl)-OH (82.1 g, 250 mmol) was dissolved in 5N NaOH (240 mL) in a 3 necked flask. The reaction mixture was chilled to −5° C. and the pH was maintained at 13.2–13.5 using 5N NaOH (250 mL) while adding benzyl chloroformate (143 mL, 1.0 mol) dropwise (55 min). The reaction mixture was stirred for an additional 1 hour at −5° C. and diluted with water (100 mL) and diethyl ether (500 mL). The aqueous layer was separated and extracted twice with diethyl ether (500 mL). The aqueous layer was then acidified to pH 3.0 with 3N $H_2SO_4$ (560 mL) and extracted with ethyl acetate (550 mL). The aqueous layer was separated and extracted once with ethyl acetate. The combined ethyl acetae layers were washed with water, dried ($MgSO_4$) and concentrated in vacuo to give 66.1 g (65%) of a white solid:

$^1H$ NMR FD-MS 408 (M+)

F) Boc-Arg(Cbz)-Lactam

Boc-Arg(Cbz)-OH (66.0 g, 0.162 mol) was dissolved in tetrahydrofuran (230 mL) and cooled to −10° C. To this solution was added N-methylmorpholine (18.7 mL, 0.17 mol) followed by isobutyl chloroformate (22.5 mL, 0.17 mol). After stirring 5 minutes at −10° C., triethylamine (23.5 mL, 0.17 mol) was added. After an additional 1 hour at −10° C., the mixture was allowed to warm to room temperature and stirring continued for 1 h at room temperature. The reaction mixture was then poured into 1 L of ice-water and the resulting precipitate was filtered, washed with cold water, and dried in vacuo. The product was crystallized from ethyl acetate to give 38 g (60%) of a white solid.

$^1H$ NMR FD-MS 391 (MH+)

G) 2HCl.Arg(Cbz)-Lactam

A solution of HCl(g) saturated in-ethyl acetae (7.2 L) was added dropwise over 30 minutes to a solution of Boc-Arg(Cbz)-Lactam (641 g, 1.64 mol) dissolved in dichloromethane (3 L) at −10° C. After 1 h at −10° C. the cold bath was removed and the solution was allowed to warm to room temperature over 3 h. Diethyl ether (12 L) was added and the resulting precipitate was filtered, washed with diethyl ether, and dried in vacuo to give 580 g (97%)

FD-MS 291 (MH+)

H) NMI-D-Phe-Pro-Arg(Cbz)lactam

In flask 1, NMI-D-Phe-Pro-OH (5.3 g, 12.5 mmol) was dissolved in dimethylformamide (60 mL), cooled to −15° C. and N-methylmorpholine (1.3 g, 12.5 mmol) was added, followed by isobutyl chloroformate (1.7 g, 12.5 mmol). The reaction mixture was allowed to stir at −15° C. for 10 min.

In flask 2, 2HCl.Arg(Cbz)-Lactam (4.5 g, 12.5 mmol) was dissolved in dimethylformamide (60 mL), cooled to 0° C., and N,N-diisopropylethylamine (3.2 g, 25 mmol) was added.

The contents of flask 2 were added to flask 1 in one portion and then the cold bath was left unattended and the reaction mixture was allowed to slowly warm to room temperature (24 h). Then saturated aqueous $NaHCO_3$ (100 mL) was added and the solvent was removed in vacuo. The residue was partitioned between ethyl acetate and water and the layers were separated. The organic layer was washed twice with 0.01N HCl, twice with saturated $NaHCO_3$, and once with brine. The organic layer was dried ($Na_2SO_4$), and the filtrate was concentrated in vacuo. The residue was chromatographed over silica gel, eluting with 95:5 ethyl acetate:acetonitrile and then the product containing fractions (as judged by TLC) were combined and concentrated to give 5 g (58%) of a light yellow foam.

$^1H$ NMR FD-MS, m/e 691 (M+)

Analysis Calculated for $C_{38}H_{41}N_7O_6$; C 65.98, H 5.97, N 14.17; Found; C 66.28, H 6.11, N 13.94.

I) NMI-D-Phe-Pro-Arg-H.HCl

To a stirring solution of NMI-D-Phe-Pro-Arg(Cbz)lactam (4.8 g, 6.9 mmol) in tetrahydrofuran (60 mL) at −78° C., was slowly added a solution of 1N lithium aluminum hydride (4.8 mL, 4.8 mmol) in tetrahydrofuran. After 30 min, the reaction mixture was poured into a stirring solution of cold 1N HCl (10 mL) and tetrahydrofuran (25 mL). The solution was then diluted with sat'd aqueous NaCl (50 mL) and extracted twice with ethyl acetate (100 mL). The combined ethyl acetate extracts were dried ($MgSO_4$), filtered and concentrated to give 5.4 g of a yellow foam.

The foam was then dissolved in ethanol (75 mL) and water (25 mL) and this solution was added to a stirring solution of ethanol (75 mL), water (25 mL) and 1N HCl (10 mL). To this stirring solution was then added 5% Pd on carbon (2.4 g). $H_2$ was then bubbled through the solution for 1.5 h, and then the reaction was flushed with $N_2$ and filtered over a pad of Celite ®. The ethanol was removed in vacuo at 35° C. and then the residue was redissolved in water (25 mL). The pH of the aqueous solution was adjusted to 4.1 with Bio Rad ion exchange resin (basic form), filtered and lyophilized to give 3.4 g of a fluffy pale yellow solid. The product was then purified by RPHPLC (80/20 (A/B), 80 min; ramping up to 65/35 (A/B), 320 min; hold to 380 min, up to 0/100 (A/B) 440 min, hold to 500 min) to give 1.97 g (73%) of pure NMI-D-Phe-Pro-Arg-H.HCl hydrate.

$^1H$ NMR FAB-MS, m/e 560 (MH+)

Analysis Calculated for $C_{30}H_{37}N_7O_4.H_2O.1.2HCl$; C 57.98, H 6.52, N 15.78; Found; C 58.25, H 6.61, N 15.33.

EXAMPLE 46

Preparation of N-(isoquinolinyl-2-carbonyl)-D-phenylalanyl-L-Prolinyl-L-Arginine Aldehyde Hydrochloride

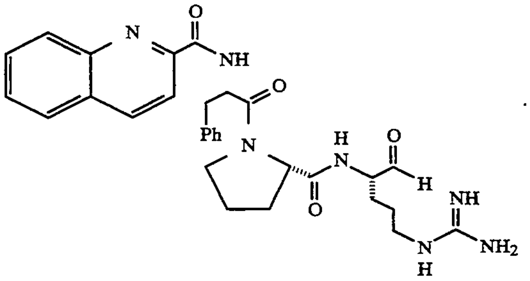

. HCl

N-(isoquinolinyl-2-carbonyl)-D-Phe-Pro-Arg-H.HCl

By methods substantially equivalent to those described in Example 45-C, 45-D, 45-H and 45-I, 2.2 g of N-(isoquinoline-2-carbonyl)-D-Phe-Pro-Arg-H.HCl was prepared using isoquinoline-2-carboxylic acid in place of N-methylindole-2-carboxylic acid. N-(isoquinolinyl-2-carbonyl)-D-Phe-pro-Arg-H.HCl was purified by RPHPLC (90/10 (A/B), 90 min; ramp to 70/30 (A/B), 390 min; ramp to 0/100 (A/B), 450 min; hold to 510 min).

$^1H$ NMR FAB-MS, m/e 558 (MH+)

Analysis Calc. for $C_{30}H_{35}N_7O_4.1.1HCl.0.5H_2O$; C 59.39, H 6.16, N 16.16, Cl 6.43; Found; C 59.62, H 5.98, N 16.11, Cl 6.38.

EXAMPLE 47

Preparation of N-(nicotinoyl)-D-phenylalanyl-L-Prolinyl-L-Arginine Aldehyde Hydrochloride

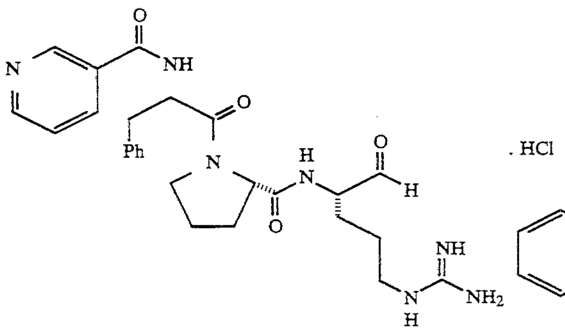

N-Nicotinoyl-D-Phe-Pro-Arg-H.HCl

By methods substantially equivalent to those described in Example 45-C, 45-D, 45-H and 45-I, 2.8 g of N-Nicotinoyl-D-Phe-Pro-Arg-H.HCl hydrate was prepared using nicotinic acid in place of N-methylindole-2-carboxylic acid.

$^1$H NMR FAB-MS, m/e 508 (MH+)

Analysis Calc. for $C_{26}H_{33}N_7O_4.1.3HCl.H_2O$; C 54.50, H 6.39, N 17.11; Found; C 54.85, H 6.14, N 16.74.

EXAMPLE 48

Preparation of N-(3-pyridylacetyl)-D-phenylalanyl-L-Prolinyl-L-Arginine Aldehyde Hydrochloride

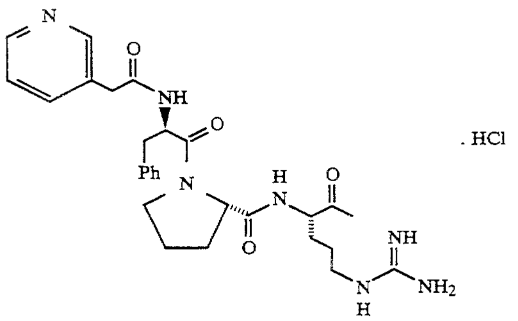

N-(α-(3-pyridyl)-acetyl)-D-Phe-Pro-Arg-H.HCl

By methods substantially equivalent to those described in Example 45-C, 45-D, 45-H and 45-I, 2.2 g of N-(α-(3-pyridyl)-acetyl)-D-Phe-Pro-Arg-H.HCl hydrate was prepared using α-(3-pyridyl)-acetic acid in place of N-methylindole-2-carboxylic acid. Also, the reduction of the tripeptide arginine lactam was performed using $LiAl(O\text{-}t\text{-}Bu)_3H$ at −23° C., rather than LAH at −78° C.

$^1$H NMR FAB-MS, m/e 523 (MH+)

Analysis Calc. for $C_{27}H_{35}N_7O_4.2.4HCl.3.5H_2O$; C 48.25, H 6.66, N 14.59, Cl 12.66; Found; C 48.60, H 6.34, N 14.32, Cl 12.86.

EXAMPLE 49

Preparation of N-(1-methylindolyl-2-carbonyl)-D-cyclohexylalanyl-L-Prolinyl-L-Arginine Aldehyde Hydrochlonde

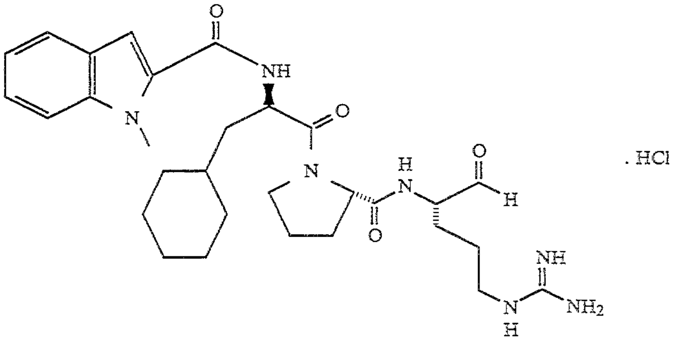

NMI-D-Cha-Pro-Arg-H.HCl

By methods substantially equivalent to those described in Example 45-A, 45-B, 45-C, 45-D, 45-H and 45-I, 2.14 g of NMI-D-Cha-Pro-Arg-H.HCl hydrate was prepared using Boc-D-Cha-OH in place of Boc-D-Phe-OH. Also, the tripeptide arginine lactam was reduced with $LiAl(O\text{-}t\text{-}Bu)_3H$ at −23° C. rather than LAH at −78° C.

$^1$H NMR FAB-MS, m/e 566 (MH+)

Analysis Calc. for $C_{30}H_{43}N_7O_4.1.2HCl$; C 59.12, H 7.31, N 16.09, Cl 6.98; Found; C 59.17, H 7.04, N 15.88, Cl 6.95.

EXAMPLE 50

Preparation of N-(isoquinolinyl-2-carbonyl)-D-cyclohexylalanyl-L-Prolinyl-L-Arginine Aldehyde Hydrochloride

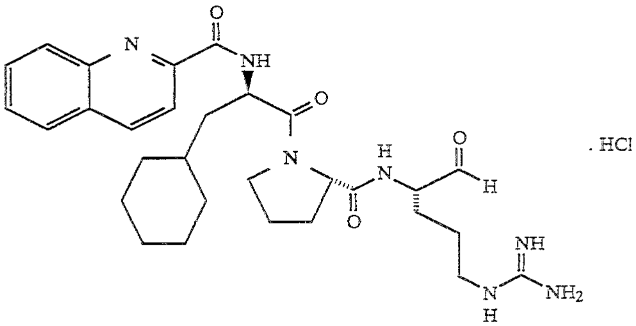

N-(isoquinolinyl-2-carbonyl)-D-Cha-Pro-Arg-H.HCl

By methods substantially equivalent to those described in Example 45, 3.2 g of N-(isoquinoline-2-carbonyl)-D-Cha-Pro-Arg-H.HCl hydrate was prepared using Boc-D-Cha-OH in place of Boc-D-Phe-OH, and using isoquinoline-2-carboxylic acid in place of N-methylindole-2-carboxylic acid. Also, the tripeptide arginine lactam was reduced with $LiAl(O\text{-}t\text{-}Bu)_3H$ at −23° C. rather than LAH at −78° C.

$^1$H NMR FAB-MS, m/e 565 (MH+)

Analysis Calc. for $C_{30}H_{41}N_7O_4.1.3HCl.1.1H_2O$; C 57.11, H 7.11, N 15.54, Cl 7.31; Found; C 57.04, H 6.74, N 15.36, Cl 6.93.

EXAMPLE 51

Preparation of N-(methylsulfonyl)-D-phenylalanyl-L-Prolinyl-L-Arginine Aldehyde Hydrochloride

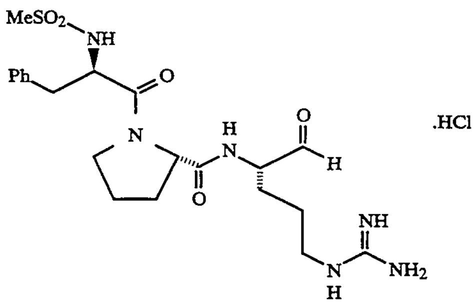

A) $MeSO_2$-D-Phe-Pro-OBzl

To a stirring solution of TFA.D-Phe-Pro-OBzl (10 g, 21.4 mmol) in tetrahydrofuran (100 mL) at 0° C., was added N,N-diisopropylethylamine (15 mL, 85 mmol), followed by methanesulfonyl chloride (2 mL, 24 mmol). The cold bath was left unattended and the reaction was allowed to warm slowly to room temperature. After stirring for 24 h, the solvent was removed in vacuo and the residue was dissovled in ethyl acetate (200 mL). The ethyl acetate solution was washed twice with 1N citric acid (100 mL), once with water (100 mL), twice with saturated aqueous $NaHCO_3$ (100 mL) and once with brine (100 mL). The organic solution was then dried with $MgSO_4$, filtered and concentrated. The resulting foam was purified by chromatography over silica gel, eluting with 1:1 hexanes/ethyl acetate. The product containing fractions as judged by TLC were combined and concentrated to give 7.2 g (79%) of an off white foam.

$^1$H NMR FD-MS, m/e 430 (M+)

Analysis Calculated for $C_{22}H_{26}N_2O_5S$; C 61.38, H 6.09, N 6.51; Found; C 61.61, H 6.01, N 6.44.

B) $MeSO_2$-D-Phe-Pro-Arg-H.HCl

By methods substantially equivalent to those described in Example 45-D, 45-H and 45-I, 310 mg of $MeSO_2$-D-Phe-Pro-Arg-H.HCl hydrate was prepared from $MeSO_2$-D-Phe-Pro-OBzl. $MeSO_2$-D-Phe-Pro-Arg-H.HCl was purified by RPHPLC (98/2 (A/B), ramp to 60/40 (A/B), 360 min).

$^1$H NMR FAB-MS, m/e 481 (MH+)

Analysis Calc. for $C_{21}H_{32}N_6O_5S.HCl.H_2O$; C 47.14, H 6.59, N 15.71; Found; C 47.33, H 6.49, N 15.66.

EXAMPLE 52

Preparation of N-(ethylsulfonyl)-D-phenylalanyl-L-Prolinyl-L-Arginine Aldehyde Hydrochloride

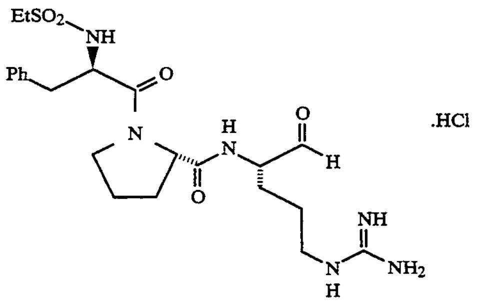

$EtSO_2$-D-Phe-Pro-Arg-H.HCl

By methods substantially equivalent to those described in Example 51, 0.5 g of $EtSO_2$-D-Phe-Pro-Arg-H.HCl hydrate was prepared using $EtSO_2Cl$ in place of $MeSO_2Cl$. $EtSO_2$-D-Phe-Pro-Arg-H.HCl was purified by RPHPLC (98/2 (A/B), 30 min; ramp to 80/20 (A/B), 270 min).

$^1$H NMR FAB-MS, m/e 495 (MH+)

Analysis Calc. for $C_{22}H_{34}N_6O_5S.2HCl.1.5H_2O$; C 44.56, H 6.37, N 14.17; Found; C 44.73, H 6.41, N 14.08.

EXAMPLE 53

Preparation of N-(n-propylsulfonyl)-D-phenylalanyl-L-Prolinyl-L-Arginine Aldehyde Hydrochloride

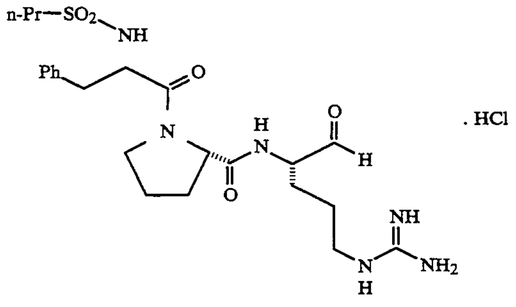

n-Pr-$SO_2$-D-Phe-Pro-Arg-H.HCl

By methods substantially equivalent to those described in Example 51, 0.47 g of n-Pr-$SO_2$-D-Phe-Pro-Arg-H.HCl hydrate was prepared using n-Pr-$SO_2Cl$ in place of $MeSO_2Cl$. n-Pr-$SO_2$-D-Phe-Pro-Arg-H.HCl was purified by RPHPLC (98/2 (A/B), ramp to 60/40 (A/B), 240 min).

$^1$H NMR FAB-MS, m/e 509 (MH+)

Analysis Calc. for $C_{23}H_{36}N_6O_5S.HCl.1.5H_2O$; C 48.29, H 7.05, N 14.69; Found; C 48.00 H 6.71 N 14.54

EXAMPLE 54

Preparation of N-(n-butylsulfonyl)-D-phenylalanyl-L-Prolinyl-L-Arginine Aldehyde Hydrochloride

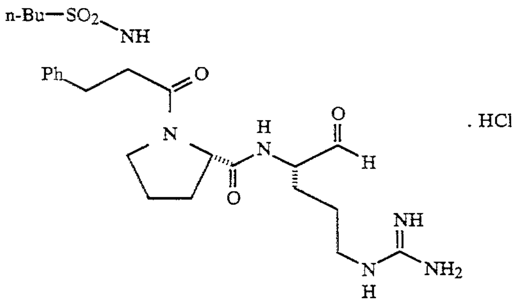

n-Bu-$SO_2$-D-Phe-Pro-Arg-H.HCl

By methods substantially equivalent to those described in Example 51, 0.94 g of n-Bu-$SO_2$-D-Phe-Pro-Arg-H.HCl was prepared using n-Bu-$SO_2$Cl in place of $MeSO_2Cl$. n-Bu-$SO_2$-D-Phe-Pro-Arg-H.HCl was purified by RPHPLC (98/2 (A/B), ramp to 60/40 (A/B), 240 min).

$^1$H NMR FAB-MS, m/e 523 (MH+)

Analysis Calc. for $C_{24}H_{38}N_6O_5S$.HCl; C 51.56, H 7.03, N 15.03; Found; C 51.65, H 7.22, N 14.79.

EXAMPLE 55

Preparation of N-(isopropylsulfonyl)-D-phenylalanyl-L-Prolinyl-L-Arginine Aldehyde Hydrochloride

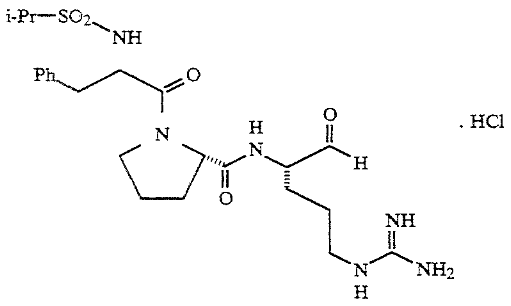

i-Pr-$SO_2$-D-Phe-Pro-Arg-H.HCl

By methods substantially equivalent to those described in Example 51, 1 g of i-Pr-$SO_2$-D-Phe-Pro-Arg-H.HCl hydrate was prepared using i-Pr-$SO_2$Cl in place of $MeSO_2Cl$. i-Pr-$SO_2$-D-Phe-Pro-Arg-H.HCl was purified by RPHPLC (98/2 (A/B), ramp to 60/40 (A/B), 240 min).

$^1$H NMR FAB-MS, m/e 509 (MH+)

Analysis Calc. for $C_{23}H_{37}N_6O_5S$.HCl.1.25$H_2O$; C 48.67, H 7.01, N 14.80; Found; C 48.83, H 6.85, N 14.91.

EXAMPLE 56

Preparation of N-(dimethylaminosulfonyl)-D-phenylalanyl-L-Prolinyl-L-Arginine Aldehyde Hydrochloride

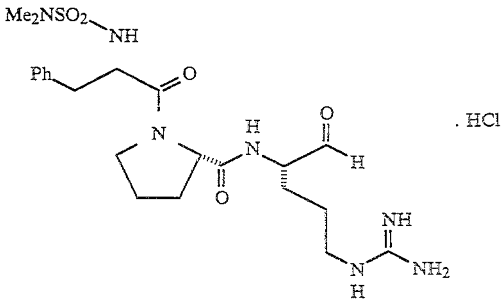

$Me_2NSO_2$-D-Phe-Pro-Arg-H.HCl

By methods substantially equivalent to those described in Example 51, 1.1 g of $Me_2NSO_2$-D-Phe-Pro-Arg-H.HCl hydrate was prepared using $Me_2NSO_2Cl$ in place of $MeSO_2Cl$. Also, the tripeptide arginine lactam was reduced with LiAl(O-t-Bu)$_3$H at −23° C. rather than LAH at −78° C. $Me_2NSO_2$-D-Phe-Pro-Arg-H.HCl was purified by RPHPLC (98/2 (A/B), ramp to 60/40 (A/B), 240 min).

$^1$H NMR FAB-MS, m/e 510 (MH+)

Analysis Calc. for $C_{22}H_{35}N_7O_5S$.HCl.$H_2O$; C 44.27, H 6.57, N 16.08, Cl 11.28; Found; C 44.55, H 5.89, N 16.05, Cl 10.82.

EXAMPLE 57

Preparation of N-(phenylsulfonyl)-D-phenylalanyl-L-Prolinyl-L-Arginine Aldehyde Hydrochloride

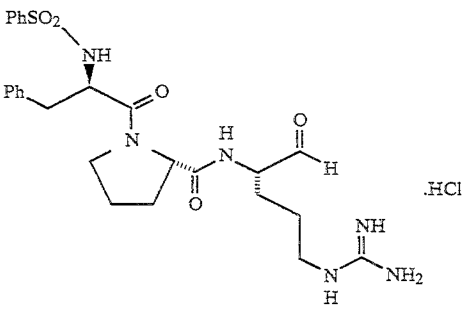

$PhSO_2$-D-Phe-Pro-Arg-H.HCl

By methods substantially equivalent to those described in Example 51, 2.3 g of $PhSO_2$-D-Phe-Pro-Arg-H.HCl dihydrate was prepared using $PhSO_2Cl$ in place of $MeSO_2Cl$. Also, the tripeptide arginine lactam was reduced with LiAl(O-t-Bu)$_3$H at −23° C. rather than LAH at −78° C.

$^1$H NMR FAB-MS, m/e 543 (MH+)

Analysis Calc. for $C_{26}H_{34}N_6O_5S$.1.2HCl.2.1$H_2O$; C 50.01, H 6.39, N 13.46, Cl 6.81; Found; C 49.88, H 6.16, N 13.10, Cl 6.63.

EXAMPLE 58

Preparation of N-(2,4-difluorophenylsulfonyl)-D-phenylalanyl-L-Prolinyl-L-Arginine Aldehyde Hydrochloride

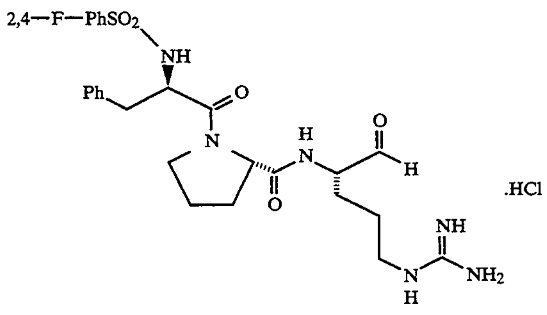

2,4-F-Ph$SO_2$-D-Phe-Pro-Arg-H.HCl

By methods substantially equivalent to those described in Example 51, 0.94 g of 2,4-difluorophenyl-$SO_2$-D-Phe-Pro-Arg-H.HCl hydrate was prepared using 2,4-difluorophenyl-$SO_2Cl$ in place of $MeSO_2Cl$. Also, the tripeptide arginine lactam was reduced with LiAl(O-t-Bu)$_3$H at −23° C. rather than LAH at −78° C. 2,4-F-Ph$SO_2$-D-Phe-Pro-Arg-H.HCl was purified by RPHPLC (95/5 (A/B), ramp to 70/30 (A/B), 240 min).

$^1$H NMR FAB-MS, m/e 579 (MH+)

Exact Mass Calc'd for $C_{26}H_{33}N_6O_5F_2S$, 579.220122; Found, 579.218900

Analysis Calculated for $C_{26}H_{32}N_6O_5F_2S$.1.5HCl.-$H_2O$ C 47.95 H 5.49 N 12.90 Found C 47.92 H 5.19 N 12.78

EXAMPLE 59

Preparation of N-(2,5-dimethoxyphenylsulfonyl)-D-phenylalanyl-L-Prolinyl-L-Arginine Aldehyde Hydrochloride

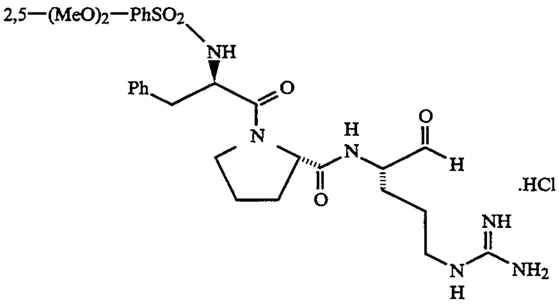

2,5-(MeO)$_2$-Ph$SO_2$-D-Phe-Pro-Arg-H.HCl

By methods substantially equivalent to those described in Example 51, 5 g of 2,5-dimethoxyphenyl-$SO_2$-D-Phe-Pro-Arg-H.HCl hydrate was prepared using 2,5-dimethoxyphenyl-$SO_2Cl$ in place of Me-$SO_2Cl$. Also, the tripeptide arginine lactam was reduced with LiAl(O-t-Bu)$_3$H at −23° C. rather than LAH at −78° C.

$^1$H NMR FAB-MS, m/e 603 (MH+)

Analysis Calc. for $C_{28}H_{38}N_6O_7S$.1.5HCl.$H_2O$; C 49.79, H 6.19, N 12.44; Found; C 50.32, H 6.17, N 12.05.

EXAMPLE 60

Preparation of N-(3,5-dimethyl-4-isoxazolylsulfonyl)-D-phenylalanyl-L-Prolinyl-L-Arginine Aldehyde Hydrochloride

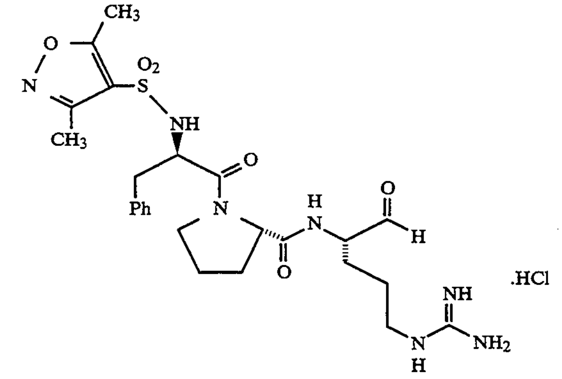

3,5-Me-4-isoxazolyl-$SO_2$-D-Phe-Pro-Arg-H.HCl

By methods substantially equivalent to those described in Example 51, 0.43 g of 3,5-dimethyl-4-isoxazolyl-$SO_2$-D-Phe-Pro-Arg-H.HCl hydrate was prepared using 3,5-dimethyl-4-isoxazolyl-$SO_2Cl$ in place of Me-$SO_2Cl$. 3,5-dimethyl-4-isoxazolyl-$SO_2$-D-Phe-Pro-Arg-H.HCl was purified by RPHPLC (98/2 (A/B), ramp to 65/35 (A/B), 240 min).

$^1$H NMR FAB-MS, m/e 562 (MH+)

Analysis Calc. for $C_{25}H_{35}N_7O_6S$.1.4HCl.$H_2O$; C 47.61, H 6.14, N 15.55; Found; C 47.97, H 5.91, N 15.22.

EXAMPLE 61

Preparation of N-(8-quinolinylsulfonyl)-D-phenylalanyl-L-Prolinyl-L-Arginine Aldehyde Hydrochloride

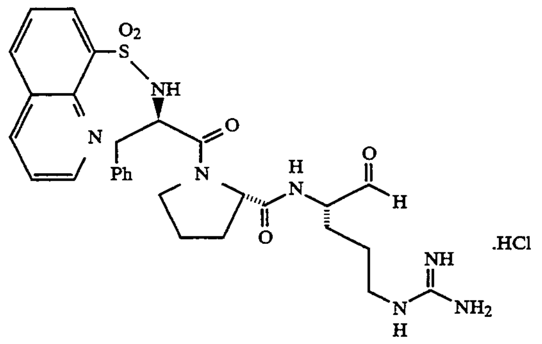

8-Quinolyl-$SO_2$-D-Phe-Pro-Arg-H.HCl

By methods substantially equivalent to those described in Example 51, 0.050 g of 8-quinolyl-$SO_2$-D-Phe-Pro-Arg-H.HCl was prepared using 8-quinolyl-$SO_2Cl$ in place of $MeSO_2Cl$. 8-quinolyl-$SO_2$-D-Phe-Pro-Arg-H.HCl was purified by RPHPLC (95/5 (A/B), ramp to 70/30 (A/B), 240 min).

$^1$H NMR FAB-MS, m/e 594 (MH+)

Exact Mass Calc'd for $C_{29}H_{36}N_7O_5S$, 594.2499; Found, 594.2505.

Analysis Calculated for $C_{29}H_{35}N_7O_5S$.4HCl.2$H_2O$; C 44.91 H 5.59 N 12.64 Found C 44.97 H 5.09 N 10.32

EXAMPLE 62

Preparation of N-(4-carboxyphenylsulfonyl)-D-phenylalanyl-L-Prolinyl-L-Arginine Aldehyde Hydrochloride

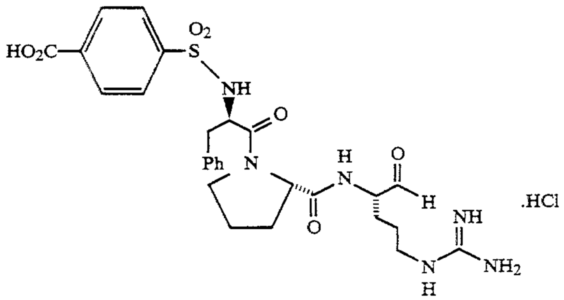

A) 4-($BzlO_2C$)-$C_6H_4SO_2Cl$

To a solution of p-chlorosulfonyl-benzoic acid (25 g, 113 mmol) in dichloromethane (500 mL) and dimethyl formamide (150 mL), was added oxalyl chloride (12.3 mL, 141 mmol). After stirring for 2 h, the solvents were removed in vacuo.

The residue was then mixed with benzyl alcohol (95 mL) at room temperature, which caused the development of heat. After the heat dissapated, the mixture was partitioned between water and ethyl acetate. The layers were separated and the aqueous phase was extracted twice with ethyl acetate. The combined organic phase was dried with $Na_2SO_4$, filtered and then concentrated to about ¼ original volume, then refrigerated over night. The next morning, the precipitate was filtered and dried to give 2.8 g (8%) of the desired product.

$^1H$ NMR FD-MS, m/e 310 ($M^+$)

B) Cbz-D-Phe-Pro-O-t-Bu

By a method substantially equivalent to that described in Example 45-A, 29 g (90%) of Cbz-D-Phe-Pro-O-t-Bu was prepared, using Cbz-D-Phe-OH in place of Boc-D-Phe-OH and HCl.Pro-O-t-Bu in place of HCl.Pro-OBzl.

$^1H$ NMR FD-MS, m/e 452 ($M^+$)

C) D-Phe-Pro-O-t-Bu

To a solution of Cbz-D-Phe-Pro-O-t-Bu (29 g, 64 mmol) in ethanol (500 mL) was added 5% Pd/C (14.5 g). The mixture was shaken on a hydrogenation apparatus for 16 h under 60 psi $H_2$. The solution was then filtered through a pad of Celite® and concentrated in vacuo to give 17.5 g (86%) of thick oil.

$^1H$ NMR FD-MS, m/e 319 ($MH^+$)

Analysis Calculated for $C_{18}H_{26}N_2O_3$; C 67.90, H 8.23, N 8.80; Found; C 67.66, H 8.19, N 8.67.

D) 4-(BzlO2C)-$C_6H_4SO_2$-D-Phe-Pro-O-t-Bu

By a method substantially equivalent to that described in Example 51-A, 11.3 g (50%) of 4-($BzlO_2C$)-$C_6H_4SO_2$-D-Phe-Pro-O-t-Bu was prepared, using 4-($BzlO_2C$)-$C_6H_4SO_2Cl$ in place of $MeSO_2Cl$ and D-Phe-Pro-O-t-Bu in place of TFA.D-Phe-Pro-OBzl.

FD-MS, m/e 592 ($M^+$)

E) 4-($BzlO_2C$)-$C_6H_4SO_2$-D-Phe-Pro-OH 4-($BzlO_2C$)-$C_6H_4SO_2$-D-Phe-Pro-O-t-Bu (11.3 g, 19 mmol) was dissolved in trifluoroacetic acid (100 mL) and anisole (5 mL). After stirring for 2 h, the solvent was removed by rotary evaporation. The residue was partitioned between diethyl ether (300 mL) and saturated aqueous $NaHCO_3$ (300 mL). The layers were separated and the aqueous phase was acidified to pH 2 with 5N HCl, then extracted three times with ethyl acetate (200 mL). The combined ethyl acetate extracts were dried ($MgSO_4$), filtered and concentrated in vacuo to give 6.5 g 64%) of a thick, light brown oil.

FD-MS, m/e 538 ($MH^+$)

F) 4-($HO_2C$)-$C_6H_4SO_2$-D-Phe-Pro-Arg-H.HCl

By methods substantially equivalent to those described in Example 45-H and 45-I, 0.8 g of 4-($HO_2C$)-$C_6H_4SO_2$-D-Phe-Pro-Arg-H.HCl hydrate was prepared. The tripeptide arginine lactam was reduced with $LiAl(O\text{-}t\text{-}Bu)_3H$ at −23° C. rather than LAH at −78° C. The product was contaminated with tripeptide arginine alcohol which could not be removed by RPHPLC.

$^1H$ NMR FAB-MS, m/e 587 ($MH^+$)

Analysis Calculated for $C_{27}H_{34}N_6O_7S.1.3HCl.H_2O$ C 49.73 H 5.77 N 12.89 Found C 49.60 H 5.76 N 12.93

EXAMPLE 63

Preparation of N-(2-thiazolylsulfonyl)-D-phenylalanyl-L-Prolinyl-L-Arginine Aldehyde Hydrochloride

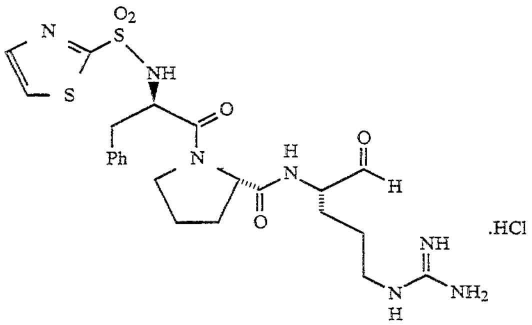

A) 2-Thiazolyl-$SO_2Cl$

To a solution of thiazole (10 g, 118 mmol) in tetrahydrofuran (600 mL) at −78° C. was slowly added a solution of n-butyl lithium, 1.6M in hexanes (73 mL, 118 mmol). After 1 h, $SO_2$(g) was bubled through the solution until an aliquot was acidic to moist pH paper. The cold bath was then removed and the solution was allowed to warm to room temperature. The solution was then poured into hexanes (1.5 L) and the resulting precipitate was filtered and dried to give 16.7 g of a light yellow solid.

The solid (10 g) was then suspended in dichloromethane (60 mL), cooled to 0° C., and treated with N-chlorosuccinimide (8.6 g, 64.5 mmol). After stirring for 2 h, the solution was filtered, and the filtrate was concentrated in vacuo to give 6.2 g of a yellow oil. The oil was then dissolved in diethyl ether, filtered and concentrated in vacuo to give 4.4 g (34%) of oil. FD-MS, m/e 183 ($M^+$)

B) 2-Thiazolyl-$SO_2$-D-Phe-Pro-Arg(Cbz)lactam

By methods substantially equivalent to those described in Example 51-A, 45-D, and 45-H, 7.7 g of 2-thiazolyl-$SO_2$-D-Phe-Pro-Arg(Cbz)lactam was prepared using 2-thiazolyl-$SO_2Cl$ in place of $MeSO_2Cl$.

$^1H$ NMR FD-MS, m/e 682 ($M^+$)

Analysis Calculated for $C_{31}H_{35}N_7O_7S$; C 54.61, H 5.17, N 14.38; Found; C 54.38, H 5.27, N 14.09.

C) 2-Thiazolyl-$SO_2$-D-Phe-Pro-Arg-H.HCl

2-Thiazolyl-$SO_2$-D-Phe-Pro-Arg(Cbz)lactam was reduced using LAH by a method substantially equivalent to that described in Example 45-I. The Cbz protecting group was then removed by treatment with liquid HF (10mL) and anisole (1.0 mL) in a Teflon®/Kel-F® apparatus at 0° C. for 1 hour to yield after evaporation of HF and precipitation with $Et_2O$ 1.1 g of crude 2-thiazolyl-$SO_2$-D-Phe-Pro-Arg-H.HF. The crude product was then purified by RPHPLC (98/2 (A/B), 40 min; ramp to 80/20 (A/B), 280 min) to yield 280 mg of pure 2-thiazolyl-$SO_2$-D-Phe-Pro-Arg-H.HCl.

$^1$H NMR FAB-MS, m/e 550 (MH+)

Analysis Calc. for $C_{23}H_{31}N_7O_5S_2.1.1HCl.H_2O$; C 45.45, H 5.65, N 16.13, Cl 6.42; Found; C 45.29, H 5.35, N 15.86, Cl 6.72.

EXAMPLE 64

Preparation of N-(ethylsulfonyl)-D-phenylglycinyl-L-Prolinyl-L-Arginine Aldehyde Hydrochloride

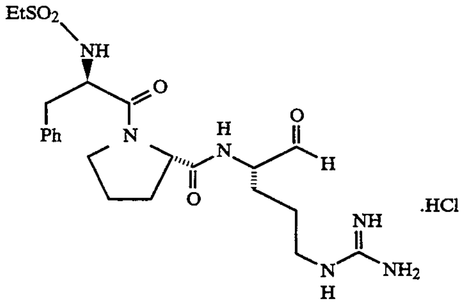

$EtSO_2$-D-Phg-Pro-Arg-H.HCl

By methods substantially equivalent to those described in Examples 45-A, 45-B, 51-A, 45-D, 45-H and 45-I, using Boc-D-Phg-OH in place of Boc-D-Phe-OH, $EtSO_2Cl$ in place of $MeSO_2Cl$, and $LiAl(O\text{-}t\text{-}Bu)_3H$ at −23° C. in place of LAH at −78° C., 450 mg of $EtSO_2$-D-Phg-Pro-Arg-H.HCl hydrate was prepared. $EtSO_2$-D-Phg-Pro-Arg-H.HCl was purified by RPHPLC (98/2 (A/B), ramp to 60/40 (A/B), 240 min).

$^1$H NMR FAB-MS, m/e 481 (MH+)

Analysis Calc. for $C_{21}H_{32}N_6O_5S.HCl.1.5H_2O$; C 46.36, H 6.67, N 15.45; Found; C 46.66, H 6.35, N 15.31.

EXAMPLE 65

Preparation of N-(ethylsulfonyl)-D-cyclohexylalanyl-L-Prolinyl-L-Arginine Aldehyde Hydrochloride

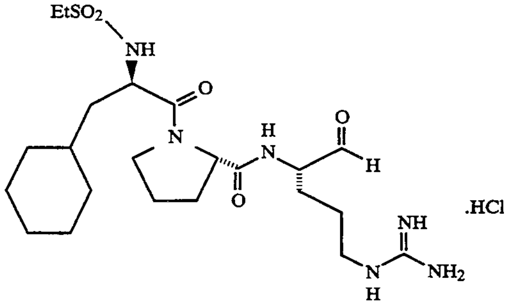

$EtSO_2$-D-Cha-Pro-Arg-H.HCl

By methods substantially equivalent to those described in Example 45-A, 45-B, 51-A, 45-D, 45-H and 45-I, using Boc-D-Cha-OH in place of Boc-D-Phe-OH, and $EtSO_2Cl$ in place of $MeSO_2Cl$, 1.3 g of $EtSO_2$-D-Cha-Pro-Arg-H.HCl was prepared. $EtSO_2$-D-Cha-Pro-Arg-H.HCl was purified by RPHPLC (98/2 (A/B), ramp to 60/40 (A/B), 240 min).

$^1$H NMR FAB-MS, m/e 501 (MH+)

Analysis Calculated for $C_{22}H_{40}N_6O_5S.1.8HCl$ C 46.66 H 7.44 N 14.84 Found C 47.05 H 7.05 N 14.65

EXAMPLE 66

Preparation of N-(ethylsulfonyl)-D-cyclohexylglycinyl-L-Prolinyl-L-Arginine Aldehyde Hydrochloride

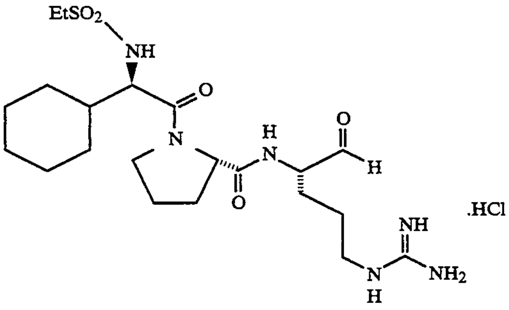

A) HCl.D-Chg-OMe

HCl (g) was bubbled through a suspension of D-Chg-OH.HCl (37.8 g, 240 mmol) in methanol (750 mL) for about 20 min. During this time, all of the solid went into solution. The solution was allowed to stir for 48 h, and then diethyl ether (1.5 L) was added. The resulting precipitate was filtered and dried to give 32.1 g (64%) of a light brown solid.

FD-MS, m/e 172 (MH+)

B) $EtSO_2$-D-Chg-OMe

By a method substantially equivalent to that described in Example 51-A, 14.2 g (75%) of $EtSO_2$-D-Chg-OMe was prepared from HCl.D-Chg-OMe, using $EtSO_2Cl$ in place of $MeSO_2Cl$.

$^1$H NMR FD-MS, m/e 263 (M+)

Analysis Calculated for $C_{11}H_{21}NO_4S$; C 50.17, H 8.04, N 5.32; Found; C 50.07, H 8.13, N 5.31.

C) $EtSO_2$-D-Chg-OH

By a method substantially equivalent to that described in Example 45-D, 12.5 g (94%) of $EtSO_2$-D-Chg-OH was prepared from $EtSO_2$-D-Chg-OMe.

$^1$H NMR FD-MS, m/e 250 (MH+)

Analysis Calculated for $C_{10}H_{19}NO_4S$; C 48.17, H 7.68, N 5.62; Found; C 48.40, H 7.93, N 5.23.

D) $EtSO_2$-D-Chg-Pro-Arg-H.HCl

By methods substantially equivalent to those described in Examples 45-A, 45-D, 45-H and 45-I, 0.25 g of $EtSO_2$-D-Chg-Pro-Arg-H.HCl hydrate was prepared using $EtSO_2$-D-Chg-OH in place of Boc-D-Phe-OH. $EtSO_2$-D-Chg-Pro-Arg-H.HCl hydrate was purified by RPHPLC (98/2 (A/B), 30 min; ramp to 75/25 (A/B), 270 min).

$^1$H NMR NAB-MS, m/e 487 (MH+)

Analysis Calculated For $C_{21}H_{38}N_6O_6S.1.5HCl.H_2O$ C 45.09 H 7.48 N 15.02 Found C 44.76 H 7.27 N 15.02

EXAMPLE 67

Preparation of N-(acetyl)-D-phenylalanyl-L-Prolinyl-L-Arginine Aldehyde Hydrochloride

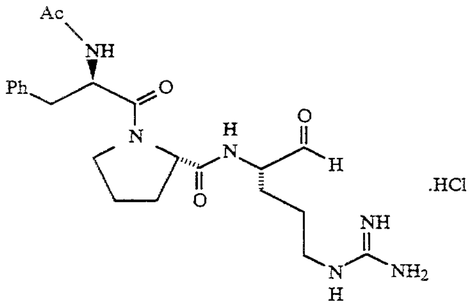

Ac-D-Phe-Pro-Arg-H.HCl

By methods substantially equivalent to those described in Example 51, using acetyl chloride in place of $MeSO_2Cl$, 210 mg of Ac-D-Phe-Pro-Arg-H.HCl dihydrate was prepared. Ac-D-Phe-Pro-Arg-H.HCl was purified by RPHPLC (95/5 (A/B), 80 min; ramp to 75/25 (A/B), 320 min; hold to 360 min).

$^1H$ NMR FAB-MS, m/e 445 ($MH^+$)

Analysis Calc. for $C_{22}H_{32}N_6O_4.2HCl.2H_2O$; C 47.74, H 6.92, N 15.18; Found; C 47.40, H 6.83, N 14.88.

EXAMPLE 68

Preparation of N-(methoxyacetyl)-D-phenylalanyl-L-Prolinyl-L-Arginine Aldehyde Hydrochloride

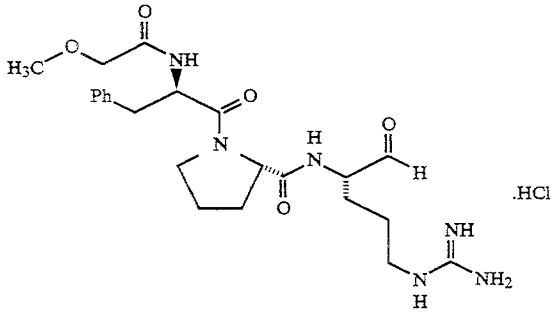

$CH_3OCH_2CO$-D-Phe-Pro-Arg-H.HCl

By methods substantially equivalent to those described in Example 51, using $CH_3OCH_2(CO)Cl$ in place of $MeSO_2Cl$, 110 mg of $CH_3OCH_2CO$-D-Phe-Pro-Arg-H.HCl was prepared. $CH_3OCH_2CO$-D-Phe-Pro-Arg-H.HCl was purified by RPHPLC (95/5 (A/B), 80 min; ramp to 75/25 (A/B), 320 min; hold to 360 min).

$^1H$ NMR FAB-MS, m/e 475 ($MH^+$)

Analysis Calc. for $C_{23}H_{34}N_6O_5.HCl$; C 54.06, H 6.90, N 16.44, Cl 6.94; Found; C 54.33, H 6.69, N 16.54, Cl 6.94.

EXAMPLE 69

Preparation of N-(trifluoroacetyl)-D-phenylalanyl-L-Prolinyl-L-Arginine Aldehyde Hydrochloride

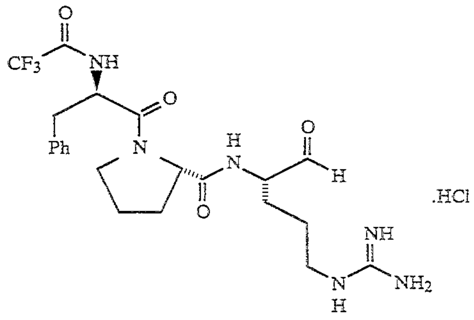

$CF_3CO$-D-Phe-Pro-Arg-H.HCl

By methods substantially equivalent to those described in Example 51, using trifluoroacetic anhydride in place of $MeSO_2Cl$, 3.6 mg of $CF_3CO$-D-Phe-Pro-Arg-H.HCl ethanolate was prepared.

$^1H$ NMR FAB-MS, m/e 499 ($MH^+$)

Analysis Calc. for $C_{22}H_{29}N_6O_4F_3.1.5HCl.H_2O.EtOH$; C 46.62, H 6.44, N 13.59; Found; C 46.32, H 6.19, N 13.70.

EXAMPLE 70

Preparation of N-(phenylacetyl)-D-phenylalanyl-L-Prolinyl-L-Arginine Aldehyde Hydrochloride

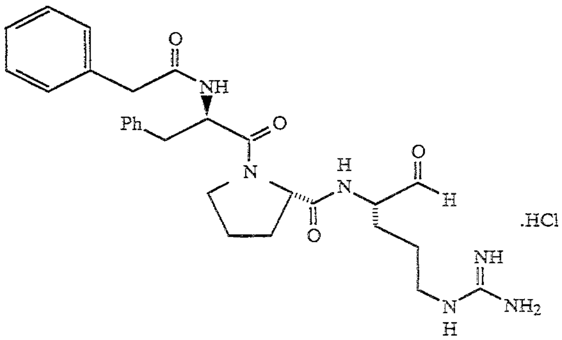

$PhCH_2CO$-D-Phe-Pro-Arg-H.HCl

By methods substantially equivalent to those described in Example 51, using phenylacetyl chloride in place of $MeSO_2Cl$, 3.5 g of $PhCH_2CO$-D-Phe-Pro-Arg-H.HCl was prepared.

$^1H$ NMR FAB-MS, m/e 521 ($MH^+$)

Analysis Calc. for $C_{28}H_{36}N_6O_4.1.2HCl.H_2O.0.5EtOH$; C 57.53, H 7.03, N 13.88; Found; C 57.63, H 6.66, N 13.52.

EXAMPLE 71

Preparation of N-(cylohexoyl)-D-phenylalanyl-L-Prolinyl-L-Arginine Aldehyde Hydrochloride

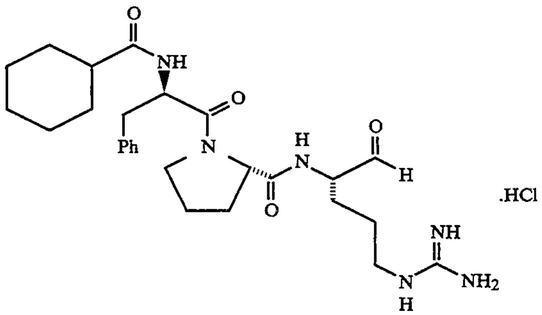

cyclohexyl-CO-D-Phe-Pro-Arg-H.HCl

By methods substantially equivalent to those described in Example 51, using cyclohexane carbonyl chloride in place of $MeSO_2Cl$, 5.3 g of cyclohexyl-CO-D-Phe-Pro-Arg-H.HCl was prepared.

$^1$H NMR FAB-MS, m/e 513 (MH+)

Analysis Calc. for $C_{27}H_{40}N_6O_4$.HCl; C 59.06, H 7.53, N 15.31; Found; C 59.00, H 7.34, N 15.07.

EXAMPLE 72

Preparation of N-(acetyl)-D-cyclohexylalanyl-L-Prolinyl-L-Arginine Aldehyde Hydrochloride

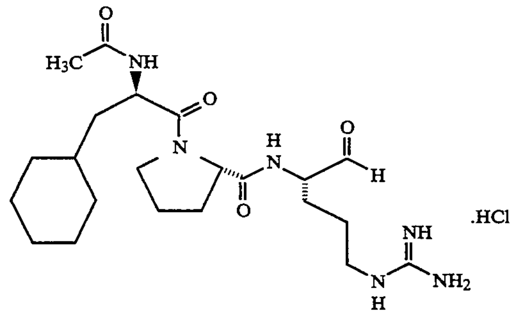

Ac-D-Cha-Pro-Arg-H.HCl

By methods substantially equivalent to those described in Examples 45-A, 45-B, 51-A, 45-D, 45-H and 45-I, using Boc-D-Cha-OH in place of Boc-D-Phe-OH, and using acetyl chloride in place of $MeSO_2Cl$, 0.62 g of Ac-D-Cha-Pro-Arg-H.HCl was prepared. Ac-D-Cha-Pro-Arg-H.HCl was purified by RPHPLC (95/5 (A/B) ramp to 70/30 (A/B), 240 min).

$^1$H NMR FAB-MS, m/e 451 (MH+)

Analysis Calc. for $C_{22}H_{38}N_6O_4$.2HCl.0.5$H_2O$; C 49.62, H 7.76, N 15.78; Found; C 49.63, H 7.61, N 15.81.

EXAMPLE 73

Preparation of N-(4-di-n-propylamino sulfonylbenzoyl)-D-phenylalanyl-L-Prolinyl-L-Arginine Aldehyde Hydrochloride

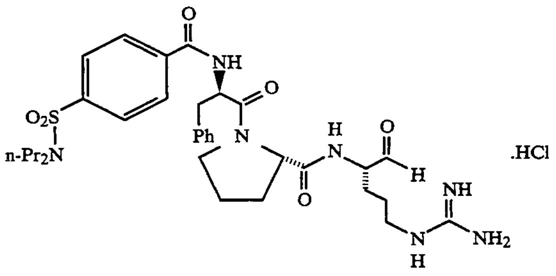

A) 4-(n-$Pr_2NSO_2$)-$C_6H_4$CO-D-Phe-Pro-OBzl

To a solution of 4-(n-Pr2$NSO_2$)-$C_6H_4$COOH (2.5 g, 8.8 mmol) in dichloromethane (100 mL) was added TFA.D-Phe-Pro-OBzl (4.1 g, 8.8 mmol), prepared substantially according to Example 1-B, N,N-diisopropylethylamine (8.0 mL, 44 mmol), and HOBT (1.2 g, 8.8 mmol), followed by 1-(3-dimethylaminopropyl)-3ethylcarbodiimide.HCl (1.9 g, 9.6 mmol). After stirring for 16 h, the solvents were removed in vacuo and the residue was dissolved in ethyl acetate. The organic solution was washed twice with 1N citric acid, twice with saturated aqueous $NaHCO_3$, twice with water and once with brine. The ethyl acetate was then removed in vacuo and the residue was chromatographed over silica gel, eluting with 1:1 ethyl acetate:hexanes. The product containing fractions as judged by TLC were combined and concentrated in vacuo to give 3.32 g (61%) of white foam.

$^1$H NMR FD-MS, m/e 619 (M+)

Analysis Calculated for $C_{34}H_{41}N_3O_6S$; C 65.89, H 6.67, N 6.78; Found; C 65.79, H 6.86, N 6.55.

B) 4-(n-Pr2$NSO_2$)-$C_6H_4$CO-D-Phe-Pro-Arg-H.HCl

By methods substantially equivalent to those described in Examples 45-D, 45-H and 45-I, 1.4 g of 4-(n-$Pr_2NSO_2$)-$C_6H_4$CO-D-Phe-Pro-Arg-H.HCl was prepared from 4-(n-$Pr_2NSO_2$)-$C_6H_4$CO-D-Phe-Pro-OBzl, using LiAl(O-t-Bu)$_3$H at −23° C. in place of LAH at −78° C. 4-(n-$Pr_2NSO_2$)-$C_6H_4$CO-D-Phe-Pro-Arg-H.HCl was purified by RPHPLC (95/5 (A/B) ramp to 60/40 (A/B), 240 min).

$^1$H NMR FAB-MS, m/e 670 (MH+)

Analysis Calc. for $C_{33}H_{47}N_7O_6S$.HCl; C 56.12, H 6.85, N 13.88, Cl 5.02; Found; C 56.40, H 6.81, N 13.78, Cl 5.06.

EXAMPLE 74

Preparation of N-(cyclohexylmethyl)-D-phenylalanyl-L-Prolinyl-L-Arginine Aldehyde Hydrochloride

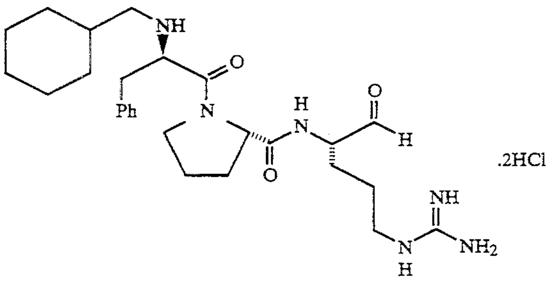

A) cyclohexyl-$CH_2$-D-Phe-Pro-O-t-Bu

To a solution of Cbz-D-Phe-Pro-O-t-Bu (11.2 g, 24.7 mmol) and cyclohexanecarboxaldehyde (4.4 mL, 37.6 mmol) in ethanol (135 mL) was added 5% Pd/C (2 g). The suspension was shaken under an atmosphere of $H_2$ (60 psi) overnight. The solution was then filtered and concentrated in vacuo. The residue was then dissolved in methanol, filtered through an acrodisc, and then concentrated in vacuo. The residue was then dissolved in diethyl ether, filtered and extracted three times with 1N citric acid. The combined aqueous acid phase was adjusted to pH 10 with 2N NaOH and extracted three times with chloroform. The combined chloroform extracts were dried over $Na_2SO_4$, filtered and concentrated in vacuo to give 6.5 g (64%) of clear oil.

$^1$H-NMR FD-MS, m/e 415 ($MH^+$)

B) Cbz-N-cyclohexyl-$CH_2$-D-Phe-Pro-OH

To a solution of cyclohexyl-$CH_2$-D-Phe-Pro-O-t-Bu (6.3 g, 15.2 mmol) in dichloromethane (100 mL) at 0° C. was added N,N-diisopropylethylamine (10.4 mL, 62.6 mmol). To this stirring solution was slowly added a solution of benzyl chloroformate (3.8 mL, 16.8 mmol) in dichloromethane (25 mL). After 1.5 h, chloroform (100 mL) was added and the solution was washed three times with 1N HCl and once with water. The organic phase was then dried over $Na_2SO_4$, filtered and concentrated in vacuo.

The residue was dissolved in a solution of anisole (5 mL) in trifluoroacetic acid (50 mL) at 0° C. and allowed to stir for 5 h. The solvents were then removed in vacuo and the residue was partitioned between diethyl ether and saturated aqueous $NaHCO_3$. The diethyl ether phase was again extracted three times with saturated aqueous $NaHCO_3$ and three times with water. The combined aqueous extracts were acidified to pH 2 with 1N HCl and extracted three times with chloroform. The combined chloroform extracts were dried ($Na_2SO_4$), filtered and concentrated in vacuo to give 6.3 g (84%) of a pale yellow foam.

$^1$H NMR FD-MS, m/e 493 ($MH^+$)

Analysis Calculated for $C_{29}H_{36}N_2O_5.0.15\ CHCl_3$; C 68.58, H 7.14, N 5.48; Found; C 68.36, H 7.21, N 5.30.

C) cyclohexyl-$CH_2$-D-Phe-Pro-Arg-H.HCl

By methods substantially equivalent to those described in Examples 45-H and 45-I, 3.4 g of cyclohexyl-$CH_2$-D-Phe-Pro-Arg-H.HCl dihydrate was prepared from Cbz-N-cyclohexyl-$CH_2$-D-Phe-Pro-OH.

FAB-MS, m/e 499 ($MH^+$)

Analysis Calc. for $C_{27}H_{42}N_6O_3.2.5HCl.2H_2O$; C 51.82, H 7.81, N 13.43; Found; C 51.94, H 7.50, N 13.25.

EXAMPLE 75

Preparation of N-methyl-D-cyclohexylalanyl-L-Prolinyl-L-Arginine Aldehyde Hydrochloride

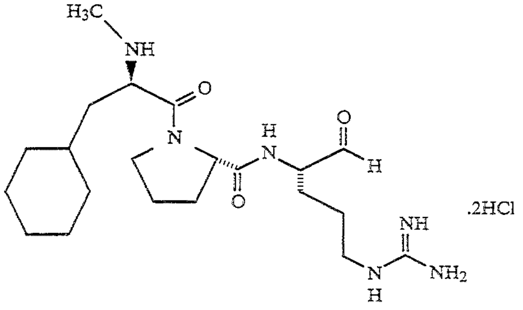

A) Cbz-D-Cha-Pro-OH

By a method substantially equivalent to that described in Example 62-E, 16.6 g (86%) of Cbz-D-Cha-Pro-OH was prepared from Cbz-D-Cha-Pro-O-t-Bu.

FD-MS, m/e 403 ($MH^+$)

Analysis Calculated for $C_{22}H_{30}N_2O_5$; C 65.65, H 7.51, N 6.96; Found; C 66.10, H 7.44, N 7.55.

B) Cbz-N-Me-D-Cha-Pro-OH

To a suspension of KH (19.3 g, 25% suspension in oil, 120 mmol) in tetrahydrofuran (100 mL) at 0° C. was slowly added (over 25 min) a solution of Cbz-D-Cha-Pro-OH (16.8 g, 41.7 mmol) in tetrahydrofuran (50 mL). During this addition period the internal temperature was monitored and maintained at less than 10° C. To this solution was then slowly added a solution of methyl iodide (5 mL, 80 mmol) and 18-crown-6 (661 mg, 2.5 mmol), again maintaining the internal temperature below 10° C. After 2 h acetic acid (10 mL) was added dropwise, followed by water (10 mL). The solution was then poured into cold water and the pH was adjusted to 9 with 2N NaOH. The aqueous base was washed twice with diethyl ether and then acidified to pH 2 with conc. HCl and extracted four times with chloroform. The chloroform extracts were combined, dried over $Na_2SO_4$, filtered and concentrated in vacuo to afford 15.7 g (90%) of a pale yellow solid.

$^1$H-NMR FD-MS, m/e 417 ($MH^+$)

Analysis Calculated for $C_{23}H_{32}N_2O_5$; C 66.33, H 7.74, N 6.73; Found; C 66.49, H 7.86, N 6.67.

C) Me-D-Cha-Pro-Arg-H.HCl

By methods substantially equivalent to those described in Examples 45-H and 45-I, using LiAl(O-t-Bu)3H at −23° C. in place of LAH at −78° C., 2.2 g of Me-D-Cha-Pro-Arg-H.HCl dihydrate was prepared from Cbz-N-Me-D-Cha-Pro-OH.

$^1$H NMR FAB-MS, m/e 423 ($MH^+$)

Analysis Calc. for $C_{21}H_{38}N_6O_3.2HCl.2H_2O$; C 47.45, H 8.34, N 15.81, Cl 13.34; Found; C 47.07, H 7.95, N 15.61, Cl 13.77.

EXAMPLE 76

Preparation of
N-(ethylaminocarbonyl)-D-phenylalanyl-L-Prolinyl-L-Arginine Aldehyde Hydrochloride

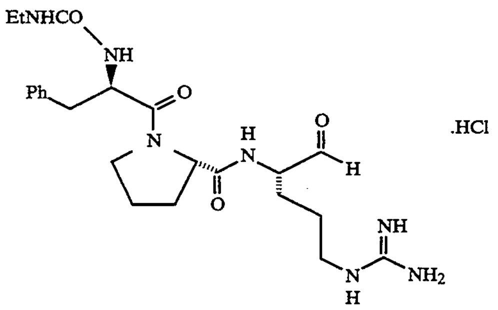

A) EtNHCO-D-Phe-Pro-OBzl

To a solution of TFA.D-Phe-Pro-OBzl (10 g, 21.4 mmol) in dichloromethane (150 mL) was added N,N-diisopropylethylamine (3.73 mL, 21.4 mmol) followed by ethyl isocyanate (1.86 mL, 23.5 mmol). After stirring for 16 h, the solution was washed three times with 1N HCl, dried over $Na_2SO_4$, filtered and concentrated in vacuo to give 9.7 g (107%) of white foam.

FD-MS, m/e 424 (MH+)

B) EtNHCO-D-Phe-Pro-Arg-H.HCl

By methods substantially equivalent to those described in Example 45-D, 45-H and 45-I, 1.2 g of EtNHCO-D-Phe-Pro-Arg-H.HCl hydrate was prepared from EtNHCO-D-Phe-Pro-OBzl.

FAB-MS, m/e 474 (MH+)

Analysis Calc. for $C_{23}H_{35}N_7O_4$.2.1HCl.$H_2O$; C 48.62, H 6.94, N 17.26; Found; C 48.79, H 6.88, N 16.90.

EXAMPLE 77

Preparation of
N-(ethoxycarbonyl)-D-phenylalanyl-L-Prolinyl-L-Arginine Aldehyde Hydrochloride

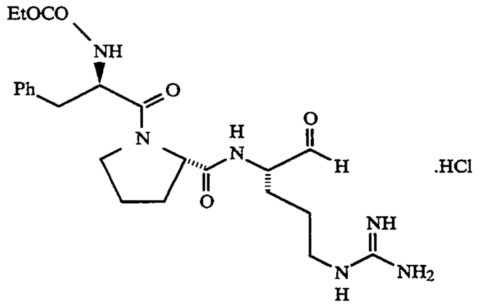

EtOCO-D-Phe-Pro-Arg-H.HCl

By methods substantially equivalent to those described in Example 51, using ethyl chloroformate in place of $MeSO_2Cl$, 2.5 g of EtOCO-D-Phe-Pro-Arg-H.HCl was prepared.

$^1$H NMR FAB-MS, m/e 475 (MH+)

Analysis Calc. for $C_{23}H_{34}N_6O_5$.1.7HCl.$H_2O$.0-.6EtOH; C 49.93, H 7.15, N 14.43; Found; C 50.04, H 6.76, N 14.14.

EXAMPLE 78

Preparation of
N-(ethoxycarbonyl)-D-cyclohexylalanyl-L-prolinyl-L-Arginine Aldehyde Hydrochloride

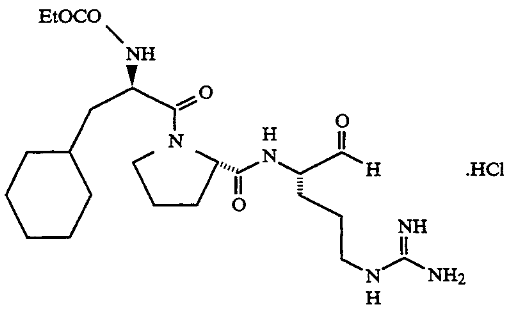

EtOCO-D-Cha-Pro-Arg-H.HCl

By methods substantially equivalent to those described in Examples 45-A, 45-B, 51-A, 45-D, 45-H and 45-I, using ethyl chloroformate in place of $MeSO_2Cl$ and using Boc-D-Cha-OH in place of Boc-D-Phe-OH, 0.6 g of EtOCO-D-Cha-Pro-Arg-H.HCl hydrate was prepared. EtOCO-D-Cha-Pro-Arg-H.HCl was purified by RPHPLC (95/5 (A/B) ramp to 60/40 (A/B), 240 min).

$^1$H NMR FAB-MS, m/e 481 (MH+)

Analysis Calc. for $C_{23}H_{40}N_6O_5$.2.8HCl.$H_2O$; C 45.99 H 7.52 N 13.99 Found; C 45.86 H 7.15 N 13.70

EXAMPLE 79

Preparation of
N-methyl-D-phenylglycinyl-L-prolinyl-NH-CH[$(CH_2)_3$NH-C(NH)-$NH_2$]-C(OH)$SO_3$ Na.$H_2SO_4$ A) N-methyl-D-Phg-Pro-Arg-H-$H_2SO_4$.

By substantially following the procedures described above (and in EP 0 479 489 (Example 6)) the compound N-methyl-D-Phg-Pro-Arg-H.$H_2SO_4$ was prepared.

B) N-Methyl-D-Phg-Pro-NH-CH[($CH_2$ )$_3$NH-C(NH)-$NH_2$]-C(OH)$SO_3$Na.$H_2SO_4$.

N-methyl-D-Phg-Pro-Arg-H.$H_2SO_4$ (218 rag, 43 mmole) was dissolved in water (5 ml) and sodium bisulfite (44.7 mg, 43 mmole) was added to the solution. The reaction was lyophilized to give pure title compund (251 mg, 100%): FAB-MS 485 ($MH_2$+)

Analysis Calc. for $C_{20}H_{31}N_6O_6$SNaH.$H_2SO_4$ C 37.49 H 5.82 N 13.11 Found: C 37.38 H 5.64 N 12.47

EXAMPLE 80

Preparation of
D-1,2,3,4,4a,6,7,8,8a-Perhydroisoquinolin-3-yl carbonyl-L-prolinyl-L-arginine aldehyde bisulfite sulfate

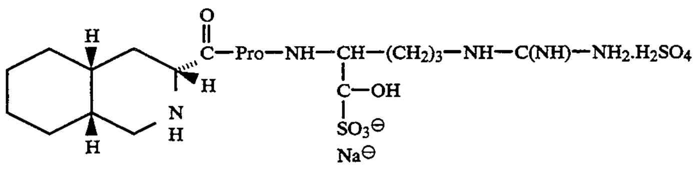

A) D-1,2,3,4-Tetrahydro-3-isoquinolinecarboxylic acid (1).

D-Phe (50 g, 302 mmol) was reated with 37% solution of formaldehyde (120 mL) and conc. HCl (380 mL) at reflux temperature. After 30 min. of reflux an additional 50 mL of formaldehyde was added and reaction refluxed for 3 hours. The reaction cooled to $-10°$ C. and the precipitate filtered. The solid was dried in vacuo to give the title compound (24.2 g, 45%) FD-MS 178 ($MH^+$).

B) D-1,2,3,4,4a,6,7,8,8a-Perhydro-3-isoquinolinecarboxylic acid (2).

A solution of D-1,2,3,4-tetrahydro-3-isoquinolinecarboxylic acid (1) (17 G, 96 mmol) in water (200 mL) and 20 ml of 5N HCl was reacted with 5% $Rh/Al_2O_3$ (8.5 g) at 2000 psi in a high pressure apparatus at 120° C. for 16 hours. The reaction mixture was filtered through a Celite pad, and the filtrate was freeze dried to give the title compound (21 g, 100%) FD-MS 184 ($MH^+$).

C) Cbz-D-1,2,3,4,4a,6,7,8,8a-Perhydro-3-isoquinolinecarboxylic acid (3).

D-3-Piq (2) (21.0 g, 95.8 mmol) was dissolved in tetrahydrofuran (75 mL) and water (50 mL). The pH of the solution was adjusted to 10.0 with 5N NaOH and benzyl chloroformate (16.4 mL, 115 mmol) was added dropwise and the pH maintained at 9.5 with 2N NaOH. The reaction was stirred for an additional 1 hour at room temperature. The organic solvent was evaporated in vacuo, diethylether (100 mL) and water (50 mL) was added to the residue. The aqueous layer separated, the pH of the solution was adjusted to 3.0 with 3N HCl and ethyl acetate (250 mL) was added. The organic layer was separated and dried ($MgSO_4$) the filtrate was concentrated in vacuo to give a clear oil of the title compound (25.8 g, 85%) FD-MS 318 ($MH^+$); $[a]_D = -5.1°$ (C=0.5 MeOH).

D) Cbz-D-1,2,3,4,4a,6,7,8,8a-Perhydro-3-isoquinolinecarboxy-L-Prolinyl-t-butylester (4).

Cbz-D-3-Piq (3) (17.2 g, 54 mmol) was dissolved in DMF (50 mL) and cooled to 0° C. To the reaction was added Proline-t-butylester (9.2 g, 54 mmol), 1-hydroxybenzo-triazole (7.3 g, 54 mmol), and DCC (11.1 g, 54 mmol). The reaction was stirred for 3 hours at 0° C. and 24 hours at room temperature. The reaction precipitate was filtered and the filtrate concentrated in vacuo to an oil. The oil was dissolved in EtOAc (200 mL) and water (100 mL). The organic layer was separated, washed with 1N $NaHCO_3$, water, 1.5N citric acid, and water. The organic layer was dried ($MgSO_4$), and the filtrate evaporated to an oil which was dried to give the title compound (23.8 g, 94%) FAB-MS 471 ($MH^+$); TLC $R_f$(A) 0.73; $[a]_D = -40.0°$ (C=0.5 MeOH)

E) Cbz-D-1,2,3,4,4a,6,7,8,8a-Perhydro-3-isoquinolinecarboxyl-L-Proline (5).

Cbz-D-3-Piq-Pro-O-t-Bu (4) (31.2 g, 66.3 mmole) was placed in a round bottom flask containing trifluoroacetic acid (100 ml), anisole (5 ml), and stirred at room temperature (1 hour). The reaction was concentrated in vacuo without heating, diethylether (150 ml), and water (100 mL) was added. The pH of the solution was adjusted to 9.8 with 5N NaOH. The aqueous layer separated, the pH of the solution was adjusted to 2.8 with 3N HCl and ethyl acetate (200 mL) was added. The organic layer was separated and dried (MgSO4) the filtrate was concentrated in vacuo to give a clear oil. The oil was dissolved in diethylether (300 mL) and the solution was allowed to stand at room temperature (24 h). The resulting solid was filtered washed with diethylether, and dried to give the title compound (13.5 g, 49%)

FAB-MS 415 ($MH^+$); $[a]_D = -57°$ (C=0.5 MeOH);

Analysis Calc. $C_{23}H_{30}N_2O_5$: C 66.65 H 7.29 N 6.76 Found: C 66.90 H 7.33 N 6.81

F) D-3-(cis)Piq-Pro-Arg-H.$H_2SO_4$

By substantially following the procedures described in Example 1, steps C, D, E, F, G and H, except using sulfuric acid rather than hydrochloric acid, the title compound was prepared. FAB-MS 421 ($MH^+$);

$[a]_D = -41°$ C.=0.5/0.01N $H_2SO_4$;

Analysis Calc. $C_{21}H_{36}N_6O_3.H_2SO_4.3H_2O$ C 44.04 H 7.74 N 14.68 Found: C 44.25 H 7.12 N 14.46

G) D-cis (4aS, 8aS)-3Piq-Pro-NH-CH[$(CH_2)_3$NH-C(NH)-$NH_2$]C(OH)$SO_3$Na.$H_2SO_4$ R-cis (4aS, 8aS)-3Piq-Pro-Arg-H.$H_2SO_4$ (204 mg, 30 mole) was dissolved in water (5 ml) and sodium bisulfite (40.5 mg, 39 mmole) was added to the solution. The reaction was lyophilized to give pure title compound (227 mg, 100%): FAB-MS 503 ($MH_2^+$);

Analysis Calc. $C_{21}H_{37}N_6O_6SNa.H_2SO_4.2H_2O$: C 38.44 H 6.30 N 12.81 Found: C 38.52 H 6.09 N 12.00

EXAMPLE 81

Preparation of N-methyl-D-phenylalanyl-L-prolinyl-L-NH-CH[$(CH_2)_3$NH-C(NH)-$NH_2$]-C(OH)$SO_3$Na.$H_2SO_4$ A) N-methyl-D-Phe-Pro-Arg-H.$H_2SO_4$ By substantially following the procedures described above and in U.S. Pat. No. 4,703,036 (Example 1) the compound N-methyl-D-Phe-Pro-Arg-H.$H_2SO_4$ is prepared.

B) N-methyl-D-Phe-L-Pro-L-NH-CH[$(CH_2)_3$NH-C(NH)-$NH_2$]-C(OH)$SO_3$Na.$H_2SO_4$ By substantially following the procedures described in Example 79, Step B, the title compound is prepared.

EXAMPLE 82

Preparation of D-1,2,3,4,4a,6,7,8,8a-Perhydroisoquinolin-1-ylcarbonyl-L-prolinyl-L-NH-CH[$(CH_2)_3$NH-C(NH)-$NH_2$]-C(OH)$SO_3$Na.$H_2SO_4$

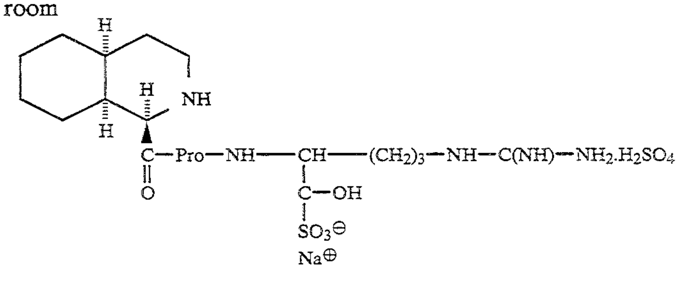

By substantially following the procedures described in Example 80, the title compound is prepared.

EXAMPLE 83

Preparation of D-1,2,3,4-Tetrahydroisoquinolin-1-ylcarbonyl-L-prolinyl-L-arginine aldehyde bisulfite sulfate A) D-1-Tiq-L-Pro-L-Arg-H.$H_2SO_4$ By substantially following the procedures described above, and in EP 0 479 489 A2 (Example 27), the compound D-1-Tiq-L-Pro-L-Arg-H.$H_2SO_4$ is prepared.

B) D-1-Tiq-L-Pro-L-NH-CH[$(CH_2)_3$-NH-C(NH)-$NH_2$]-C(OH)$SO_3$Na.$H_2SO_4$

By substantially following the procedures described in Example 80, Step G, the title compound is prepared.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (tPA), modified tPA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g.

physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art, In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

FORMULATION 1

Hard gelatin capsules are prepared using the following ingredients:

| | Quantity (mg/capsule) |
|---|---|
| Active ingredient | 250 |
| Starch, dried | 200 |
| Magnesium stearate | 10 |

-continued

| | Quantity (mg/capsule) |
|---|---|
| Total | 460 mg |

FORMULATION 2

A tablet is prepared using the ingredients below:

| | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

FORMULATION 3

An aerosol solution is prepared containing the following components:

| | Weight |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to $-30^\circ$ C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-Phe-Val-Arg-p-nitroanilide.

The assay is carried out by mixing 50 μl buffer (0.03M Tris, 0.15M NaCl, pH 7.4) with 25 μl of human thrombin solution (purified human thrombin, Enzyme Research Laboratories, South Bend, Ind., at 8 NIH units/ml) and 25 μl of test compound in a solvent (50% aqueous methanol (v:v)). Then 150 μl of an aqueous solution of the chromogenic substate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I) .

$$\text{Thrombin} + I \rightleftharpoons \text{Thrombin} - I$$

$$Kass = \frac{[\text{Thrombin} - I]}{[(\text{Thrombin}) \times (I)]}$$

Kass is calculated for a range of concentrations of test compounds and the mean value reported in units of liter per mole.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952 incorporated by reference herein in its entirety. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from KabiVitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchaed from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by formula Ia or I.

TABLE 1

| | Serine Protease Inhibition Kass (L/mol × $10^6$) | | | | |
|---|---|---|---|---|---|
| Example No. | Human Thrombin | Xa | Trypsin | Plasmin | t-PA |
| 1 | 46. | | | | 0.02 |
| 2 | 12 | | | | |
| 3 | 45 | | | | |
| 4 | 5 | | | | |
| 5 | 4 | | | | |
| 6 | 21 | | | | |
| 8 | 595 | | | | |
| 9 | 121 | | | | |
| 10 | 27 | | | | |
| 11 | | | | | |
| 12 | 25 | | | | |
| 13 | | | | | |
| 14 | 37 | | | | |
| 15 | 70 | | | | |
| 16 | 85 | | | | |
| 17 | 12 | | | | |
| 18 | 1 | | | | |
| 19 | 2 | | | | |
| 20 | 11 | | | | |
| 21 | 18.4 | | | | |
| 22 | 39 | | | | |
| 23 | 79. | 0.06 | 29. | 0.55 | 0.02 |
| 24 | 12. | 0.13 | 14. | 0.31 | 0.0034 |
| 25 | 350. | 0.27 | 43. | 0.77 | 0.0045 |
| 26 | 75. | 0.12 | 17. | 0.17 | 0.0028 |
| 27 | 75. | 0.044 | 2.4 | 0.059 | 0.00079 |
| 28 | 24. | 0.11 | 20. | 0.31 | 0.051 |
| 29 | 5.0 | 0.025 | 1.7 | 0.020 | 0.00072 |
| 30 | 25. | 0.013 | 1.3 | 0.0083 | 0.0022 |
| 31 | 3.2 | 0.036 | 0.42 | 0.010 | 0.00034 |
| 32 | 5.7 | 0.024 | 0.45 | 0.0071 | 0.0011 |
| 33 | 0.6 | 0.027 | 1.7 | 0.056 | 0.007 |
| 34 | 2.8 | 0.002 | 0.18 | 0.001 | 0.009 |
| 35 | 57. | 0.036 | 4.9 | 0.12 | 0.002 |
| 36 | 6.5 | 0.078 | 4.7 | 0.058 | 0.001 |
| 37 | 47. | 0.030 | 4.9 | 0.12 | <0.001 |
| 38 | 38. | 0.077 | 7.3 | 0.074 | <0.001 |
| 39 | 66. | 0.095 | 21. | 0.066 | <0.001 |
| 40 | 47. | 0.088 | 15. | 0.13 | 0.001 |
| 41 | 430. | 0.49 | 42. | 1.2 | 0.023 |
| 42 | 24. | 0.22 | 38. | 0.24 | 0.010 |
| 43 | 31. | 0.23 | 28. | 0.56 | 0.027 |
| 44 | 2.1 | 0.033 | 1.4 | 0.031 | 0.0023 |
| 45 | 850. | 0.51 | 120. | 7.9 | 31. |
| 46 | 110. | 0.16 | 22. | 0.55 | 0.32 |
| 47 | 58. | 0.080 | 12. | 0.41 | 0.17 |
| 48 | 13. | 0.067 | 5.2 | 0.27 | 0.22 |
| 49 | 320. | 4.6 | 7.9 | 25. | 1.1 |
| 50 | 200. | 0.83 | 2.5 | 2.5 | 0.088 |
| 51 | 690. | 2.4 | 220. | 17. | 13. |

TABLE 1-continued

| | Serine Protease Inhibition Kass (L/mol × $10^6$) | | | | |
|---|---|---|---|---|---|
| Example No. | Human Thrombin | Xa | Trypsin | Plasmin | t-PA |
| 52 | 450. | 2.6 | 260. | 31. | 2.9 |
| 53 | 1,700. | 13. | 480. | 29. | 2.8 |
| 54 | 470. | 8.3 | 230. | 27. | 0.83 |
| 55 | 460. | 6.0 | 260. | 25. | 3.5 |
| 56 | 300. | 3.9 | 160. | 21. | (100% inhib. at 13 μg/mL) |
| 57 | 270. | 3.6 | 180. | 19. | 2.3 |
| 58 | 230. | 11. | 160. | 25. | 2.4 |
| 59 | 200. | 8.8 | 150. | 9.5 | 1.5 |
| 60 | 260. | 11. | 200. | 18. | 2.7 |
| 61 | | | | | N.T. |
| 62 | 70. | 2.0 | 43. | 7.0 | 1.1 |
| 63 | 68. | 2.8 | 52. | 3.4 | 0.31 |
| 64 | 510. | 45. | 160. | 14. | 0.34 |
| 65 | 550. | 20. | 200. | 45. | 0.73 |
| 66 | 260. | 24. | 260. | 13. | 0.11 |
| 67 | 3.4 | 0.066 | 14. | 0.28 | 0.11 |
| 68 | 33. | 0.29 | 57. | 3.8 | 0.30 |
| 69 | 26. | 0.033 | 15. | 0.31 | 0.17 |
| 70 | 29. | 0.10 | 14. | 0.54 | 0.37 |
| 71 | 20. | 0.064 | 5.9 | 0.24 | 0.26 |
| 72 | 26. | 1.1 | 12. | 0.61 | 0.035 |
| 73 | 43. | 0.32 | 15. | 0.86 | 0.62 |
| 74 | 480. | 0.11 | 69. | 0.49 | 0.046 |
| 75 | 590. | 5.6 | 160. | 7.7 | 0.37 |
| 76 | 25. | 0.21 | 60. | 2.0 | 0.54 |
| 77 | 170. | 2.3 | 240. | 16. | 2.5 |
| 78 | 360. | 8.1 | 140. | 26. | 0.75 |
| 79 (Step A) | 236 | | 87 | 1.3 | 0.01 |
| 79 | 239 | | 84 | 1.8 | 0.01 |
| 80 (Step F) | 56 | | 183 | 1.6 | 0.5 |
| 80 | 62 | | 137 | 2.7 | 0.01 |

N.T. = Not Tested

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *BioChem, J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 ul thrombin (73 NIH unit/ml) to 100 ul human plasma which contains 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of IC50 values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry,* 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research,* 50, 163–174 (1988). A CoAScreener coagulation instrument (American LABor, Inc.) is used for all coagulation assay measurements. The prothrombin time (PT) is measured by adding 0.05 ml saline and 0.05 ml Thromboplastin-C reagent to 0.05 ml test plasma. The activated partial thromboplastin time (APTT) is measured by incubation of 0.05 ml test plasma with 0.05 ml Actin reagent for 120 seconds followed by 0.05 ml CaCl2 (0.02M). The thrombin time (TT) is measured by adding 0.05 ml saline and 0.05 ml thrombin (10 NIH units/ml) to 0.05 ml test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

TABLE 2

| | Human Plasma Anticoagulation 2 × Clotting time (ng/mL) | | |
|---|---|---|---|
| Example No. | TT | APTT | PT |
| 23 | 59 | 1,800 | 1,980 |
| 24 | 160 | 2,100 | 3,600 |
| 25 | 28 | 960 | 1,400 |
| 26 | 42 | 1,400 | 1,100 |
| 27 | 48 | 2,500 | 2,200 |
| 28 | 100 | 1,600 | 2,400 |
| 29 | 190 | 5,400 | 6,100 |
| 30 | 220 | 2,800 | 4,200 |
| 31 | 300 | 12,000 | 11,000 |
| 32 | 1,000 | 11,000 | 9,200 |
| 33 | 300 | 5,400 | 7,300 |
| 34 | 1,800 | 21,000 | 37,000 |
| 35 | 93 | 3,200 | 3,300 |
| 36 | 310 | 5,000 | 7,100 |
| 37 | 71 | 4,100 | 2,800 |
| 38 | 98 | 2,700 | 2,200 |
| 39 | 160 | 3,400 | 3,000 |
| 40 | 91 | 3,100 | 2,400 |
| 41 | 52 | 1,200 | 2,100 |
| 42 | 120 | 3,000 | 2,800 |
| 43 | 41 | 1,500 | 1,600 |
| 44 | 560 | 12,000 | 11,000 |
| 45 | 43 | 440 | 870 |
| 46 | 35 | 1,100 | 1,400 |
| 47 | 47 | 1,300 | 1,700 |
| 48 | 150 | 2,300 | 3,400 |
| 49 | 110 | 1,000 | 2,500 |
| 50 | 97 | 1,400 | 2,700 |
| 51 | 21 | 330 | 530 |
| 52 | 9 | 260 | 660 |
| 53 | 6 | 220 | 510 |
| 54 | 18 | 300 | 700 |
| 55 | 13 | 270 | 510 |
| 56 | 46 | 360 | 480 |
| 57 | 14 | 450 | 930 |
| 58 | 21 | 350 | 940 |
| 59 | 92 | 550 | 2,000 |
| 60 | 33 | 430 | 1,300 |
| 61 | N.T. | N.T. | N.T. |
| 62 | 120 | 1,200 | 3,000 |
| 63 | 66 | 810 | 2,900 |
| 64 | 34 | 250 | 880 |
| 65 | 25 | 260 | 730 |
| 66 | 46 | 330 | 1,100 |
| 67 | 140 | 2,700 | 4,100 |
| 68 | 38 | 440 | 1,200 |
| 69 | 59 | 1,300 | 1,800 |
| 70 | 64 | 1,100 | 2,000 |
| 71 | 63 | 1,300 | 1,800 |
| 72 | 92 | 1,900 | 3,500 |
| 73 | 150 | 3,500 | 4,800 |
| 74 | 16 | 860 | 1,200 |
| 75 | 18 | 420 | 720 |
| 76 | 63 | 1,100 | 1,700 |
| 77 | 22 | 390 | 2,000 |
| 78 | 48 | 410 | 890 |

N.T. = Not Tested.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol,* 77:29,1982).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.,* 60:269,1990).

Spontaneous thrombolysis model

In vitro data suggests that peptide thrombin inhibitors inhibit thrombin and at higher concentrations may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}I$ human fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.,* 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika) are incubated for 5 minutes (37° C.) and $CaCl_2$ (0.1 ml, 0.025M) is added to start coagulation. Assays are done in duplicate and averaged.

Index of Bioavailability

A measure of bioactivity, plasma thrombin time (TT), serves as a substitute for the assay of parent compound on the assumption that increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\ po}{AUC\ iv} \times \frac{\text{Dose } iv}{\text{Dose } po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 ml/kg for i.v., and 5 ml/kg for p.o. and infusion volume is 3 ml/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

TABLE 3

Index of Bioavailability

| Example | Percent Relative Activity |
|---|---|
| 1 | 38% |
| 2 | 36% |
| 3 | 32% |
| 4 | 16% |
| 5 | |
| 6 | |
| 8 | 43% |
| 9 | 19% |
| 10 | 5% |
| 11 | |
| 12 | 16% |
| 13 | |
| 14 | |
| 15 | 28 |
| 16 | 19 |
| 17 | 8 |
| 22 | 15 |
| 45 | 2 |
| 46 | 1 |
| 47 | 3 |
| 48 | N.T.[a] |
| 49 | N.T. |

TABLE 3-continued

| Index of Bioavailability | |
|---|---|
| Example | Percent Relative Activity |
| 50 | N.T. |
| 51 | 27 |
| 52 | 31 |
| 53 | 14 |
| 54 | 18 |
| 55 | 10 |
| 56 | 26 |
| 57 | 3 |
| 58 | 6 |
| 59 | N.T. |
| 60 | N.T. |
| 61 | N.T. |
| 62 | 13 |
| 63 | N.T. |
| 64 | N.T. |
| 65 | 19 |
| 66 | N.T. |
| 67 | N.T. |
| 68 | N.T. |
| 69 | N.T. |
| 70 | N.T. |
| 71 | N.T. |
| 72 | 9 |
| 73 | N.T. |
| 74 | 1 |
| 75 | 13 |
| 76 | N.T. |
| 77 | 14 |
| 78 | N.T. |
| 79 (Step A) | 18 |
| 79 | 21 |
| 80 (Step F) | 46 |
| 80 | 57 |

N.T. = Not Tested.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to $pH_7$ with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

TABLE 4

| Pharmacokinetic Parameters | | | | | | | |
|---|---|---|---|---|---|---|---|
| Example | Ke (min.−1 | Clt/F (L/hr.kg) | VD/F (L/kg) | Tmax (hrs.) | Cmax (ng/ml) | t0.5 (min.) | A.U.C. (ng · hr/ml) o-infinity |
| 1 | 0.0104 ±0.0009 | 0.437 ±0.032 | 0.729 ±0.120 | 1–2 | 1676 +2.02 | 67 range = 57–86 | 4651 319 |

Canine Model of Coronary Artery Thrombosis

Surgical preparation and instrumentation of the dogs are as described in Jackson, et al., *Circulation,* 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for ≧30 minutes.

Hematology and template bleeding time determinations

Whole blood cell counts, hemoglobin, and hematocrit values are determined on a 40-μl sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacolo,* 21, 587–599 (1993).

TABLE 5

| Canine Model of Coronary Artery Thromboses | | |
|---|---|---|
| Example | Dose mg/kg · hr | Time to Occlusion (min) |
| 1 | 0.25 | 60 |
| | 0.50 | 150 |
| | 1.00 | >225 |

The compound of Example 1 was also evaluated in the Template Bleeding Time assay at 0.25, 0.50 and 1.0 mg/kg.hr. Over a 240 minute time, the compound of Example 1 showed no significant effect on template bleeding time.

The ability of the bisulfite adducts of the present invention to maintain the L-configuration for the arginine residue was demonstrated as described below. It is believed similar beneficial results will be afforded for all arginine aldehyde compounds defined above.

Epimerization Inhibition Procedures

A 55.55 mM aqueous sodium phosphate solution (adjusted to pH 7.4 with sodium hydroxide) was mixed with an aqueous 27.77 mM sodium bisulfite/27.77 mM sodium phosphate solution (adjusted to pH 7.4 with sodium hydroxide) and water in various ratios to produce buffers containing 0, 5.55, 11.11, 16.66, 22.22 and 27.77 mM sodium bisulfite. A 0.9 ml aliquot of each sodium bisulfite/phosphate buffer was added to separate 13×100 mm culture tubes and placed in a 50° C. Tempblok® heater for 15 minutes. To each culture tube 0.1 ml of a 1 mg/ml aqueous solution of the compound of Example 75 was added and mixed well. The culture tubes were returned to the heater and 50 μl aliquots of each sample were removed at 0, 0.5, 1.2, 2, 3, 4, 6 and 8 hr and mixed with 250 μl of 100 mM trifluoroacetic acid in acetonitrile/water (95:5, v/v) and 700 μl of 1 mM 2,4-dinitrophenylhydrazine in acetonitrile/acetic acid (9:1, v/v) in separate 12×75 mm culture tubes. These samples were allowed to react for 30 minutes at 60° C. and were then evaporated to dryness with nitrogen in a 55° C. N-Evap. The residue was dissolved in 1 ml of methanol and transferred to Varian Si BondElut SPE columns (1 ml) previously conditioned with 2 ml of water then 2 ml of methanol. The dissolved samples were pulled through slowly with a slight vaccum, and the sorbent layer was then washed with 2-1 ml volumes of methanol. The SPE columns were then dried at full vacuum (~25 in. Hg) then 500 μl of 500 mM potassium chloride was passed through the SPE columns. The compounds of interest were eluted with 300 μl of methanol/500 mM potassium chloride (1:1, v/v) into 12×75 mm culture tubes. These eluates were analyzed by the HPLC system described below.

The mobile phase was acetonitrile/methanol/500 mM ammonium acetate pH 7 (3:3:4, v/v) pumped at 1 ml/min with a Shimadzu LC-10AD pump. The column was a Zorbax SB-C8 150×4.6 mm maintained at 40° C. with a Jones Chromatography 7960 column heater. Fifty microliter injections were made with a Waters WISP 712 autosampler. Detection was accomplished with a Kratos 783 UV detector at 360 nm. The percentage of the DLD isomer was calculated using the peak areas of the DLL and DLD isomers in the chromatograms and the following equation:

$$\%\ DLD\ \text{Isomer} = 100 \times \frac{DLD\ \text{ISOMER Peak Area}}{(DLD\ \text{ISOMER Peak Area} + DLL\ \text{ISOMER Peak Area})}$$

The results are reported below in Table 6:

TABLE 6

| | Percentage of DLD Isomer Sodium Bisulfite Concentration (mM) | | | | | |
|---|---|---|---|---|---|---|
| Time(hr) | 0 | 5 | 10 | 15 | 20 | 25 |
| 0 | 7.33 | 7.35 | 7.54 | 8.37 | 7.65 | 8.16 |
| 0.5 | 31.91 | 14.64 | 10.79 | 10.31 | 9.90 | 9.47 |
| 1.2 | 44.72 | 24.74 | 17.72 | 15.19 | 12.88 | 11.42 |
| 2 | 48.95 | 34.64 | 25.55 | 21.41 | 17.28 | 14.78 |
| 3 | 50.21 | 42.75 | 35.08 | 28.54 | 23.70 | 18.66 |
| 4 | 50.27 | 47.21 | 41.99 | 35.26 | 29.34 | 24.34 |
| 6 | 50.03 | 48.75 | 50.73 | 46.26 | 43.32 | 37.60 |
| 8 | 50.15 | 49.61 | 51.60 | 50.58 | 48.73 | 46.26 |

Epimerization Inhibition Procedures (Compound of Example 80, Step F)

A 55.55 mM aqueous sodium phosphate solution (adjusted pH 7.4 with sodium hydroxide) was mixed with a 27.77 mM sodium bisulfite/27.77 mM sodium phosphate solution (adjusted pH 7.4 with sodium hydroxide) and water in various ratios to produce buffers containing 0,5.55, 16.66 and 27.77 mM sodium bisulfite. A 0.9 ml aliquot of each sodium bisulfite/phosphate buffer was added to separate $13\times100$ mm culture tubes and placed in a 50° C. Isotherm Tempblok ® heater for 15 minutes. To each culture tube 0.1 ml of a 1 mg/ml aqueous solution of D-3-Piq-Pro-Arg-H.$H_2SO_4$ (Example 80, Step F) was added and mixed well. The culture tubes were returned to the heater and 50 μl aliquots of each sample were removed at 0, 0.5, 1, 2, 3, 4, 6 and 8 hours and mixed with 250 μl of 100 mM trifluoroacetic acid in acetonitrile/water (95:5, v/v) and 700 μl of 1 mM 2,4-dinitrophenylhydrazine in methanol/acetic acid (9:1, v/v) in separate $12\times75$ mm culture tubes. These samples were allowed to react for 15 minutes at 90° C. and were then evaporated to dryness with nitrogen in a 55° C. N-Evap. The residue was dissolved in 1 ml of methanol and transferred to Varian Si BondElut SPE columns (1 ml) previously conditioned with 1 ml of water then 1 ml of methanol. The dissolved samples were pulled through solwly with a slight vacuum, and the sorbent layer was then washed with 2-1 ml volumes of methanol. The SPE columns were then dried at full vacuum (~25 in. Hg) and the compounds of interest were eluted with 300 μl of acetonitrile/100 mM sodium dodecyl sulfate (adjusted to pH 3 with phosphoric acid) (7:3, v/v) into $12\times75$ mm culture tubes. These eluates were analyzed by the HPLC system described below.

The mobile phase was acetonitrile/180 mM sodium dodecyl sulfate (adjusted to pH 3 with phosphoric acid) (85:15, v/v) pumped at 0.5 ml/min with a Shimadzu LC-10AD pump. The column was an Inertsil ODS(2) $150\times3.0$ mm maintained at 40° C. with a Jones Chromatography 7960 column heater. Twenty-five microliter injections were made with a Waters WISP 712 autosampler. Detection was accomplished with a Kratos 783 UV detector at 360 nm. The percentage of the DLD isomer was calculated using the peak areas of the DLL and DLD isomers in the chromatograms and the following equation:

$$\%\ DLD\ \text{Isomer} = 100 \times \frac{DLD\ \text{ISOMER Peak Area}}{(DLD\ \text{ISOMER Peak Area} + DLL\ \text{ISOMER Peak Area})}$$

The results are reported below in Table 7:

TABLE 7

| | Percentage of DLD Isomer Sodium Bisulfite Concentration (mM) | | | |
|---|---|---|---|---|
| Time (hr) | 0 | 5 | 15 | 25 |
| 0 | 4.84 | 4.23 | 4.16 | 3.71 |
| 0.5 | 46.00 | 43.52 | 27.80 | 4.56 |
| 1 | 49.42 | 48.99 | 40.63 | 5.14 |
| 2 | 49.53 | 47.98 | 45.06 | 5.31 |
| 3 | 50.16 | 49.89 | 45.72 | 5.79 |
| 4 | 50.36 | 49.90 | 49.24 | 6.06 |
| 6 | 49.71 | 49.80 | 49.63 | 6.39 |
| 8 | 49.92 | 50.08 | 49.99 | 6.72 |

We claim:

1. A bisulfite adduct having the formula

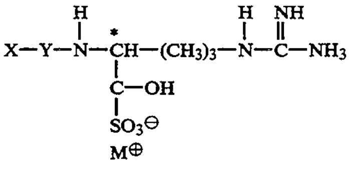

I wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

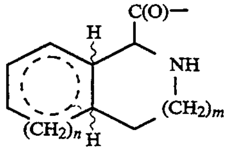

and

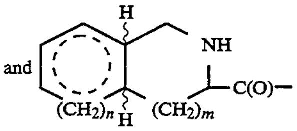

where n is 1-3 and m is 0-3 and in a sulfur containing group the sulfur may be oxidized with one or two oxygen atoms;

2) a group

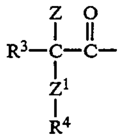

where Z is hydrogen, hydroxy, $C_1$-$C_4$ alkoxy or $-NHR^2$;

$R^2$ is hydrogen, $C_1$-$C_6$ alkyl, cyclopentyl, cyclohexyl a group

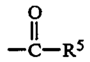

or $-S(O)_p-R^5$ where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, cyclopentyl-$CH_2$—, cyclohexyl-$CH_2$—, amino, mono ($C_1$-$C_4$)alkylamino, di($C_1$-$C_4$)alkylamino, unsubstituted or substituted aryl, where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or 2;

$R^3$ is hydrogen, $C_1$-$C_4$ alkyl, unsubstituted or substituted phenyl or unsubstituted or substituted benzyl;

$Z^1$ is a bond or $-CH_2-$;

$R^4$ is $C_1$-$C_6$ alkyl, $C_1$-$C_4$ alkoxy, cyclopentyl, cyclohexyl, unsubstituted or substituted aryl where aryl is phenyl or naphthyl, or a 5 membered unsubstituted or substituted heterocyclic ring, having one sulfur atom;

when Z is $-NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

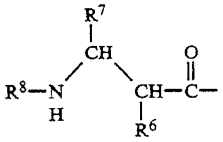

wherein $R^6$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–$C_4$)alkyl, or cyclohexyl($C_1$–$C_4$)alkyl;

$R^7$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl ($C_1$–$C_4$)alkyl or cyclohexyl ($C_1$–$C_4$)alkyl;

$R^8$ is hydrogen, $C_1$–$C_4$ alkyl or ($C_1$–$C_4$ alkyl)$S(O)_q$ where q is 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another nitrogen;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

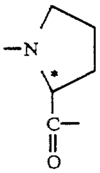
or
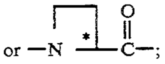

M is a pharmaceutically acceptable alkali metal or alkaline earth metal cation;

and pharmaceutically acceptable salts and solvates thereof.

2. A bisulfite adduct of claim 1 where X is a group

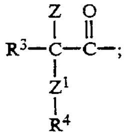

Z is —$NHR^2$;

$R^2$ is $C_1$–$C_6$ alkyl,

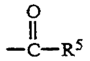

or —$S(O)_p$-$R^5$;

R3 is hydrogen or $C_1$–$C_4$ alkyl;

$Z^1$ is a bond or —$CH_2$—;

$R^4$ is unsubstituted or substituted aryl where aryl is phenyl or naphthyl;

$R^5$ is $C_1$–$C_4$ alkyl, $C_1$–$C_4$ alkoxy, amino, mono($C_1$–$C_4$)alkylamino or di($C_1$–$C_4$)alkylamino;

or an unsubstituted or monosubstituted fused bicyclic ring selected from

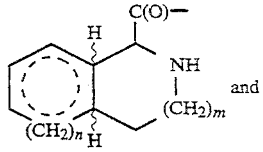
and
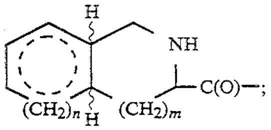

M is sodium, potassium, calcium or magnesium; and pharmaceutically acceptable sales and solvates thereof.

3. A bisulfite adduct of claim 2 where

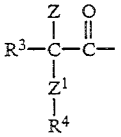

X is a group

Z is —$NHR^2$;

$R^2$ is $C_1$–$C_6$ alkyl;

$R^3$ is hydrogen;

$Z^1$ a bond or —$CH_2$—;

$R^4$ is unsubstituted or substituted phenyl;

or a fused bicyclic ring selected from

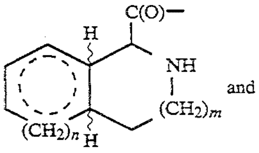
and
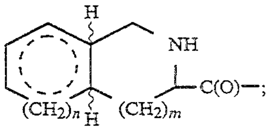

M is sodium;

and pharmaceutically acceptable salts or solvates thereof.

4. A bisulfite adduct of claim 1 which is N-methyl-D-cyclohexylalanyl-L-prolinyl-L-arginine aldehyde bisulfite and pharmaceutically acceptable salts and solvates thereof.

5. A bisulfite adduct of claim 3 which is N-methyl-D-phenylglycinyl-L-prolinyl-NH-CH[$(CH_2)_3$NH-C(NH)-$NH_2$]-C(OH)$SO_3$ Na and pharmaceutically acceptable salts and solvates thereof.

6. A bisulfite adduct of claim 3 which is D-1,2,3,4,4a,6,7,8,8a-perhydroisoquinolin-3-ylcarbonyl-L-prolinyl-L-arginine aldehyde bisulfite, and pharmaceutically acceptable salts and solvates thereof.

7. A bisulfite adduct of claim 3 which is N-methyl-D-phenylalanyl-L-prolinyl-L-arginine aldehyde bisulfite and pharmaceutically acceptable salts and solvates thereof.

8. A bisulfite adduct of claim 3 which is D-1,2,3,4,4a,6,7,8,8a-perhydroisoquinol-1-ylcarbonyl-L-prolinyl-L-arginine aldehyde bisulfite and pharmaceutically acceptable salts and solvates thereof.

9. A bisulfite adduct of claim 3 which is D-1,2,3,4-tetrahydroisoquinol-1-ylcarbonyl-L-prolinyl-L-arginine aldehyde bisulfite and pharmaceutically acceptable salts and solvates thereof.

10. A pharmaceutical formulation comprising in association with a pharmaceutically acceptable carrier, diluent, or excipient, a bisulfite adduct of the formula.

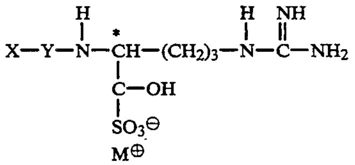

I wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

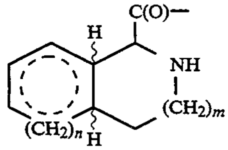

and

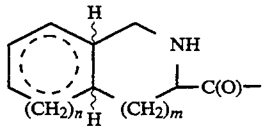

where n is 1-3 and m is 0-3 and in a sulfur containing group the sulfur may be oxidized with one or two oxygen atoms;

2) a group

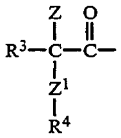

where Z is hydrogen, hydroxy, $C_1$-$C_4$ alkoxy or —$NHR^2$;

$R^2$ is hydrogen, $C_1$-$C_6$ alkyl, cyclopentyl, cyclohexyl, a group

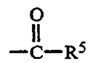

or —$S(O)_p$-$R^5$ where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, cyclopentyl-$CH_2$—, cyclohexyl-$CH_2$—, amino, mono ($C_1$-$C_4$)alkylamino, di($C_1$-$C_4$)alkylamino, unsubstituted or substituted aryl, where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or 2;

$R^3$ is hydrogen, $C_1$-$C_4$ alkyl, unsubstituted or substituted phenyl or unsubstituted or substituted benzyl;

$Z^1$ is a bond or —$CH_2$—;

$R^4$ is $C_1$-$C_6$ alkyl, $C_1$-$C_4$ alkoxy, cyclopentyl, cyclohexyl, unsubstituted or substituted aryl where aryl is phenyl or naphthyl, or a 5 membered unsubstituted or substituted heterocyclic ring, having one sulfur atom;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

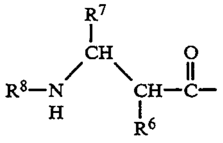

wherein $R^6$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl, or cyclohexyl($C_1$-$C_4$)alkyl;

$R^7$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl ($C_1$-$C_4$)alkyl or cyclohexyl($C_1$-$C_4$)alkyl;

$R^8$ is hydrogen, $C_1$-$C_4$ alkyl or ($C_1$-$C_4$ alkyl)$S(O)_q$ where q is 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another nitrogen;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

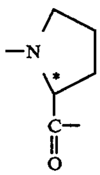

or

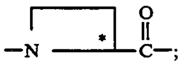

M is a pharmaceutically acceptable alkali metal or alkaline earth metal cation;

and pharmaceutically acceptable salts and solvates thereof.

11. A formulation of claim 10 where X is a group

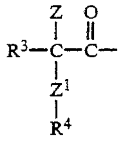

Z is —$NHR^2$;

$R^2$ is $C_1$–$C_6$ alkyl,

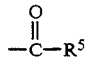

or —$S(O)_p$-$R^5$;

$R^3$ is hydrogen or $C_1$–$C_4$ alkyl;

$Z^1$ is a bond or —$CH_2$—;

$R^4$ is unsubstituted or substituted aryl where aryl is phenyl or naphthyl;

$R^5$ is $C_1$–$C_4$ alkyl, $C_1$–$C_4$ alkoxy, amino, mono($C_1$–$C_4$) alkylamino or di($C_1$–$C_4$)alkylamino;

or an unsubstituted or monosubstituted fused bicyclic ring selected from

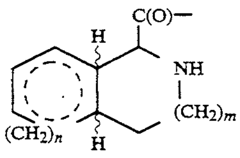

and

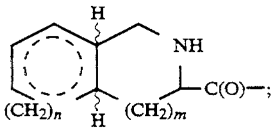

M is sodium, potassium, calcium or magnesium; and pharmaceutically acceptable salts and solvates thereof.

12. A formulation of claim 11 where

X is a group

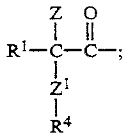

Z is —$NHR^2$;

$R^2$ is $C_1$–$C_6$ alkyl;

$R^3$ is hydrogen;

$Z^1$ is a bond or —$CH_2$—;

$R^4$ is unsubstituted or substituted phenyl;

or a fused bicyclic ring selected from

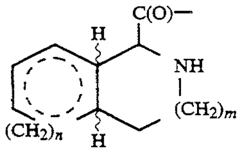

and

-continued

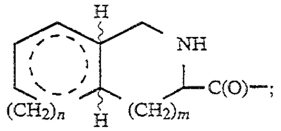

M is sodium;

and pharmaceutically acceptable salts or solvates thereof.

13. A formulation of claim 10 where said bisulfite adduct is N-methyl-D-cyclohexylalanyl-L-prolinyl-L-arginine aldehyde bisulfite and pharmaceutically acceptable salts and solvates thereof.

14. A formulation of claim 12 where said bisulfite adduct is N-methyl-D-phenylglycinyl-L-prolinyl-NH-CH[$(CH_2)_3$NH-C(NH)-$NH_2$]-C(OH)$SO_3$ Na and pharmaceutically acceptable salts and solvates thereof.

15. A formulation of claim 12 where said bisulfite adduct is D-1,2,3,4,4a,6,7,8,8a-perhydroisoquinolin-3-ylcarbonyl-L-prolinyl-L-arginine aldehyde bisulfite and pharmaceutically acceptable salts and solvates thereof.

16. A formulation of claim 12 where said bisulfite adduct is N-methyl-D-Phenylalanyl-L-prolinyl-L-arginine aldehyde bisulfite and pharmaceutically acceptable salts and solvates thereof.

17. A formulation of claim 12 where said bisulfite adduct is D-1,2,3,4,4a,6,7,8,8a-perhydroisoquinol-1-ylcarbonyl-L-prolinyl-L-arginine aldehyde bisulfite and pharmaceutically acceptable salts and solvates thereof.

18. A formulation of claim 12 where said bisulfite adduct is D-1,2,3,4-tetrahydroisoquinol-1-ylcarbonyl-L-prolinyl-L-arginine aldehyde bisulfite and pharmaceutically acceptable salts and solvates thereof.

19. A method of inhibiting thrombin in mammals, comprising administering to a mammal requiring thrombin inhibition, an effective dose of a bisulfite adduct having the formula

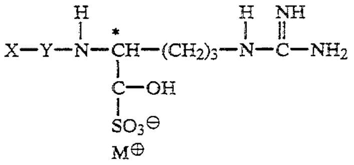 I wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

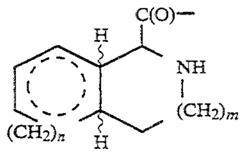

and

-continued

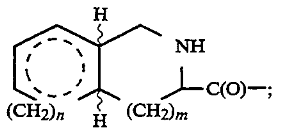

where n is 1-3 and m is 0-3 and in a sulfur containing group the sulfur may be oxidized with one or two oxygen atoms;

2) a group

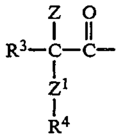

where Z is hydrogen, hydroxy, $C_1$-$C_4$ alkoxy or —$NHR^2$;

$R^2$ is hydrogen $C_1$-$C_6$ alkyl, cyclopentyl, cyclohexyl, a group

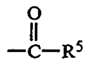

or —$S(O)_p$-$R^5$ where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, cyclopentyl-$CH_2$—, cyclohexyl-$CH_2$—, amino, mono ($C_1$-$C_4$)alkylamino, di($C_1$-$C_4$)alkylamino, unsubstituted or substituted aryl, where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or 2;

$R^3$ is hydrogen, $C_1$-$C_4$ alkyl unsubstituted or substituted phenyl or unsubstituted or substituted benzyl;

$Z^1$ is a bond or —$CH_2$—;

$R^4$ is $C_1$-$C_6$ alkyl, $C_1$-$C_4$ alkoxy, cyclopentyl, cyclohexyl, unsubstituted or substituted aryl where aryl is phenyl or naphthyl, or a 5 membered unsubstituted or substituted heterocyclic ring, having one sulfur atom;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

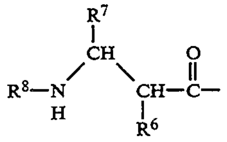

wherein $R^6$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl ($C_1$-$C_4$)alkyl, or cyclohexyl ($C_1$-$C_4$)alkyl;

$R^7$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl ($C_1$-$C_4$)alkyl or cyclohexyl ($C_1$-$C_4$)alkyl;

$R^8$ is hydrogen, $C_1$-$C_4$ alkyl or ($C_1$-$C_4$ alkyl)$S(O)_q$ where q is 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another nitrogen;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

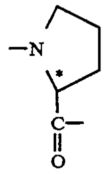

or

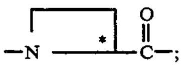

M is a pharmaceutically acceptable alkali metal or alkaline earth metal cation;

and pharmaceutically acceptable salts and solvates thereof.

20. The method of claim 19 where X is a group

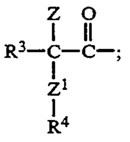

Z is —$NHR^2$;

$R^2$ is $C_1$-$C_6$ alkyl,

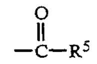

or $S(O)_p$-$R^5$;

$R^3$ is hydrogen or $C_1$–$C_4$ alkyl;

$Z^1$ is a bond or —$CH_2$—;

$R^4$ is unsubstituted or substituted aryl where aryl is phenyl or naphthyl;

$R^5$ is $C_1$–$C_4$ alkyl, $C_1$–$C_4$ alkoxy, amino, mono($C_1$–$C_4$) alkylamino or di($C_1$–$C_4$)alkylamino;

or an unsubstituted or monosubstituted fused bicyclic ring selected from

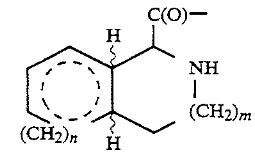

and

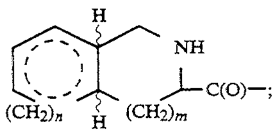

M is sodium, potassium, calcium or magnesium; and pharmaceutically acceptable salts and solvates thereof.

21. The method of claim 20 where

X is a group

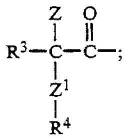

Z is —$NHR^2$;

$R^2$ is $C_1$–$C_6$ alkyl;

$R^3$ is hydrogen;

$Z^1$ is —$CH_2$—;

$R^4$ is unsubstituted or substituted phenyl;

or a fused bicyclic ring selected from

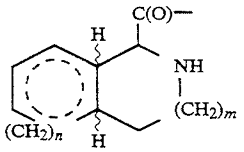

and

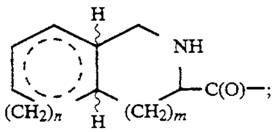

M is sodium;

and pharmaceutically acceptable salts or solvates thereof.

22. The method of claim 19 where said bisulfite adduct is N-methyl-D-cyclohexylalanyl-L-prolinyl-L-arginine aldehyde bisulfite or a pharmaceutically acceptable salt or solvate thereof.

23. The method of claim 21 where said bisulfite adduct is N-methyl-D-phenylglycinyl-L-prolinyl-NH-CH[$(CH_2)_3$NH-C(NH)-$NH_2$]-C(OH)$SO_3$ Na or a pharmaceutically acceptable salt or solvate thereof.

24. The method of claim 21 where said bisulfite adduct is D-1,2,3,4,4a,6,7,8,8a-Perhydroisoquinolin-3-ylcarbonyl-L-prolinyl-L-arginine aldehyde bisulfite or a pharmaceutically acceptable salt or solvate thereof.

25. The method of claim 21 where said bisulfite adduct is N-methyl-D-phenylalanyl-L-prolinyl-L-arginine aldehyde bisulfite or a pharmaceutically acceptable salt or solvate thereof.

26. The method of claim 21 where said bisulfite adduct is D-1,2,3,4,4a,6,7,8,8a-perhydroisoquinol-1-ylcarbonyl-L-prolinyl-L-arginine aldehyde bisulfite or a pharmaceutically acceptable salt or solvate thereof.

27. The method of claim 21 where said bisulfite adduct is D-1,2,3,4-tetrahydroisoquinol-1-ylcarbonyl-L-prolinyl-L-arginine aldehyde bisulfite or a pharmaceutically acceptable salt or solvate thereof.

28. A method of treating thromboembolic disorder in mammals, comprising administering to a mammal requiring thromboembolic disorder treatment, an effective dose of a bisulfite adduct having the formula

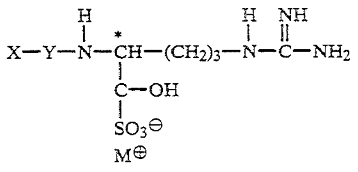

I wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

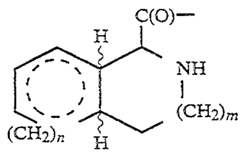

and

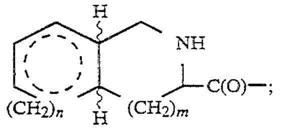

where n is 1–3 and m is 0, 1–3 and in a sulfur containing group the sulfur may be oxidized with one or two oxygen atoms;

2) a group

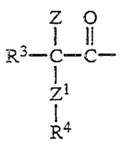

where Z is hydrogen, hydroxy, $C_1$-$C_4$ alkoxy or —$NHR^2$;

$R^2$ is hydrogen, $C_1$-$C_6$ alkyl, cyclopentyl, cyclohexyl, a group

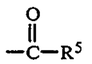

or —$S(O)_p$-$R^5$ where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, cyclopentyl-$CH_2$—, cyclohexyl-$CH_2$—, amino, mono ($C_1$-$C_4$)alkylamino, di($C_1$-$C_4$)alkylamino, unsubstituted or substituted aryl, where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or 2;

$R^3$ is hydrogen, $C_1$-$C_4$ alkyl, unsubstituted or substituted phenyl or unsubstituted or substituted benzyl;

$Z^1$ is a bond or —$CH_2$—;

$R^4$ is $C_1$-$C_6$ alkyl, $C_1$-$C_4$ alkoxy, cyclopentyl, cyclohexyl, unsubstituted or substituted aryl where aryl is phenyl or naphthyl, or a 5 membered unsubstituted or substituted heterocyclic ring, having one sulfur atom;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

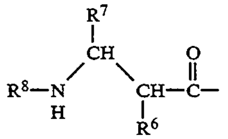

wherein $R^6$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl, or cyclohexyl($C_1$-$C_4$)alkyl;

$R^7$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl ($C_1$-$C_4$)alkyl or cyclohexyl ($C_1$-$C_4$)alkyl;

$R^8$ is hydrogen, $C_1$-$C_4$ alkyl or ($C_1$-$C_4$ alkyl)$S(O)_q$ where q is 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another nitrogen;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hereto atom selected from nitrogen, oxygen and sulfur, or an unsubstituted or substituted 9 or 10 membered nitrogen containing heterocyclic ring which may further contain another hereto atom selected from nitrogen, oxygen and sulfur;

Y is

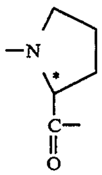

or

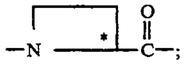

M is a pharmaceutically acceptable alkali metal or alkaline earth metal cation;

and pharmaceutically acceptable sates and solvates thereof.

29. The method of claim 28 where X is a group

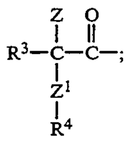

Z is —$NHR^2$;

$R^2$ is $C_1$-$C_6$ alkyl,

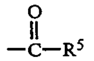

or —$S(O)_p$-$R^5$;

$R^3$ is hydrogen or $C_1$-$C_4$ alkyl;

$Z^1$ is a bond or —$CH_2$—;

$R^4$ is unsubstituted or substituted aryl where aryl is phenyl or naphthyl;

$R^5$ is $C_1$-$C_4$ alkyl, $C_1$-$C_4$ alkoxy, amino, mono($C_1$-$C_4$) alkylamino or di($C_1$-$C_4$)alkylamino;

or an unsubstituted or monosubstituted fused bicyclic ring selected from

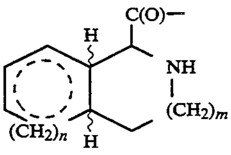

and

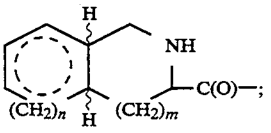

M is sodium, potassium, calcium or magnesium; and pharmaceutically acceptable salts and solvates thereof.

30. The method of claim 29 where

X is a group

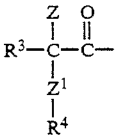

Z is $-NHR^2$;
$R^2$ is $C_1$-$C_6$ alkyl;
$R^3$ is hydrogen;
$Z^1$ is a bond or $-CH_2-$;
$R^4$ is unsubstituted or substituted phenyl;
or a fused bicyclic ring selected from

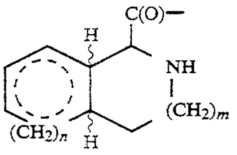
and
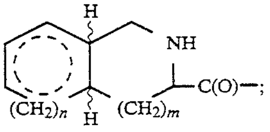

M is sodium;
and pharmaceutically acceptable salts or solvates thereof.

31. The method of claim 23 where said bisulfite adduct is N-methyl-D-cyclohexylalanyl-L-prolinyl-L-arginine aldehyde bisulfite or a pharmaceutically acceptable salt or solvate thereof.

32. The method of claim 30 where said bisulfite adduct is N-methyl-D-phenylglycinyl-L-prolinyl-NH-$CH[(CH_2)_3NH-C(NH)-NH_2]-C(OH)SO_3$ Na or a pharmaceutically acceptable salt or solvate thereof.

33. The method of claim 30 where said bisulfite adduct is D-1,2,3,4,6,7,8-perhydroisoquinolin-3-yl carbonyl-L-prolinyl-L-arginine aldehyde bisulfite or a pharmaceutically acceptable salt or solvate thereof.

34. The method of claim 30 where said bisulfite adduct is N-methyl-D-phenylalanyl-L-prolinyl-L-arginine aldehyde bisulfite or a pharmaceutically acceptable salt or solvate thereof.

35. The method of claim 30 where said bisulfite adduct is D-1,2,3,4,4a,6,7,8,8a-perhydroisoquinol-1-ylcarbonyl-L-prolinyl-L-arginine aldehyde bisulfite or a pharmaceutically acceptable salt or solvate thereof.

36. The method of claim 30 where said bisulfite adduct is D-1,2,3,4-tetrahydroisoquinol-1-ylcarbonyl-L-prolinyl-L-arginine aldehyde bisulfite or a pharmaceutically acceptable salt or solvate thereof.

37. A method of inhibiting coagulation in mammals, comprising administering to a mammal requiring coagulation inhibition, an effective dose of a bisulfite adduct having the formula

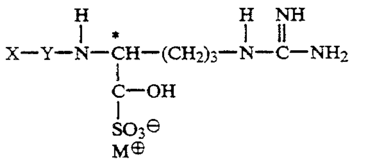
I wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

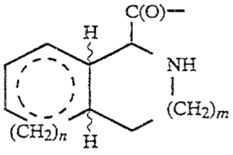
and
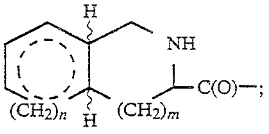

where n is 1-3 and m is 0-3 and in a sulfur containing group the sulfur may be oxidized with one or two oxygen atoms;

2) a group

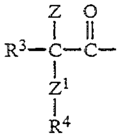

where Z is hydrogen, hydroxy, $C_1$-$C_4$ alkoxy or $-NHR^2$;

$R^2$ is hydrogen, $C_1$-$C_6$ alkyl, cyclopentyl, cyclohexyl, a group

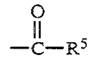

or $-S(O)_p-R^5$ where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, cyclopentyl-$CH_2-$, cyclohexyl-$CH_2-$, amino, mono ($C_1$-$C_4$)alkylamino, di($C_1$-$C_4$)alkylamino, unsubstituted or substituted aryl, where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or 2;

$R^3$ is hydrogen, $C_1$-$C_4$ alkyl, unsubstituted or substituted phenyl or unsubstituted or substituted benzyl;

$Z^1$ is a bond or $-CH_2-$;

$R^4$ is $C_1$-$C_6$ alkyl, $C_1$-$C_4$ alkoxy, cyclopentyl, cyclohexyl, unsubstituted or substituted aryl where aryl is phenyl or naphthyl, or a 5 membered unsubstituted or substituted heterocyclic ring, having one sulfur atom;

when Z is $-NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

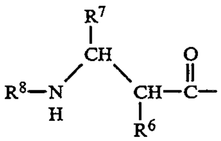

wherein $R^6$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl, or cyclohexyl($C_1$-$C_4$)alkyl;

$R^7$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl ($C_1$-$C_4$)alkyl or cyclohexyl ($C_1$-$C_4$)alkyl;

$R^8$ is hydrogen, $C_1$-$C_4$ alkyl or ($C_1$-$C_4$ alkyl)$S(O)_q$ where q is 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another nitrogen;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

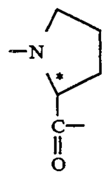

or

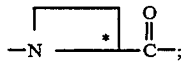

M is a pharmaceutically acceptable alkali metal or alkaline earth metal cation;

and pharmaceutically acceptable salts and solvates thereof.

38. The method of claim 37 where X is a group

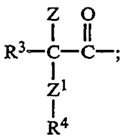

Z is —$NHR^2$;

$R^2$ is $C_1$-$C_6$ alkyl,

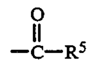

or —$S(O)_p$-$R^5$;

$R^3$ is hydrogen or $C_1$-$C_4$ alkyl;

$Z^1$ is a bond or —$CH_2$—;

$R^4$ is unsubstituted or substituted aryl where aryl is phenyl or naphthyl;

$R^5$ is $C_1$-$C_4$ alkyl, $C_1$-$C_4$ alkoxy, amino, mono ($C_1$-$C_4$) alkylamino or di($C_1$-$C_4$)alkylamino;

or an unsubstituted or monosubstituted fused bicyclic ring selected from

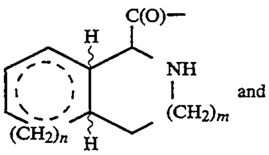

and

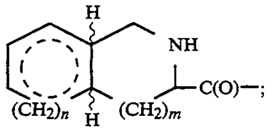

M is sodium, potassium, calcium or magnesium; and pharmaceutically acceptable salts and solvates thereof.

39. The method of claim 38 where

X is a group

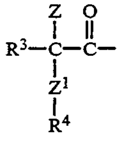

Z is —$NHR^2$;

$R^2$ is $C_1$-$C_6$ alkyl;

$R^3$ is hydrogen;

$Z^1$ is a bond or —$CH_2$—;

$R^4$ is unsubstituted or substituted phenyl;

or a fused bicyclic ring selected from

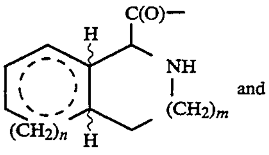

and

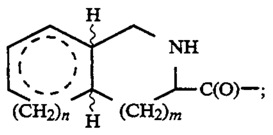

M is sodium;

and pharmaceutically acceptable sales or solvates thereof.

40. The method of claim 37 where said bisulfite adduct is N-methyl-D-cyclohexylalanyl-L-prolinyl-L-arginine aldehyde bisulfite or a pharmaceutically acceptable salt or solvate thereof.

41. The method of claim 39 where said bisulfite adduct is N-methyl-D-phenylglycinyl-L-prolinyl-NH-CH[$(CH_2)_3$NH-C(NH)-$NH_2$]-C(OH)$SO_3$ Na or a pharmaceutically acceptable salt or solvate thereof.

42. The method of claim 39 where said bisulfite adduct is D-1,2,3,4,4a,6,7,8,8a-perhydroisoquinolin-3-ylcarbonyl-L-prolinyl-L-arginine aldehyde bisulfite or a pharmaceutically acceptable salt or solvate thereof.

43. The method of claim 39 where said bisulfite adduct is N-methyl-D-phenylalanyl-L-prolinyl-L-arginine aldehyde bisulfite or a pharmaceutically acceptable salt or solvate thereof.

44. The method of claim 39 where said bisulfite adduct is D-1,2,3,4,4a,6,7,8,8a-perhydroisoquinol-1-ylcarbonyl-L-prolinyl-L-arginine aldehyde bisulfite or a pharmaceutically acceptable salt or solvate thereof.

45. The method of claim 39 where said bisulfite adduct is D-1,2,3,4-tetrahydroisoquinol-1-ylcarbonyl-L- prolinyl-L-arginine aldehyde bisulfite or a pharmaceutically acceptable salt or solvate thereof.

46. A method of inhibiting epimerization in arginine aldehyde containing tripeptides comprising combining said arginine aldehyde and about a stoichiometric amount of a pharmaceutically acceptable alkali metal or alkaline earth metal bisulfite to afford an arginine aldehyde bisulfite adduct.

47. The method of claim 46 where said arginine aldehyde containing tripeptide has the formula

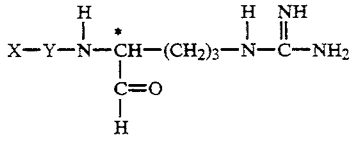

Ia wherein

X is 1) an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

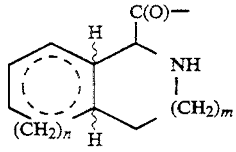

and

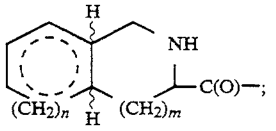

where n is 1-3 and m is 0-3 and in a sulfur containing group the sulfur may be oxidized with one or two oxygen atoms;

2) a group

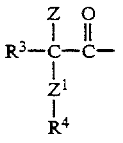

where Z is hydrogen, hydroxy, $C_1$-$C_4$ alkoxy or —$NHR^2$;

$R^2$ is hydrogen, $C_1$-$C_6$ alkyl, cyclopentyl, cyclohexyl, a group

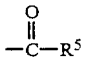

or —$S(O)_p$-$R^5$ where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, cyclopentyl-$CH_2$—, cyclohexyl-$CH_2$—, amino, mono ($C_1$-$C_4$)alkylamino, di($C_1$-$C_4$)alkylamino, unsubstituted or substituted aryl, where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

p is 0, 1 or 2;

$R^3$ is hydrogen, $C_1$-$C_4$ alkyl, unsubstituted or substituted phenyl or unsubstituted or substituted benzyl;

$Z^1$ is a bond or —$CH_2$—;

$R^4$ is $C_1$-$C_6$ alkyl, $C_1$-$C_4$ alkoxy, cyclopentyl, cyclohexyl, unsubstituted or substituted aryl where aryl is phenyl or naphthyl, or a 5 membered unsubstituted or substituted heterocyclic ring, having one sulfur atom;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group;

3) a group

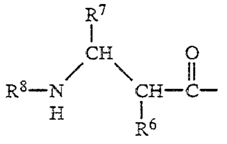

wherein $R^6$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl, or cyclohexyl ($C_1$-$C_4$)alkyl;

$R^7$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl ($C_1$-$C_4$)alkyl or cyclohexyl ($C_1$-$C_4$)alkyl;

$R^8$ is hydrogen, $C_1$-$C_4$ alkyl or ($C_1$-$C_4$ alkyl)$S(O)_q$ where q is 1 or 2;

$R^6$ and $R^7$, with the carbon atoms to which they are bonded, are combined to afford a 5 or 6 membered cycloalkyl group, a phenyl group or norbornanyl group;

$R^7$ and $R^8$, with the respective carbon and nitrogen atoms to which they are bonded, are combined to afford an unsubstituted or substituted 5 or 6 membered nitrogen containing heterocyclic ring which may further contain another nitrogen;

$R^6$, $R^7$ and $R^8$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

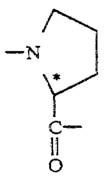

or

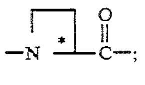

and pharmaceutically acceptable salts and solvates thereof.

48. The method of claim 47 where X is a group

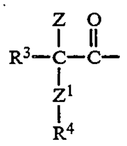

Z is —$NHR^2$;

$R^2$ is $C_1$-$C_6$ alkyl,

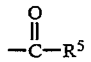

or —$S(O)_p$-$R^5$;

$R^3$ is hydrogen or $C_1$-$C_4$ alkyl;

$Z^1$ is a bond or —$CH_2$—;

$R^4$ is unsubstituted or substituted aryl where aryl is phenyl or naphthyl;

$R^5$ is $C_1$-$C_4$ alkyl, $C_1$-$C_4$ alkoxy, amino, mono($C_1$-$C_4$) alkylamino or di($C_1$-$C_4$)alkylamino;

or an unsubstituted or monosubstituted fused bicyclic ring selected from

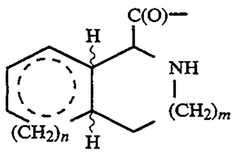

and

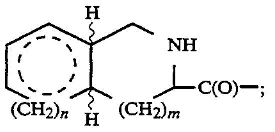

said bisulfite is sodium, potassium, calcium or magnesium;

and pharmaceutically acceptable salts and solvates thereof.

49. The method of claim 48 where

X is a group

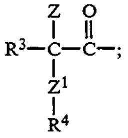

Z is —$NHR^2$;
$R^2$ is $C_1$-$C_6$ alkyl;
$R^3$ is hydrogen;
$Z^1$ is a bond or —$CH_2$—;
$R^4$ is unsubstituted or substituted phenyl;
or a fused bicyclic ring selected from

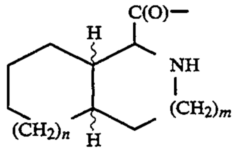

and

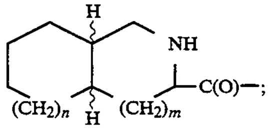

said bisulfite is sodium;

and pharmaceutically acceptable salts or solvates thereof.

* * * * *

UNITED STATES PATENT AND TRADEMARK OFFICE
CERTIFICATE OF CORRECTION

PATENT NO. : 5,436,229

DATED : July 25, 1995

INVENTOR(S) : Kennth J. Ruterbories and Robert T. Shuman

It is certified that an error appears in the above-identified patent and that said Letters Patent is hereby corrected as shown below:

Column 120, Line 27, delete "sates" replace with --salts--.

Column 121, Line 26, delete "23" replace with --28--.

Signed and Sealed this

Fourteenth Day of November, 1995

Attest:

Bruce Lehman

BRUCE LEHMAN

*Attesting Officer*

*Commissioner of Patents and Trademarks*